(12) United States Patent
Reddy et al.

(10) Patent No.: US 11,650,172 B2
(45) Date of Patent: May 16, 2023

(54) CALORIMETER

(71) Applicant: The Regents of The University of Michigan, Ann Arbor, MI (US)

(72) Inventors: Pramod Reddy, Ann Arbor, MI (US); Edgar Meyhofer, Ann Arbor, MI (US); Anthony Fiorino, Ann Arbor, MI (US); Dakotah Thompson, Ann Arbor, MI (US); Chang Jiang, Ann Arbor, MI (US); Rohith Mittapally, Ann Arbor, MI (US); Sunghoon Hur, Ann Arbor, MI (US)

(73) Assignee: The Regents of The University of Michigan, Ann Arbor, MI (US)

( * ) Notice: Subject to any disclaimer, the term of this patent is extended or adjusted under 35 U.S.C. 154(b) by 806 days.

(21) Appl. No.: 16/508,761

(22) Filed: Jul. 11, 2019

(65) Prior Publication Data
US 2020/0015685 A1  Jan. 16, 2020

Related U.S. Application Data

(60) Provisional application No. 62/696,874, filed on Jul. 12, 2018.

(51) Int. Cl.
| | |
|---|---|
| G01N 25/20 | (2006.01) |
| A61B 5/00 | (2006.01) |
| G01K 17/00 | (2006.01) |
| A61B 5/11 | (2006.01) |

(52) U.S. Cl.
CPC ............ *G01N 25/20* (2013.01); *A61B 5/1118* (2013.01); *A61B 5/4866* (2013.01); *G01K 17/00* (2013.01); *A61B 2503/40* (2013.01); *A61B 2562/0271* (2013.01)

(58) Field of Classification Search
USPC .................................................. 374/31, 208
See application file for complete search history.

(56) References Cited

U.S. PATENT DOCUMENTS

2020/0166417 A1 * 5/2020 McCall .................. G01K 17/04

FOREIGN PATENT DOCUMENTS

| CN | 108226220 A | * | 6/2018 |
| CN | 110646465 A | * | 1/2020 |

OTHER PUBLICATIONS

Translation of CN108226220A (Year: 2018).*
Thermal Ceramics, Microporous products: WDS Thermal conductivity of WDS Flexipor (Year: NA).*
Professional Plastics, "Thermal Properties of Plastic Materials" (Year: NA).*
The Engineering Toolbox, Thermal Conductivity of copper (Year: NA).*
Alberts, B., Wilson, J.H. & Hunt, T. Molecular biology of the cell, 5th edition. (Garland Science, New York; 2008).
Baker et al., "Diabetic larvae and obese flies-emerging studies of metabolism in *Drosophila*." Cell Metab. Oct. 2007;6(4):257-66.

(Continued)

*Primary Examiner* — Mirellys Jagan
(74) *Attorney, Agent, or Firm* — Casimir Jones S.C.; Thomas A. Isenbarger

(57) ABSTRACT

Provided herein is technology relating to measuring temperature and particularly, but not exclusively, to devices, methods, systems, and kits for doing measuring temperature at high resolution, e.g., in living organisms.

12 Claims, 45 Drawing Sheets

(56) References Cited

OTHER PUBLICATIONS

Berger et al., "Long-term C. elegans immobilization enables high resolution developmental studies in vivo." Lab Chip. May 1, 2018;18(9):1359-1368.

Bishop et al., "Two neurons mediate diet-restriction-induced longevity in C. elegans." Nature. May 31, 2007;447(7144):545-9.

Braeckman et al., "Assessing metabolic activity in aging Caenorhabditis elegans: concepts and controversies." Aging Cell. Dec. 2002;1(2):82-8.

Chancellor et al., et al. "Heat conduction calorimeter for massively parallel high throughput measurements with picoliter sample volumes." Applied physics letters 85.12 (2004): 2408-2410.

Chokshi et al., "$CO_2$ and compressive immobilization of C. elegans on-chip." Lab Chip. Jan. 7, 2009;9(1):151-7.

Chronis et al., "Microfluidics for in vivo imaging of neuronal and behavioral activity in Caenorhabditis elegans." Nat Methods. Sep. 2007;4(9):727-31.

Colman et al., "Caloric restriction reduces age-related and all-cause mortality in rhesus monkeys." Nat Commun. Apr. 1, 2014;5:3557.

Corsi et al., "A Transparent Window into Biology: A Primer on Caenorhabditis elegans." Genetics. Jun. 2015;200(2):387-407.

Deberardinis et al., "Cellular metabolism and disease: what do metabolic outliers teach us?" Cell. Mar. 16, 2012;148(6):1132-44.

Dickinson et al., "Muscle efficiency and elastic storage in the flight motor of *Drosophila*." Science. Apr. 7, 1995;268(5207):87-90.

Eckel-Mahan, K. & Sassone-Corsi, P. Metabolism and the Circadian Clock Converge. Physiology Reviews 93, 107-135 (2013).

Ferrannini "The theoretical bases of indirect calorimetry: a review." Metabolism. Mar. 1988;37(3):287-301.

Fessenden et al., "Metabolomics: Small molecules, single cells." Nature. Nov. 30, 2016;540(7631):153-155.

Fiorino et al., "Parallelized, real-time, metabolic-rate measurements from individual *Drosophila*." Sci Rep. Sep. 27, 2018;8(1):14452.

Horowitz & Hill. The art of electronics. 2nd edition, Cambridge University Press, 1989.

Houthoofd et al., "No reduction of metabolic rate in food restricted Caenorhabditis elegans." Exp Gerontol. Dec. 2002;37(12):1357-67.

Hulbert et al., "Metabolic rate is not reduced by dietary-restriction or by lowered insulin/IGF-1 signalling and is not correlated with individual lifespan in *Drosophila melanogaster*." Exp Gerontol. Aug. 2004;39(8):1137-43.

Incropera, F.P., Fundamentals of heat and mass transfer. 6th ed. 2007, Hoboken, NJ: John Wiley. TOC only.

Johannessen et al., "Heat conduction nanocalorimeter for pl-scale single cell measurements." Applied Physics Letters 80.11 (2002): 2029-2031.

Kaelin et al., "Influence of metabolism on epigenetics and disease." Cell. Mar. 28, 2013;153(1):56-69.

Kerr et al., "Mutant Kras copy number defines metabolic reprogramming and therapeutic susceptibilities." Nature. Mar. 3, 2016;531(7592):110-3.

Kleiber "Body Size and Metabolic Rate" Physiological Reviews, 1947. 27(4): p. 511-541.

Krenger et al., "Dynamic microfluidic nanocalorimetry system for measuring Caenorhabditis elegans metabolic heat." Lab Chip. May 29, 2018;18(11):1641-1651.

Lee et al., "High-sensitivity microfluidic calorimeters for biological and chemical applications." Proc Natl Acad Sci U S A. Sep. 8, 2009;106(36):15225-30.

Lighton et al., "Measuring metabolic rates: a manual for scientists" Oxford University Press, 2018. Table of Contents only.

Lin et al., "Calorie restriction extends *Saccharomyces cerevisiae* lifespan by increasing respiration." Nature. Jul. 18, 2002;418(6895):344-8.

López-Otín et al., "Metabolic Control of Longevity." Cell. Aug. 11, 2016;166(4):802-821.

Mattison et al., "Impact of caloric restriction on health and survival in rhesus monkeys from the NIA study." Nature. Sep. 13, 2012;489(7415):318-21.

Modest, Radiative Heat Transfer, 3rd edition. (Academic Press, London, England; 2013). TOC only.

Padmanabha et al., "*Drosophila* gains traction as a repurposed tool to investigate metabolism." Trends Endocrinol Metab. Oct. 2014;25(10):518-27.

Pavlova et al., "The Emerging Hallmarks of Cancer Metabolism." Cell Metab. Jan. 12, 2016;23(1):27-47.

Riera et al., "Tipping the metabolic scales towards increased longevity in mammals." Nat Cell Biol. Mar. 2015;17(3):196-203.

Rutter et al., "Metabolism and the control of circadian rhythms." Annu Rev Biochem. 2002;71:307-31.

Sadat et al., "Room temperature picowatt-resolution calorimetry." Applied Physics Letters 99.4 (2011): 043106. 1-4.

Sadat et al., "High resolution resistive thermometry for micro/nanoscale measurements." Rev Sci Instrum. Aug. 2012;83(8):084902.

Sadat et al., "Resistance thermometry-based picowatt-resolution heat-flow calorimeter." Applied Physics Letters 102.16 (2013): 163110.

Spiegelman et al., "Obesity and the regulation of energy balance." Cell. Feb. 23, 2001;104(4):531-43.

Van Voorhies "Metabolism and aging in the nematode Caenorhabditis elegans." Free Radic Biol Med. Sep. 1, 2002;33(5):587-96.

Voet, D. & Voet, J.G. Biochemistry, 4th edition. John Wiley & Sons, Hoboken, NJ; 2011. TOC only.

Walsberg et al., "Direct calorimetry reveals large errors in respirometric estimates of energy expenditure." J Exp Biol. Mar. 2005;208(Pt 6):1035-43.

Weindruch et al., "The retardation of aging in mice by dietary restriction: longevity, cancer, immunity and lifetime energy intake." J Nutr. Apr. 1986;116(4):641-54.

West et al., "Allometric scaling of metabolic rate from molecules and mitochondria to cells and mammals." Proc Natl Acad Sci U S A. Feb. 19, 2002;99 Suppl 1:2473-8.

White et al., "Mammalian basal metabolic rate is proportional to body mass2/3." Proc Natl Acad Sci U S A. Apr. 1, 2003;100(7):4046-9.

Xu et al., A microfabricated nanocalorimeter: design, characterization, and chemical calibration. Anal Chem. Apr. 15, 2008;80(8):2728-33.

Xu et al., "Regulation of feeding and metabolism by neuronal and peripheral clocks in *Drosophila*." Cell Metab. Oct. 2008;8(4):289-300.

Zenobi et al., "Single-cell metabolomics: analytical and biological perspectives." Science. Dec. 6, 2013;342(6163):1243259.

\* cited by examiner

CALORIMETER

This application claims priority to U.S. provisional patent application Ser. No. 62/696,874, filed Jul. 12, 2018, which is incorporated herein by reference in its entirety.

FIELD

Provided herein is technology relating to measuring temperature and particularly, but not exclusively, to devices, methods, systems, and kits for doing measuring temperature at high resolution, e.g., in living organisms.

BACKGROUND

Metabolism is linked to the regulation and dysfunction of complex cellular and physiological responses ranging from altered metabolic programs in cancers and aging to circadian rhythms and molecular clocks. However, the underpinning mechanisms beyond enzymatic pathway control and substrate preferences remain unclear. Metabolic studies on living organisms are needed to understand these complex physiological responses.

A number of techniques, including quantification of metabolites, respirometry, and direct calorimetric measurements, have been utilized to characterize the metabolic output and state of biological systems ranging from collections of cells to whole organisms. The strategy of quantifying metabolites, broadly speaking, is based on profiling specific, low molecular weight metabolites that, as fundamental constituents of the key biochemical pathways, serve as metabolic indicators (10, 11). But this strategy has significant limitations: (1) Destructive sample preparation prevents continuous, time-resolved measurements; and (2) relating the detected biomarkers to biological mechanisms remains challenging and uncertain (10). The second major approach, respirometry, quantifies the metabolic rate of biological systems from measured oxygen consumption or $CO_2$-production rates (12, 13). Using a flow-through experimental configuration and sensitive $CO_2$-gas analysis, time-resolved measurements from single, small model organisms like *Drosophila* are feasible (14), but this approach suffers from potentially large errors in metabolic estimates (15), may fail to properly capture switching between metabolic pathways, and is challenging to parallelize. In the final approach, direct calorimetry, the aerobic and anaerobic metabolic activity is determined from the heat production of the system (12, 16-19), which quantifies the total metabolism activity because all cellular processes (including, e.g., energy conversion, gene expression, motility) have finite efficiencies resulting in characteristic heat dissipation. However, current direct calorimetric methods lack the desired sensitivity, response time, throughput, or physiological compatibility to conduct metabolic studies from individual, small model organisms. Thus, new technologies are needed.

SUMMARY

The technology described herein relates to a high-resolution calorimeter. In some embodiments, the technology combines sensitive thermometry with optical imaging. Experiments were conducted during the development of the technology described herein to measure the basal metabolic rates of individual flies in real time. In particular, the technology was used to measure the basal metabolic rates of ten individual flies concurrently in real time with approximately 100-nW resolution. Data collected during these experiments indicated that genotype, age, and dietary restriction are associated with metabolism in adult flies. The technology described herein provides a powerful new approach for performing systematic studies of metabolic regulation related to cellular and physiological function and disease mechanisms.

As described herein, embodiments of the calorimeter technology are capable of measuring the metabolic heat output from living cells, tissues, and/or organisms (e.g., model organisms (e.g., *Drasophilia melanogaster* and *Caenorhabditis elegans*, among others)).

In contrast to conventional calorimeters that apply external heat to a sample, the calorimeter technology described herein detects heat of a sample that is generated internally, e.g., as it moves about the sample tube of the apparatus. Further, embodiments comprise an imaging component to track the organism visually while heat is measured. Moreover, embodiments of the calorimeter monitor multiple samples simultaneously, e.g., by using an plurality of sample tubes (e.g., hollow glass tubes), each of which is instrumented with a thermistor to monitor temperature as described herein.

As described herein, the calorimeter technology is highly sensitive to small temperature changes. In particular, embodiments of the calorimeter technology comprise a proportional-integral-derivative (PID) controlled bridge circuit. Accordingly, the technology minimizes the effects of electronic noise, which provides a temperature resolution of approximately 30 µK and a calorimetric resolution of approximately 100 nW. Further, embodiments provide a time sensitivity of less than 1 minute (e.g., approximately 50 seconds or fewer (e.g., 40, 35, 30, or fewer seconds)), thus providing a technology to associate metabolic activity with organism activity level, e.g., as monitored by the imaging (e.g., camera) system.

As described herein, the present technology provides related methods for measuring metabolic heat output of small biological systems (e.g., cells, tissues, organs, organisms, etc.) using a direct calorimetry approach. In some embodiments, methods measure the heat output (e.g., metabolic heat output) of a model organism or a small sample size.

In some embodiments, the technology comprises use of a device comprising sensitive thermistors and optical monitoring equipment to measure heat expenditure (e.g., in real-time). In some embodiments, the technology finds use to observe behavior associated with changes in metabolic rate. In some embodiments, systems, apparatuses, and methods described herein provide temperature readings at a resolution of approximately 30 µK (e.g., 10, 11, 12, 13, 14, 15, 16, 17, 18, 19, 20, 21, 22, 23, 24, 25, 25.5, 26, 26.5, 27, 27.2, 27.5, 28, 28.2, 28.5, 29, 29.2, 29.5, 29.7, 29.9, or 30 µK), which is more sensitive than currently available technologies, and tracks heat output at a time resolution of less than 1 minute.

The technology utilizes a suspended glass tube to monitor an organism. In some embodiments, a plurality of suspended glass tubes provides high throughput.

In some embodiments, the technology provides a calorimetry apparatus. For example, some embodiments provide a calorimetry apparatus comprising, consisting of, or consisting essentially of a single sample chamber. In some embodiments, the single sample chamber comprises a tube. In some embodiments, a sensing thermistor is thermally coupled to said tube. In some embodiments, the calorimetry apparatus further comprises a high thermal conductivity material attached to an outside surface of said tube, e.g., a high thermal conductivity material having a thermal conductivity greater than 300 W m$^{-1}$ K$^{-1}$. In some embodiments, the high thermal conductivity material comprises copper. In some embodiments, the tube is suspended on its ends. In some embodiments, the heat measured by the sensor is referenced to the temperature of the substrate that supports the tube (e.g., at the tube ends). In some embodiments, the substrate supporting the tube is maintained at a constant temperature (e.g., using temperature control as described herein). In some embodiments, the tube comprises glass. In some embodiments, the tube has a thermal conductivity of approximately 1 W m$^{-1}$ K$^{-1}$.

In some embodiments, the apparatus has a thermal conductance of approximately 2 mW/K. In some embodiments, the apparatus has a thermal conductance of approximately 1 to 5 µW/K. In some embodiments, the calorimetry apparatus detects heat at and/or is capable of detecting heat at a resolution of 100-200 pW. In some embodiments, the calorimetry apparatus detects heat at and/or is capable of detecting heat at a resolution of 50-150 nW. In some embodiments, the calorimetry apparatus detects heat at and/or is capable of detecting heat at a resolution of 10-50 µK.

In some embodiments, the calorimetry apparatus further comprises a circuit comprising said sensing thermistor. In some embodiments, the circuit comprises high thermal stability resistors. In some embodiments, the high thermal stability resistors have a rated temperature coefficient of approximately 0.2 ppm/K. In some embodiments, the circuit comprises a Wheatstone bridge. In some embodiments, the circuit comprises a high-stability resistor, a potentiometer, a shunt capacitor, and/or an instrumentation amplifier.

In some embodiments, the calorimetry apparatus further comprises an imaging system. In some embodiments, the imaging system is configured to record movement of an organism placed in said single sample chamber. In some embodiments, the circuit further comprises a reference thermistor. In some embodiments, the imaging system comprises a charge-coupled diode. In some embodiments, In some embodiments, the calorimetry apparatus further comprises an illumination sub-system. In some embodiments, the illumination sub-system comprises a light-emitting diode.

In some embodiments, the calorimetry apparatus further comprises a temperature control sub-system. In some embodiments, the temperature control sub-system comprises a heat shield, a temperature controller, a sensing thermistor, a reference thermistor, and/or a Peltier device.

In some embodiments, the calorimetry apparatus further comprises an optical window that transmits electromagnetic wavelengths of 315 nm-710 nm and absorbs infrared radiation.

Accordingly, provided herein is a calorimetry apparatus comprising a tube; a sensing thermistor; an imaging system; and a circuit to measure heat output of the biological organism. In some embodiments, the circuit of the calorimetry apparatus comprises the sensing thermistor and a reference thermistor. In some embodiments, the circuit comprises a Wheatstone bridge. In some embodiments, the circuit comprises a high-stability resistor, a potentiometer, a shunt capacitor, and/or an instrumentation amplifier. In some embodiments, the imaging system comprises a charge-coupled diode. Further, in some embodiments, the apparatus comprises an illumination sub-system, e.g., comprising a light-emitting diode. In some embodiments, the apparatus comprises a temperature control sub-system, e.g., comprising a heat shield, a temperature controller, a sensing thermistor, a reference thermistor, and a Peltier device. In some embodiments, the apparatus comprises an optical window that transmits electromagnetic wavelengths of 315 nm-710 nm and absorbs infrared radiation. In some embodiments, the calorimetry apparatus is capable of detecting heat at a resolution of 100-200 pW; is capable of detecting heat at a resolution of 50-150 nW; and/or is capable of measuring temperature at a resolution of 10-50 µK.

In related embodiments, the technology provides a method of measuring metabolic output of a biological organism. In some embodiments, methods comprise providing an apparatus comprising a tube for holding a biological organism and a thermistor attached to the tube; an imaging system to record images of the biological organism; and a circuit to measure heat output detected by the sensing thermistor; measuring metabolic heat output of the biological organism; and recording the position of the biological organism as a function of time. In some embodiments, measuring metabolic heat output of the biological organism and recording the position of the biological organism as a function of time are simultaneous. In some embodiments, methods further comprise calculating a temperature change as a function of the heat output detected by the sensing thermistor. In some embodiments, methods comprise controlling the temperature of the apparatus. In some embodiments, methods comprise measuring the metabolic output of a biological organism and simultaneously recording the activity level of said biological organism. In some embodiments, methods comprise measuring the metabolic output of a plurality of biological organisms and simultaneously recording the activity levels of said plurality of biological organisms. In some embodiments, methods comprise identifying a basal metabolic output for a biological organism at rest.

In some embodiments, methods comprise detecting heat at a resolution of 100-200 pW. In some embodiments, methods comprise detecting heat at a resolution of 50-150 nW. In some embodiments, methods comprise detecting heat at a resolution of 10-50 µK.

In additional embodiments, the technology provides systems comprising a calorimetric sub-system; an imaging sub-system; an illumination sub-system; and a temperature control sub-system. In some embodiments, the calorimetric sub-system comprises a tube to hold a biological organism and a sensing thermistor. In some embodiments, the calorimetric sub-system comprises a circuit to measure heat output of a biological organism. In some embodiments, the imaging sub-system comprises a charge-coupled diode. In some embodiments, the illumination sub-system comprises a light emitting diode. In some embodiments, the illumination sub-system comprises a light emitting diode providing visible light. In some embodiments, the temperature control sub-system comprises a heat shield, a temperature control, and/or a Peltier device. In some embodiments, the system further comprises a biological organism. In some embodiments, the system comprises a plurality of tubes to hold a plurality of biological organisms. In some embodiments, the systems comprise a microprocessor, e.g., to perform methods for determining basal metabolic heat production from heat output data; to perform methods for determining the center of mass of a biological organism, to perform methods for determining activity level from image data; etc. In some embodiments, systems comprise a microfluidic component configured to provide solutions to the biological organism.

The technology finds use in recording the metabolic output of a biological organism. Additional embodiments will be apparent to persons skilled in the relevant art based on the teachings contained herein.

BRIEF DESCRIPTION OF THE DRAWINGS

These and other features, aspects, and advantages of the present technology will become better understood with regard to the following drawings:

FIG. 1A is a schematic illustration of the calorimeter's working principle. A fly is contained at the center of a glass tube (e.g., having a 2×2 mm$^2$ inner cross section). The high-sensitivity thermistor 102 detects the small temperature increase, $\Delta T_{sense}$, due to the fly's heat output 107, $q_{metabolic}$. The thermal conductance of the glass tube, $G_{tube}$, is the primary pathway for heat transfer as shown in the thermal resistance network. FIG. 1B shows a rendering of an embodiment of the system comprising a calorimetric sub-system comprising a plurality of glass tubes 101 and thermistors 102 and optical imaging sub-system 103. Two independently-controlled sets of Peltier modules 112 maintain the temperature of the inner thermal shield 105 and outer thermal shield 106. Two CCD cameras 108 optically image the ten measurement chambers. All ten flies breathe air from a temperature-controlled, humidified air reservoir (see Methods). FIG. 1C shows a detailed view of selected calorimeter tubes 101 with a sensing thermistor 102 for measuring $\Delta T_{sense}$ and a heating thermistor 110 for calibrating the conductance ($G_{tube}$) relative to the matching thermistor 111 (see Methods). In some embodiments, copper tape (e.g., a copper plate attached to the outside surface of the tube) provides control of thermal conditions at the center of the tube (e.g., to provide isothermal conditions).

FIG. 2A shows time trace plots of the speed of locomotion (upper panel) and heat production (lower panel) of a single Canton-S fly (female, 3 days after eclosion) over the course of 300 minutes of data collection during an experiment. The dashed line in the upper panel delineates a 4 mm/minute threshold for defining the rest state. The lower dashed line in the bottom panel sets a threshold for the heat production trace for which the rest condition was met. In particular, the lower dashed line of the lower panel indicates the average basal heat production while the upper, dashed-dotted line of the lower panel represents the total average heat production for this fly. FIG. 2B shows plots of heat production as a function of activity level for the same single Canton-S fly that produced the data shown in FIG. 2A. The dashed vertical line indicates the threshold for the rest condition. FIG. 2C is a plot of heat production data for a population of 50 individual Canton-S flies averaged during periods of high (>50 mm/minute) and low (<4 mm/minute) activity. The horizontal line represents the mean for a sample. Box boundaries indicate the standard error of the mean, and error bars represent the standard deviation of the sample. The open circles to the left of the boxes signify the average heat production for the individual flies. *** p<0.001. FIG. 2D is a series of plots showing heat production data for ten flies (A-J) collected during a single experiment. Fly F is the fly for which data are shown in FIG. 2A and FIG. 2B.

FIG. 3A is a plot of basal heat production as measured for the three *Drosophila* genotypes: Canton-S, $w^{1118}$, and yw. The plots show the mean (horizontal line), standard error (box), and standard deviation (error bars). The open circles to the left of the boxes represent the average basal heat production for individual flies and N indicates the sample size. FIG. 3B shows a plot that is similar to the plot shown in FIG. 3A, except the data are normalized by fly mass (see also FIG. 8A to FIG. 8C). FIG. 3C shows a plot that is similar to the plot shown in FIG. 3A, except the data were collected for Canton-S flies 10, 20, 30, and 40 or more days past eclosion. The data indicated a marked decrease in heat production in the oldest flies. FIG. 3D shows a plot that is similar to the plot shown in FIG. 3C, except the data are normalized by fly mass. FIG. 3E shows a plot that is similar to the plots shown in FIG. 3A and FIG. 3C, except the data were collected for flies on high calorie (HCD), normal (ND), and restricted diets (RD). FIG. 3F shows a plot that is similar to the plot shown in FIG. 3E, except the data are by fly mass. ANOVA results are indicated on each panel; Tukey's tests are indicated pairwise: * p<0.01,  p<0.005, * p<0.001.

FIG. 4A shows a schematic of an embodiment of a calorimeter system comprising a glass capillary tube suspended across a cavity and a miniature thermistor integrated into the capillary tube. Data collected from the calorimeter system indicates that the technology provides high-resolution temperature measurements. The inset shows the cross-section of the capillary.

FIG. 4B is an optical image of the capillary tube and the thermistors. The top inset shows an optical image of the thermistor mounted on the capillary tube. The width of the capillary tube is approximately 100 μm). FIG. 4C show experimental data indicating that the calorimeter system measures heat with a 250-pW resolution, e.g., the data indicate that temperature changes corresponding to heat currents as small as 250 pW are detected. FIG. 4D shows images of a *C. elegans* in a 50-μm capillary tube filled with M9 buffer (top panel) and a *D. melanogaster* in a 2 mm×2 mm capillary (bottom panel).

FIG. 8A shows time trace plots of the speed of locomotion (upper panel) and heat production (lower panel) of a single $w^{1118}$ fly over the course of 300 minutes of data collection during an experiment. The dashed line in the upper panel delineates a 4 mm/minute threshold for defining the rest state. The lower dashed line in the bottom panel sets a threshold for the heat production trace for which the rest condition was met. In particular, the lower dashed line of the lower panel indicates the average basal heat production while the upper, dashed-dotted line of the lower panel represents the total average heat production for this fly. FIG. 8B shows a plot of heat production as a function of activity level for the same single fly that produced the data shown in FIG. 8A. The dashed vertical line indicates the threshold for the rest condition. FIG. 8C shows time trace plots of the speed of locomotion (upper panel) and heat production (lower panel) of a single yw fly over the course of 300 minutes of data collection during an experiment. The dashed line in the upper panel delineates a 4 mm/minute threshold for defining the rest state. The lower dashed line in the bottom panel sets a threshold for the heat production trace for which the rest condition was met. In particular, the lower dashed line of the lower panel indicates the average basal heat production while the upper, dashed-dotted line of the lower panel represents the total average heat production for this fly. FIG. 8D shows a plot of heat production as a function of activity level for the same single fly that produced the data shown in FIG. 8C. The dashed vertical line indicates the threshold for the rest condition.

FIG. 9A is a plot showing fly masses measured for flies having three Drosophila genotypes (Canton-S, $w^{1118}$, and yw). All flies were female. The mean, standard error of the mean, and standard deviation for each genotype are indicated by a horizontal line, box, and error bars, respectively. N represents the sample size. FIG. 9B is a plot showing fly masses measured for female Canton-S flies at times of 10, 20, 30 or 40 or more days past eclosion. FIG. 9C is a plot showing fly masses measured for female Canton-S flies entrained on high-calorie diet (HCD), normal diet (ND), or restricted (RD) diet. Surprisingly, flies fed on a HCD weigh less than those entrained on ND.

FIG. 10A shows average basal heat production plotted against fly mass for Canton-S, $w^{1118}$, and yellow-white (yw) flies from FIG. 3A, FIG. 3B, and FIG. 9A. FIG. 10B shows average basal heat production plotted against fly mass for the Canton-S flies from FIG. 3C, FIG. 3D, and FIG. 9B. FIG. 10C shows average basal heat production plotted against fly mass for the Canton-S flies entrained on different diets from FIG. 3E, FIG. 3F, and FIG. 9C. The plots indicate that the heat production for the flies in the samples does not exhibit straightforward allometric scaling.

FIG. 11A is a schematic of a calorimetric tube used to measure heat output while monitoring C. elegans activity. The inset shows a microscope image of C. elegans during heat output measurement. FIG. 11B is an exploded view of shields (top) and overall experimental schematics (bottom). Three shields (outer, middle, and inner) are assembled to improve temperature stability to 100 μK. In the experimental schematics, the fluidic channel is connected from reservoir to syringe pump and shields are mounted to a microscope stage for imaging. FIG. 11C shows an embodiment of the technology for compensating for environmental temperature drift by using matching calorimetry. Temperature resolution is improved through a differential scheme that subtracts environmental temperature from calorimeter temperature. FIG. 11D shows plots of data for 24-hour temperature signals from the calorimeter, environmental temperature, and differential temperature signal. Differential temperature attenuated to ±10 μK over 24 hours. The shaded box region is shown in detail in the top plot, which indicated that the differential temperature attenuated to ±4 μK over 2 hours. FIG. 11E is a plot showing thermal conductance measurement. Thermal conductance increases from 25 μW/K to 31 μW/K as flow rate increased to 200 nL/min. The inset shows an 8-μK noise floor of a calorimeter. FIG. 11F is a plot showing the time constant of the measurement chamber. When power is applied to the thermistor (red line), the temperature signal (blue line) follows a single order response and the time constant is approximately 1 minute. FIG. 11G is a plot showing thermal resolution verification. The temperature signal (blue curve) accurately follows stepwise change of applied power (red line) with a 250-pW increment.

FIG. 12A is a schematic showing a procedure to measure heat output form *C. elegans*. The temperature signal is very stable before loading and after unloading, which confirms that the calorimeter signal is robust and stable. Purple colored region is the load/unload cycle and orange colored region is the measurement region. Blue box region in measurement is shown in FIG. 12B. FIG. 12B shows the temperature signal (red line) and the quantified *C. elegans* activity rate (blue line). This signal is from blue dashed region in FIG. 12A. The data indicate that the temperature signal and activity rate are correlated. Due to a thermal time constant of the calorimeter, the temperature signal and activity signal are best correlated (correlation constant=approximately 0.82) with a 2-minute delay. FIG. 12C shows metabolic heat output rates for individual developmental stages of *C. elegans*. The metabolic rate varies from 4 nW to 100 nW as a function of development stage from L1 to adult. FIG. 12D shows the relationship between *C. elegans* body size and metabolic heat output. The data supports Kleiber's law of an exponent factor of ¾. FIG. 12E is a series of plots comparing the metabolic heat output and metabolic heat density as *C. elegans* ages. Metabolic heat output (upper red block) becomes stable or decreases from adult day 2. On the other hand, metabolic heat density (lower green block) decreases from adult day 1.

Figure 1A:
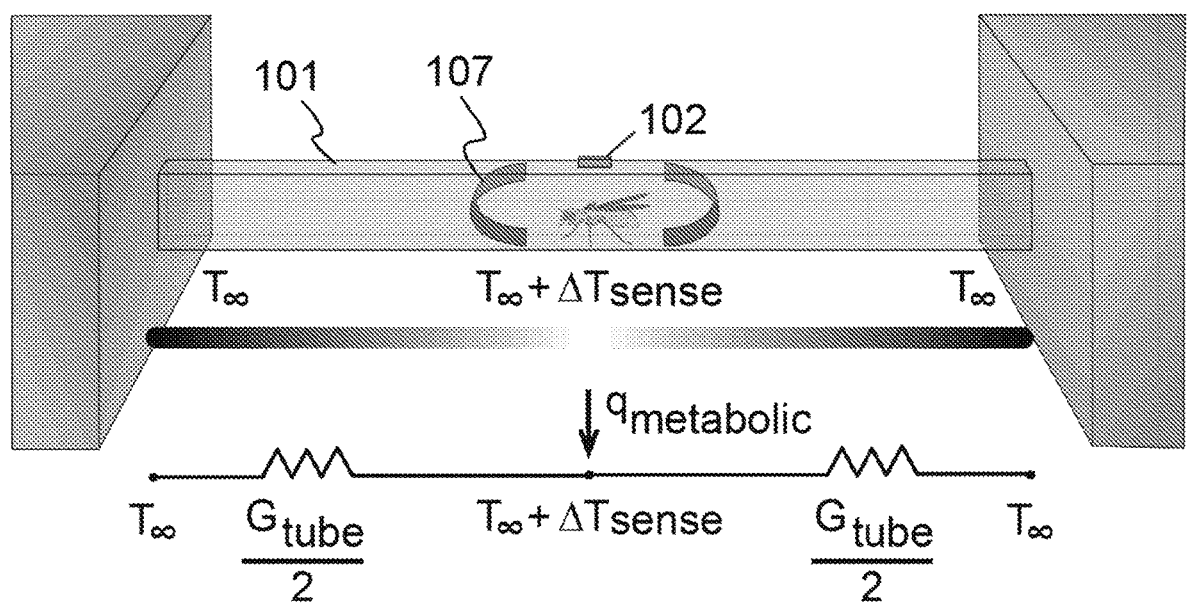
FIG. 1A, FIG. 1B, and FIG. 1C are schematic drawings of an embodiment of the calorimetric technology as described herein.

It is to be understood that the figures are not necessarily drawn to scale, nor are the objects in the figures necessarily drawn to scale in relationship to one another. The figures are depictions that are intended to bring clarity and understanding to various embodiments of apparatuses, systems, and methods disclosed herein. Wherever possible, the same reference numbers will be used throughout the drawings to refer to the same or like parts. Moreover, it should be appreciated that the drawings are not intended to limit the scope of the present teachings in any way.

DETAILED DESCRIPTION

Calorimetry was developed in the late 1700s and the bomb calorimeter was developed in the 1900s. In a conventional bomb calorimeter, a reaction takes place within a contained "bomb" that is surrounded by a water jacket—heat is transferred from the bomb to the water and the resulting change in water temperature is measured. The present technology is similar to conventional calorimeter, except that the heat is produced by a biological system or organism (e.g., within a glass sample tube) rather than from ignition and/or adding a substance to initiate a reaction. Further, in contrast to conventional calorimetric devices that measure external heat (e.g., from the bomb) to a sample (e.g., the water jacket), the present technology directly measures heat generated internally. In some embodiments, the technology further comprises use of a camera to monitor the activity level of the sample organism.

In particular, conventional isothermal titration calorimetry (ITC) for quantifying the heat of reaction from a small volume of solution uses a calorimeter consisting of two identical chambers (a reaction chamber and a reference chamber). These two chambers are contained within a thermally insulating jacket that is held at a fixed temperature. A known volume of a reacting solution is injected into the reaction chamber and an equal volume of a buffer solution is injected into the reference chamber. The heat evolved in the reaction chamber is quantified based on the amount of heat that must be actively supplied from an external source to the reference chamber to maintain the same temperature in both chambers during the course of the reaction. Each chamber is outfitted with appropriate temperature sensors and heaters (e.g., Peltier devices), which allows the temperatures of the two chambers to be equalized (e.g., using a PID control strategy).

Embodiments of the calorimeter provided herein (e.g., FIG. 1) are conceptually and structurally different from conventional ITC. Specifically, the present technology comprises a single chamber instead of two chambers. In particular, embodiments of the calorimeter described herein comprise or consist of a single chamber (e.g., a suspended tube). In some embodiments, the single chamber is supported at each end. In some embodiments, the calorimeter finds use in measuring the heat output by a biological specimen. Accordingly, in some embodiments, a biological specimen or a reaction volume is placed in the center of the suspended tube comprising a temperature sensor to detect temperature changes due to the heat generated by the specimen. The temperature rise measured by this sensor is referenced to the temperature of the substrate that supports the tube, which is maintained at a constant temperature using a custom-built temperature controller (e.g., a feedback circuit as described herein).

Accordingly, the present technology is based on a major fundamental difference with respect to conventional ITC: while an ITC instrument is operated such that there is no temperature gradient between the reaction chamber and the reference chamber, the present calorimeter technology operates such that necessarily a temperature gradient exits between the suspended tube (e.g., the center of the tube) and the substrate that supports it (see, e.g., FIG. 1). In some embodiments described herein, the calorimeter comprises a tube that is long, thin-walled, and comprising a low-thermal conductivity material to maximize the temperature gradient along its length.

Accordingly, embodiments of the calorimeter have an improved (e.g., much lower) thermal conductance relative to state-of-the-art isothermal titration calorimeters (ITCs). The present technology thus provides an improved resolution of heat flow. Further, in some embodiments, the calorimetric technology provided herein comprises lateral confinement and/or real-time imaging of a biological specimen so that all specimen motion is restricted to one dimensional motion. Thus, in some embodiments, the combination of real-time imaging and lateral confinement provides a technology that associates heat production to the activity of the sample and/or organism, which is not a feature of current ITCs.

Accordingly, provided herein is a technology related to a high-resolution calorimeter. In some embodiments, the calorimeter is capable of simultaneous metabolic heat output measurements and correlated optical observations. During the development of embodiments of the technology, experiments were conducted in which the technology was used to obtain metabolic heat output and optical observations from fruit flies (*Drosophila melanogaster*) in real-time. Data were collected in these experiments using *Drosophila* because *Drosophila* has recently emerged as an important model system in metabolic research (20-22) due to having shared metabolic pathways with mammals (21) and the relative ease with which the *Drosophila* genome can be manipulated. In some embodiments, the calorimeter technology provided herein comprises two components: 1) a calorimetric subsystem comprising a glass tube (VitroCom S102) and a sensitive thermistor; and 2) an optical imaging sub-system. See, e.g., FIG. 1. In particular embodiments, the calorimeter component (e.g., the glass tube) provides an experimental chamber to hold a biological organism (e.g., a single fly) and the optical imaging system tracks the movement of the biological organism (e.g., the single fly) in real time. In some embodiments, the calorimeter technology comprises a plurality of glass tubes and the device is capable of measuring temperature of multiple samples in parallel.

In this detailed description of the various embodiments, for purposes of explanation, numerous specific details are set forth to provide a thorough understanding of the embodiments disclosed. One skilled in the art will appreciate, however, that these various embodiments may be practiced with or without these specific details. In other instances, structures and devices are shown in block diagram form. Furthermore, one skilled in the art can readily appreciate that the specific sequences in which methods are presented and performed are illustrative and it is contemplated that the sequences can be varied and still remain within the spirit and scope of the various embodiments disclosed herein.

All literature and similar materials cited in this application, including but not limited to, patents, patent applications, articles, books, treatises, and internet web pages are expressly incorporated by reference in their entirety for any purpose. Unless defined otherwise, all technical and scientific terms used herein have the same meaning as is commonly understood by one of ordinary skill in the art to which the various embodiments described herein belongs. When definitions of terms in incorporated references appear to differ from the definitions provided in the present teachings, the definition provided in the present teachings shall control. The section headings used herein are for organizational purposes only and are not to be construed as limiting the described subject matter in any way.

Definitions

To facilitate an understanding of the present technology, a number of terms and phrases are defined below. Additional definitions are set forth throughout the detailed description.

Throughout the specification and claims, the following terms take the meanings explicitly associated herein, unless the context clearly dictates otherwise. The phrase "in one embodiment" as used herein does not necessarily refer to the same embodiment, though it may. Furthermore, the phrase "in another embodiment" as used herein does not necessarily refer to a different embodiment, although it may. Thus, as described below, various embodiments of the invention may be readily combined, without departing from the scope or spirit of the invention.

In addition, as used herein, the term "or" is an inclusive "or" operator and is equivalent to the term "and/or" unless the context clearly dictates otherwise. The term "based on" is not exclusive and allows for being based on additional factors not described, unless the context clearly dictates otherwise. In addition, throughout the specification, the meaning of "a", "an", and "the" include plural references. The meaning of "in" includes "in" and "on."

As used herein, the terms "about", "approximately", "substantially", and "significantly" are understood by persons of ordinary skill in the art and will vary to some extent on the context in which they are used. If there are uses of these terms that are not clear to persons of ordinary skill in the art given the context in which they are used, "about" and "approximately" mean plus or minus less than or equal to 10% of the particular term and "substantially" and "significantly" mean plus or minus greater than 10% of the particular term.

As used herein, the suffix "-free" refers to an embodiment of the technology that omits the feature of the base root of the word to which "-free" is appended. That is, the term "X-free" as used herein means "without X", where X is a feature of the technology omitted in the "X-free" technology. For example, a "calcium-free" composition does not comprise calcium, a "sequencing-free" method does not comprise a sequencing step, etc.

As used herein, an "increase" or a "decrease" refers to a detectable (e.g., measured) positive or negative change in the value of a variable relative to a previously measured value of the variable, relative to a pre-established value, and/or relative to a value of a standard control. An increase is a positive change preferably at least 10%, more preferably 50%, still more preferably 2-fold, even more preferably at least 5-fold, and most preferably at least 10-fold relative to the previously measured value of the variable, the pre-established value, and/or the value of a standard control. Similarly, a decrease is a negative change preferably at least 10%, more preferably 50%, still more preferably at least 80%, and most preferably at least 90% of the previously measured value of the variable, the pre-established value, and/or the value of a standard control. Other terms indicating quantitative changes or differences, such as "more" or "less," are used herein in the same fashion as described above.

As used herein, a "system" denotes a set of components, real or abstract, comprising a whole where each component interacts with or is related to at least one other component within the whole.

Description

Metabolism is the sum of all physical and biochemical processes in living organisms that either produce or consume energy (1, 2). As part of regular metabolic activity, cells and organisms constantly replenish their energy supply through complex metabolic pathways (e.g., the uptake and breakdown of nutrients, cellular respiration, etc.), resulting in a diverse set of reaction intermediates and products ("metabolites"). Since energy input is essential, metabolic processes are involved in virtually all cellular processes and provide an integrative signature of cellular and organismal activity (1, 2). Moreover, significant evidence indicates that various common human diseases such as cancer (3, 4), obesity (5), diabetes (6), and aging (7, 8) involve abnormal metabolic states. Therefore, obtaining insights into the regulation of metabolism in vivo (e.g., including by not limited to cells and individual organisms) is important for understanding the overall functioning of cells and cellular mechanisms and facilitates the development of new approaches to treating metabolism-linked diseases (9).

Accordingly, provided herein is technology for making direct measurements of the basal metabolic rate in vivo (e.g., in a cell or organism). Experiments were conducted using the technology to measure metabolic outputs of a model organism (e.g., *Drosophila melanogaster*). Embodiments of the technology are capable of performing concurrent measurements on multiple individual organisms for improved throughput. The technology finds use in systematic studies of the effects of diet and gene expression on metabolism and in studies for clarifying the link between metabolism and lifespan and aging. In some embodiments, the technology finds use in performing long-term studies of circadian biology (36, 37) by integrating food and environmental stimuli into the apparatus. Finally, in some embodiments, the technology finds use for studying model organisms (e.g., *Drosophila, C. elegans*, Zebra fish embryos, etc.) to address key questions regarding aging, metabolism, and disease.

Although the disclosure herein refers to certain illustrated embodiments, it is to be understood that these embodiments are presented by way of example and not by way of limitation.

Calorimetry Apparatus

In some embodiments, the technology provided herein relates to a calorimeter device. See, e.g., FIG. 1. In some embodiments, the calorimeter comprises two components: 1) a calorimetric sub-system comprising a tube 101 and a sensing thermistor 102; and 2) an imaging sub-system 103. The tube is not limited in shape or length (e.g., while some embodiments comprise a tube with a circular cross-section, the tube may have any cross-section, e.g., oval, polygonal, etc.) In some embodiments, the imaging sub-system and tube are chosen so that a sample (e.g., a living cell, organism, etc.) in the tube is imaged by the imaging sub-system (e.g., to measure the position, movement, and/or activity level of the sample in the tube). For example, embodiments comprise a tube that is transparent to visible light and the imaging sub-system is a visible light imaging sub-system. Thus, in some embodiments, the tube is made from a visibly transparent material such as, but not limited to, glass, plastic, quartz, etc. In some embodiments, the tube comprises a material having a thermal conductivity of approximately 1 W m$^{-1}$ K$^{-1}$ (e.g., approximately 0.1 to 5.0 W m$^{-1}$ K$^{-1}$ (e.g., 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, or 5.0, W m$^{-1}$ K$^{-1}$)).

In some embodiments, a material having a high thermal conductivity is attached to the outside of the surface of the tube. For instance, in some embodiments a copper plate or tape is attached to the outside of the surface of the tube (e.g., glass tube). In some embodiments, the material (e.g., copper plate) has a high thermal conductivity that is greater than approximately 300 W m$^{-1}$ K$^{-1}$ (e.g., greater than 300, 310, 320, 330, 340, 350, 360, 370, 380, 390, 400, 450, 500, 550, 600, 650, 700, 750, 800, 850, 900, 950, or 1000 W m$^{-1}$ K$^{-1}$). In some embodiments, the material (e.g., copper plate) has a high thermal conductivity that is less than approximately 1000 W m$^{-1}$ K$^{-1}$.

In some embodiments, the imaging system is an X-ray imaging system and the tube is transparent to X-rays. In some embodiments, the imaging system is an infrared imaging system and the tube is transparent to infrared electromagnetic radiation. Similarly, embodiments comprise tubes transparent to other non-visible electromagnetic radiation (e.g., ultraviolet light, radio waves, gamma rays, and microwaves) and imaging sub-systems for detecting and/or recording the non-visible electromagnetic radiation. Further examples of imaging technologies that find use in the imaging sub-system include, but are not limited to, radiography, magnetic resonance imaging, PET, SPECT, ultrasound, and other medical imaging technologies. Embodiments comprise use of a tube that is appropriate for the chosen medical imaging technology.

In some embodiments, the imaging sub-system comprises an imaging component, e.g., a charge-coupled diode (CCD) imaging component. In some embodiments, the imaging sub-system comprises an intensified charge coupled device (ICCD), an electron-multiplying charge coupled device (EM-CCD), a complementary metal-oxide-semiconductor (CMOS), a photomultiplier tube (PMT), an avalanche photodiode (APD), and/or another detector capable of detecting the position, movement, and/or activity level of a sample in the tube.

In some embodiments, the imaging sub-system further comprises a source of illumination. In some embodiments, the source of illumination is chosen to produce electromagnetic radiation of an appropriate wavelength that does not affect the readings of the calorimetric sub-system (e.g., comprising the tube and thermistor). In some embodiments, the illumination power density is chosen so that the illumination does not affect the readings of the calorimetric sub-system. In some embodiments, the illumination wavelength is in the range of approximately 315 nm-710 nm. In some embodiments, the power density is approximately 0.5 nW/cm$^2$ to 50 µW/cm$^2$ (e.g., 0.5; 1; 2; 5; 10; 20; 50; 100; 200; 500; 1000; 2000; 5000; 10,000; 20,000; or 50,000 nW/cm$^2$). In some embodiments, the calorimeter device comprises an optical window that blocks infrared radiation.

In some embodiments, the sensing thermistor of the calorimetric sub-system is a high-sensitivity thermistor, e.g., a thermistor that is capable of detecting a small temperature increase from the small heat output of a living cell or organism.

Figure 5:
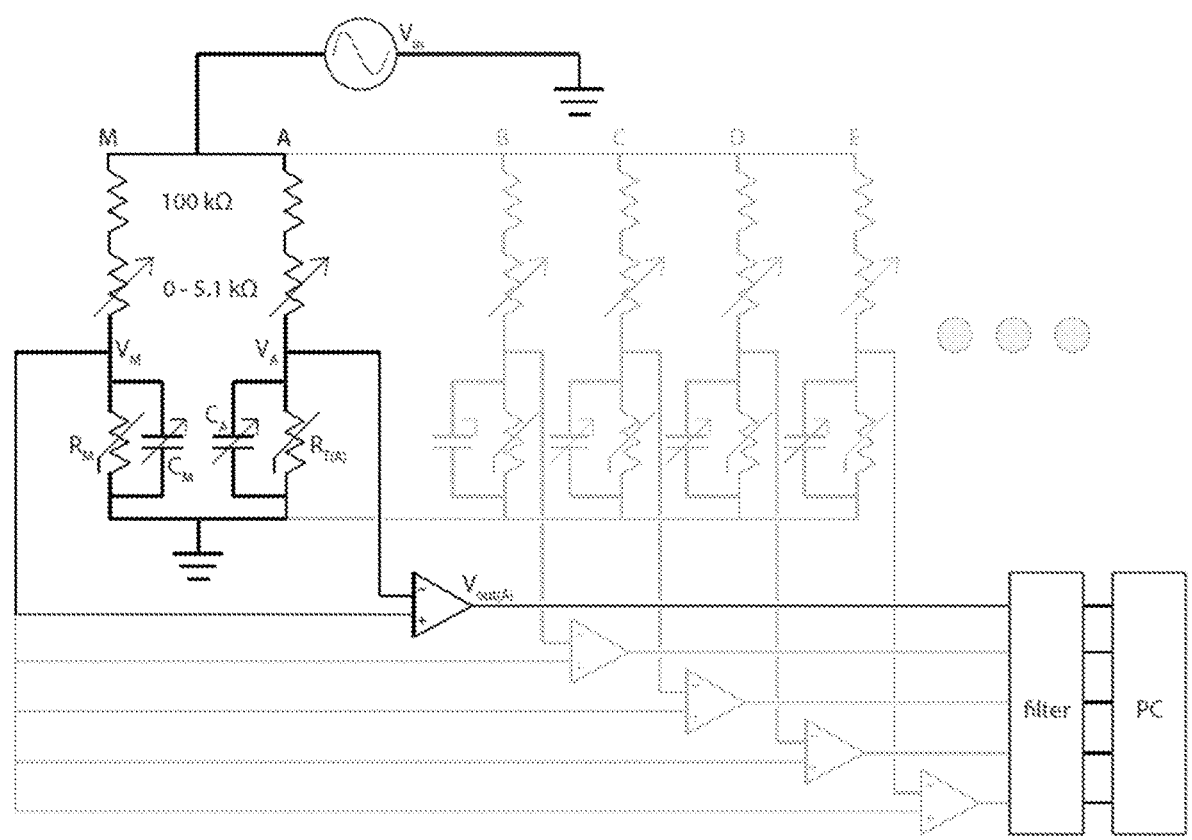
FIG. 5 shows a circuit schematic of an AC (alternating current)-driven Wheatstone bridge circuit for differential resistive thermometry (FIG. 5). The circuit comprises a sensing thermistor to measure resistance $R_T$ and a reference (matching) thermistor to measure resistance $R_M$. The circuit comprises a voltage source (e.g., providing a 200-mV rms voltage at 19.9 Hz using a waveform generator (Agilent 33210A)), high-stability (e.g., approximately ±2 ppm/K) 100-kΩ fixed resistors (Vishay Foil Resistors S Series), and stable (e.g., approximately ±20 ppm/K) potentiometers (TT Electronics/BI Model 7280 Series) with a resistance of 5.1 kΩ connected in series with the fixed resistors. Further, the phase difference between $V_M$ and $V_A$ was matched using shunt capacitors $C_M$ and $C_A$. The circuit comprises an instrumentation amplifier (Analog Devices AD524) that amplifies $V_B$ (e.g., using a gain of 100) before it was filtered using a custom-built 6-pole low pass Butterworth filter. Nine additional half-bridge legs are connected in parallel and referenced to the matching thermistor leg so that all ten signals were recorded independently using one circuit.

In some embodiments, the calorimetric device comprises a circuit to measure small temperature changes detected by the sensing thermistor, e.g., by differential resistive thermometry (see FIG. 5). In some embodiments, the calorimetric device comprises a Wheatstone bridge comprising the high-sensitivity thermistor and a reference thermistor. In some embodiments, the Wheatstone bridge is driven by an AC current (e.g., provided by a waveform generator). In some embodiments, the Wheatstone bridge comprises high-stability (e.g., approximately ±2 ppm/K) resistors (e.g., approximately 100 kΩ) to stabilize the circuit to minimize and/or eliminate sensitivity of the Wheatstone bridge voltage to temperature changes of the circuit. In some embodiments, the circuit comprises one or more potentiometers (e.g., approximately ±20 ppm/K) to balance voltage amplitudes at the operating temperature. In some embodiments, the circuit comprises one or more shunt capacitors to minimize the phase difference between voltages. In some embodiments, the circuit comprises an instrumentation amplifier to determine the voltage difference between the sensing thermistor and the reference thermistor (e.g., to provide a measurement of heat output by the living cell and/or organism).

In some embodiments, the technology provides an apparatus comprising a plurality of calorimetric sub-systems (e.g., each comprising a tube and a Wheatstone half-bridge comprising a sensing thermistor as described above (e.g., comprising resistors to stabilize the circuit to minimize and/or eliminate sensitivity of the Wheatstone bridge voltage to temperature changes of the circuit; one or more potentiometers (e.g., approximately ±20 ppm/K) to balance voltage amplitudes at the operating temperature; one or more shunt capacitors to minimize the phase difference between voltages; and an instrumentation amplifier to determine the voltage difference between the sensing thermistor and the reference thermistor)). In some embodiments, the plurality of calorimetric sub-systems provides a plurality of measurements. In some embodiments, the output signals of one or more instrumentation amplifiers is/are filtered (e.g., using a 6-pole low pass Butterworth filter). In some embodiments, the voltage output by each calorimetric sub-system is recorded independently. In some embodiments, the amplified and filtered signal(s) is/are recorded (e.g., using software (e.g., LabView)) and post-processed (e.g., by a Fast Fourier Transform-based lock-in technique).

Figure 1B:
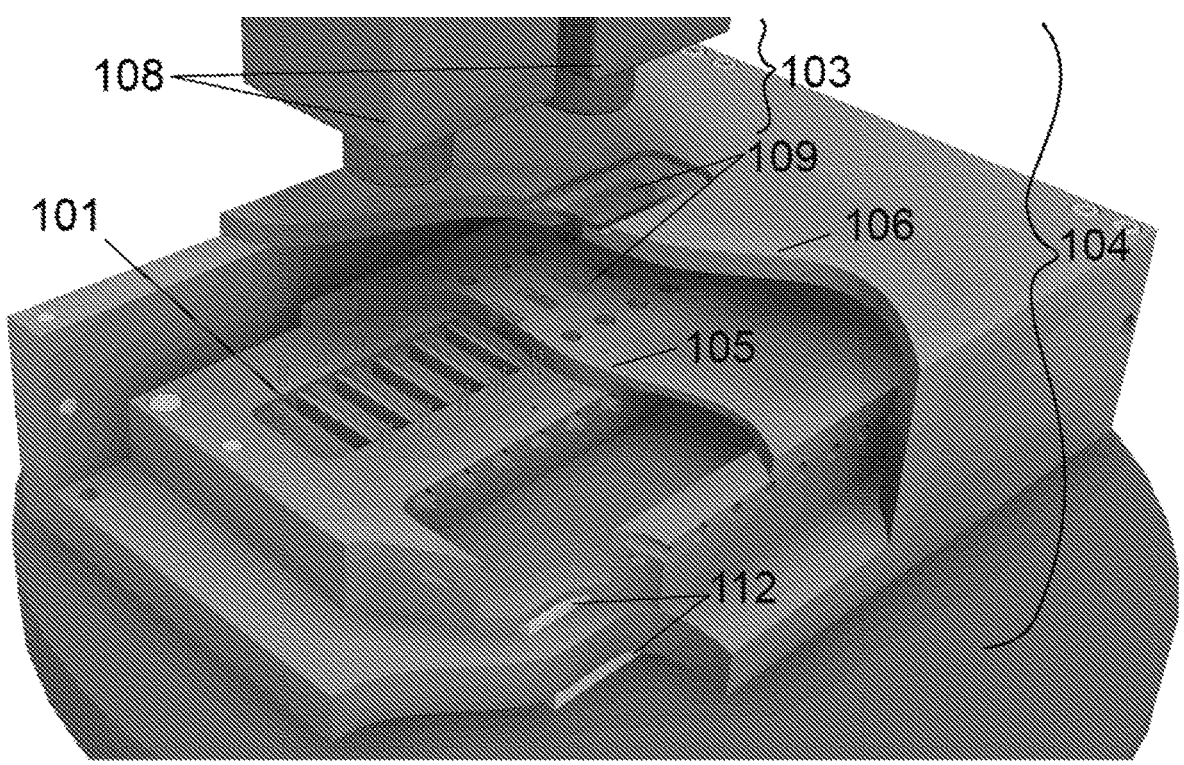
Figure 1C:
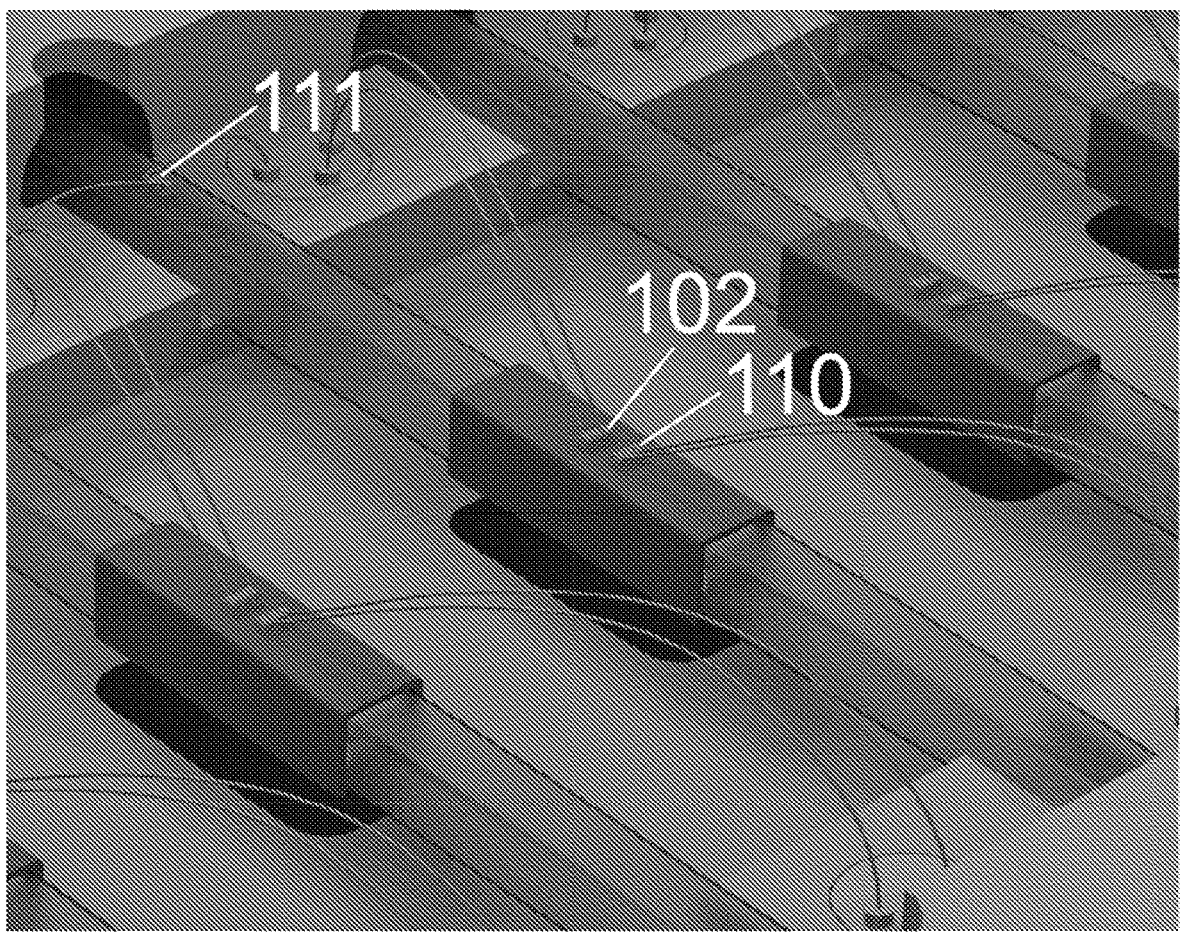

In some embodiments, the calorimetric device comprises a temperature control sub-system. In some embodiments, the temperature control sub-system comprises one or more thermal shields (e.g., an inner thermal shield and an outer thermal shield as shown in FIG. 1b). In some embodiments, the outer thermal shield comprises is made of a material having a high thermal conductivity (e.g., greater than 200

W/mK). In some embodiments, the outer thermal shield is made from a material comprising copper, silver, gold, or aluminum. In some embodiments, the outer thermal shield comprises a temperature controller and a thermistor bonded to the thermal shield. In some embodiments, the outer thermal shield comprises one or more components to heat and/or cool the calorimetric device. In some embodiments, the outer thermal shield comprises one or more Peltier modules. In some embodiments, the temperature controller receives feedback from the thermistor and the controller heats and/or cools the outer thermal shield by driving current through one or more Peltier modules. In some embodiments, the Peltier modules are in thermal contact with a heat sink.

Figure 7:
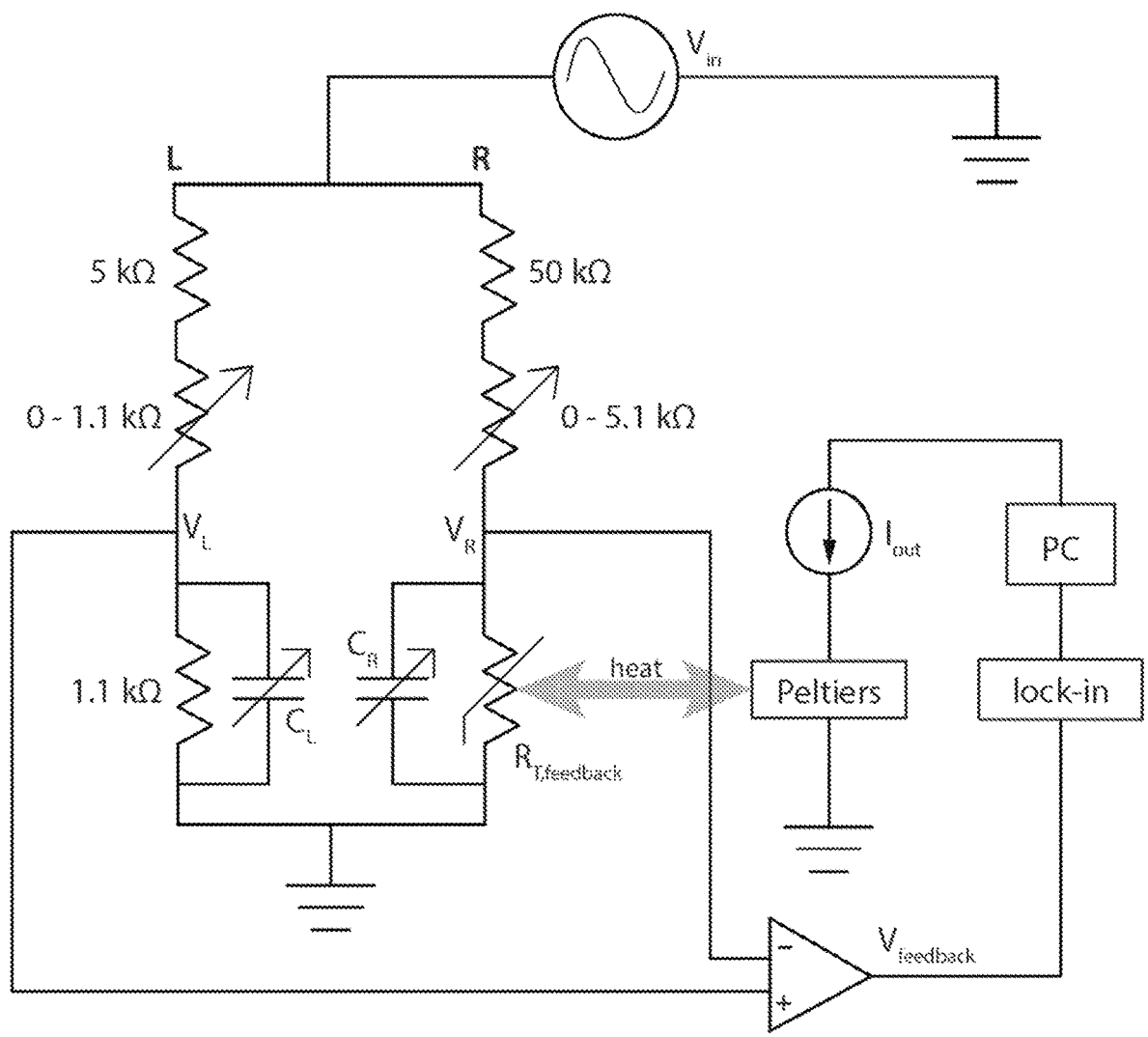
FIG. 7 is a circuit schematic showing a Wheatstone bridge for controlling the temperature of the inner shield using high-resolution temperature measurement from a feedback thermistor and a custom control scheme. A thermistor (US Sensor Corp. USP12838) was permanently bonded into the inner shield using epoxy (3M Scotch-Weld Epoxy Adhesive 2216 B/A and incorporated with three fixed resistors into the Wheatstone bridge circuit. The circuit comprises a 1-V rms voltage source at 37.5 Hz (Hewlett Packard 33120A) and the amplitudes and phases of $V_L$ and $V_R$ were balanced when the thermistor was set at 296 K by tuning series potentiometers (TT Electronics/BI Model 7280 Series) and shunt capacitors $C_L$ and $C_R$ (TDK FK Series) in the same manner as for the circuit shown in FIG. 5. The circuit comprises an instrumentation amplifier (Analog Devices AD524) to perform the difference operation and amplify the AC signal and a lock-in amplifier (Stanford Research Systems Model SR830). A MATLAB-scripted PID controller, which read the bridge voltage from the lock-in and drove a current through four Peltier modules (Laird Technologies 56590-502), was connected in series using a commercial current source (Keithley Instruments 6221). This scheme maintained a stable inner shield temperature to within ±100 μK (see, e.g., FIG. 6A).
Figure 8A:
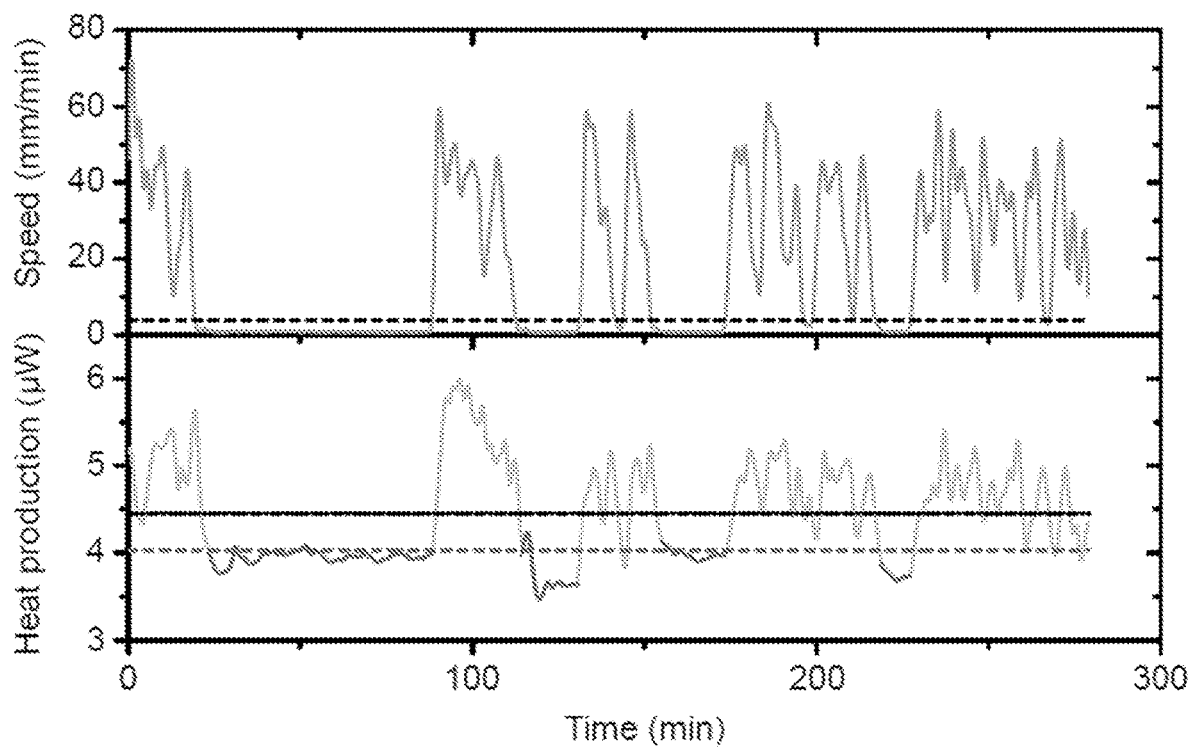
FIG. 8A to FIG. 8D are plots related to metabolic measurement data recorded for $w^{1118}$ (FIG. 8A and FIG. 8B) and yellow-white (yw) (FIG. 8C and FIG. 8D) flies using embodiments of the technology described herein.
Figure 8B:
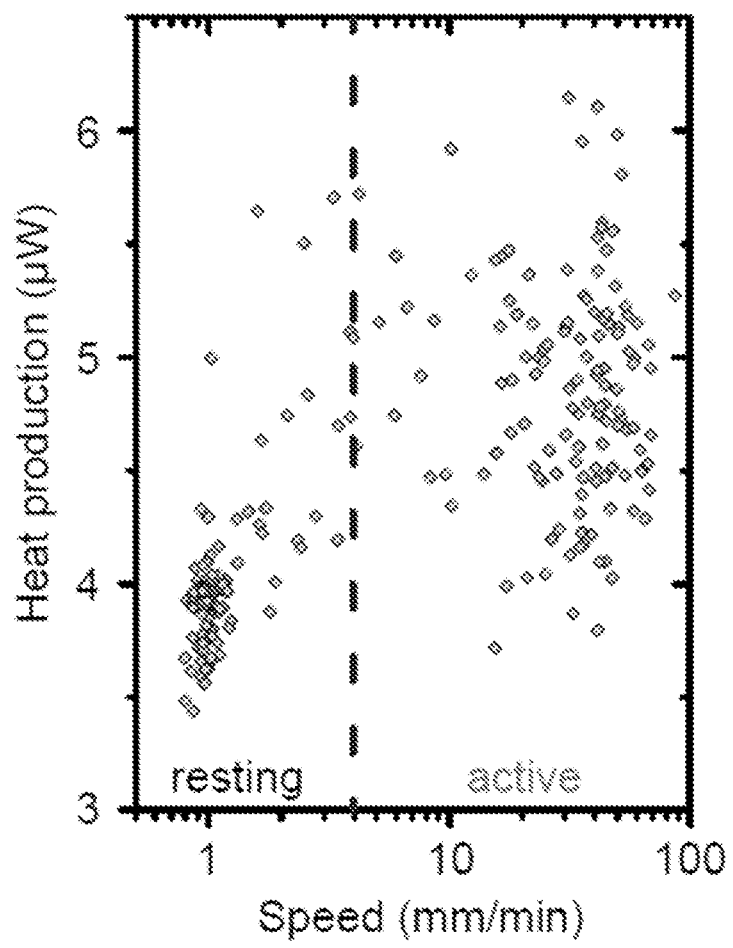
Figure 8C:
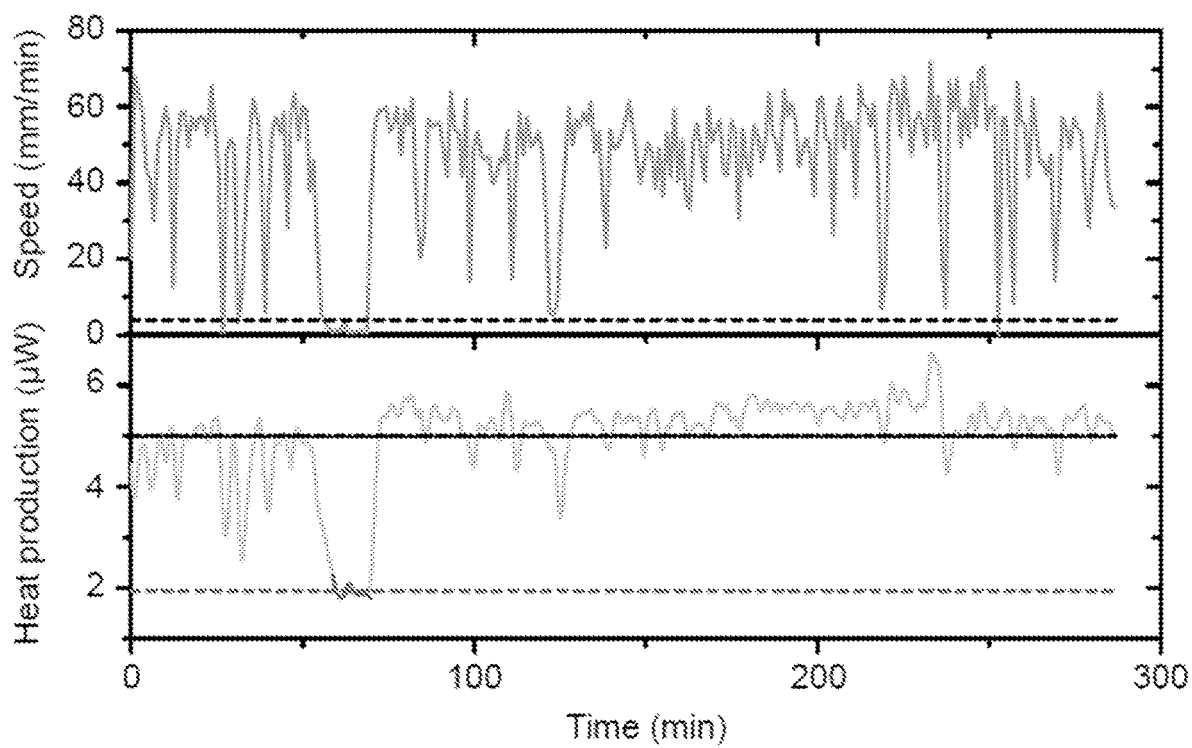
Figure 8D:
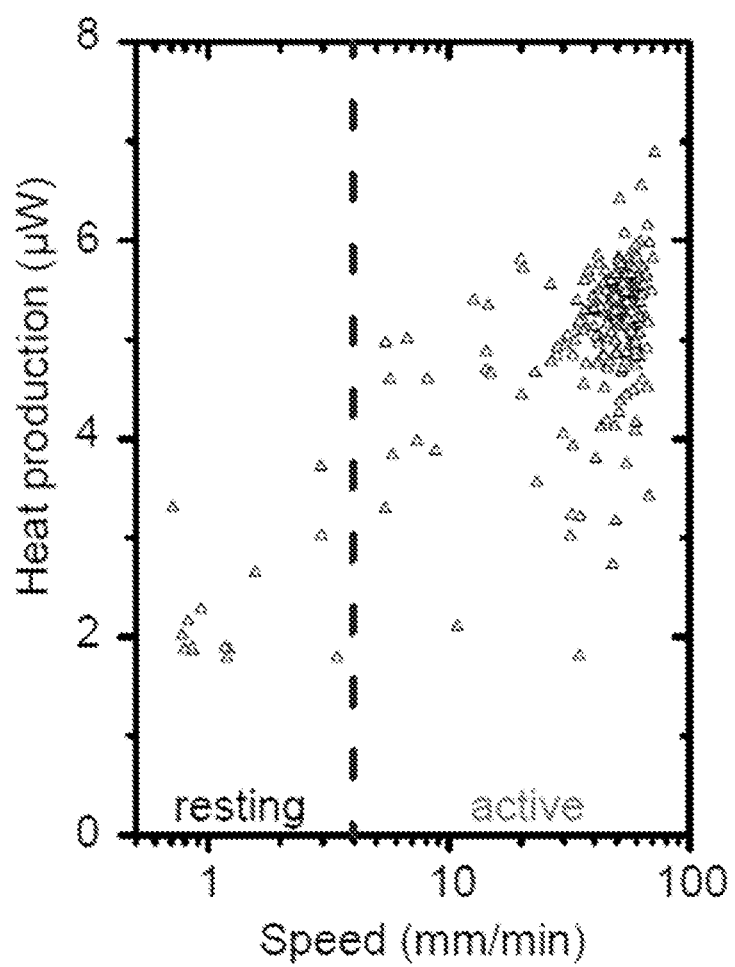

In some embodiments, the inner thermal shield is made of a material having a high thermal conductivity (e.g., greater than 200 W/mK). In some embodiments, the inner thermal shield is made from a material comprising copper, silver, gold, or aluminum. In some embodiments, the inner thermal shield comprises a feedback thermistor (e.g., bonded into the inner shield). In some embodiments, the feedback thermistor is incorporated with three fixed resistors into a Wheatstone bridge circuit (FIG. 7). In some embodiments, the resistors used in the feedback circuit have a high thermal stability, e.g., with a rated temperature coefficient of approximately 0.2 ppm/K (e.g., 0.05, 0.06, 0.07, 0.08, 0.09, 0.1, 0.11, 0.12, 0.13, 0.14, 0.15, 0.16, 0.17, 0.18, 0.19, 0.20, 0.21, 0.22, 0.23, 0.24, 0.25, 0.26, 0.27, 0.28, 0.29, 0.30, 0.31, 0.32, 0.33, 0.34, or 0.35 ppm/K).

In some embodiments, the circuit is supplied with a voltage (e.g., 1-V rms voltage at 37.5 Hz) to avoid coupling to the calorimeter circuit. In some embodiments, the circuit comprises tuning potentiometers and shunt capacitors to balance the amplitudes and phases of voltages in the left and right sides of the bridge, e.g., as described above for the calorimeter circuit. In some embodiments, the inner shield circuit comprises an instrumentation amplifier to perform the voltage difference operation and to amplify the AC signal. In some embodiments, the amplifier signal is was deconvolved using a lock-in amplifier. In some embodiments, a software controller reads the bridge voltage from the lock-in and drives a current through one or more Peltier modules.

Some embodiments comprise optical recording and/or observation (e.g., imaging) of an organism, e.g., to determine periods during which the organism is at rest, e.g., to determine the basal heat production. In some embodiments, the calorimeter device comprises an optical window. In some embodiments, the optical window provides a bandpass filter that transmits electromagnetic wavelengths in the range of approximately 315 nm-710 nm and absorbs longer-wavelength infrared radiation before it reaches the sensitive thermometry in the calorimeter.

As indicated by the data collected during the development of embodiments of the technology provided herein (e.g., FIG. 1d), embodiments of the calorimeter have a thermal conductance of approximately 2 mW/K. Further, data collected during the development of embodiments of the technology provided herein (e.g., FIG. 4c) indicate that embodiments of the calorimeter described herein have a tube thermal conductance of approximately 1 to approximately 5 μW/K.

Methods

Embodiments relate to the use of a calorimetric device as described herein to obtain calorimetric measurements of a living cell and/or organism. Embodiments of methods comprise providing a calorimetric device as described herein. In some embodiments, the technology comprises recording heat measurements (e.g., metabolic heat output), e.g., metabolic heat output of a biological organism. In some embodiments, the technology comprises recording images (e.g., optical observations (e.g., from an imaging sensor)), e.g., of a biological organism. In some embodiments, the technology comprises simultaneously recording heat measurements (e.g., metabolic heat output) and recording images (e.g., optical observations (e.g., from an imaging sensor)) of a biological organism. In some embodiments, the technology comprises simultaneously recording heat measurements (e.g., metabolic heat output) and recording images (e.g., optical observations (e.g., from an imaging sensor)) of a plurality of biological organisms (e.g., 2, 3, 4, 5, 6, 7, 8, 9, 10, 11, 12, 13, 14, 15, 16, 17, 18, 19, 20, 25, 30, 35, 40, 45, or 50 or more) in parallel.

Some embodiments comprise loading (e.g., placing) a biological organism into a calorimetric device as described herein (e.g., in the tube of a calorimetric sub-system as described herein). Embodiments comprise detecting the heat output of the organism (e.g., by the sensing thermistor), e.g., recording the heat output as a voltage and/or a resistance (e.g., by comparison to a reference thermistor). Some embodiments comprise calculating a temperature change detected by the calorimeter as a function of the heat output detected by the sensing thermistor. Some embodiments comprise calculating the metabolic heat output of the organism as a product of the change in the temperature detected by the calorimeter and the thermal conductance of the tube. In some embodiments, the thermal conductance of the tube is determined empirically as described herein. In some embodiments, the methods comprise controlling the temperature of the calorimetric device, e.g., using a heat shield, feedback temperature control, Peltier heating and/or cooling, etc. as described herein. In some embodiments, the technology comprises recording a temperature with a resolution of approximately 10-50 μK (e.g., 10, 15, 20, 25, 30, 35, 40, 45, or 50 μK). In some embodiments, the technology comprises recording heats without a resolution of approximately 10 to 1000 nW (e.g., 10, 20, 50, 100, 200, 500, or 1000 nW).

In some embodiments, recording images of a biological organism comprises recording movement of a biological organism. Some embodiments comprise recording the movement of the biological organism by recording the position of the biological organism (e.g., in 1, 2, and 3 dimensions) as a function of time. In some embodiments, activity level is determined by quantifying distance traversed as a function of time.

Systems

Embodiments of systems comprise a calorimetric sub-system, an optical imaging sub-system, and/or a temperature control sub-system as described herein. For example, in some embodiments a calorimetric sub-system comprises a tube and a sensing thermistor. In some embodiments, the calorimetric sub-system further comprises a circuit (e.g., a Wheatstone bridge) comprising a sensing thermistor and a reference thermistor. In some embodiments, the calorimetric sub-system circuit further comprises resistors to stabilize the circuit to minimize and/or eliminate sensitivity of the Wheatstone bridge voltage to temperature changes of the circuit; one or more potentiometers (e.g., approximately ±20 ppm/K) to balance voltage amplitudes at the operating temperature; one or more shunt capacitors to minimize the phase difference between voltages; and an instrumentation amplifier to determine the voltage difference between the sensing thermistor and the reference thermistor; and a filter (e.g., a 6-pole low pass Butterworth filter).

In some embodiments, systems comprise an optical sub-system comprising, e.g., an imaging component and/or an illumination component. In some embodiments, the optical sub-system comprises an optical filter. In some embodiments, the optical sub-system comprises a microprocessor and/or software to control the imaging component.

In some embodiments, systems comprise a temperature control sub-system comprising, e.g., comprising one or more thermal shields, temperature controller, sensing thermistor, reference thermistor, a heat sink, and/or a component to heat and/or cool the calorimetric device (e.g., a Peltier device). In some embodiments, a temperature control sub-system comprises a circuit for sensing temperature, e.g., a Wheatstone bridge comprising a sensing thermistor and a reference thermistor. In some embodiments, a temperature control sub-system comprises a circuit further comprising tuning potentiometers, shunt capacitors, instrumentation amplifier, microprocessor and/or software, and one or more components to heat and/or cool the calorimetric device (e.g., a Peltier device).

Some embodiments of the technology provided herein further comprise functionalities for collecting, storing, and/or analyzing data. For example, in some embodiments systems and/or devices comprise a processor, a memory, and/or a database for, e.g., storing and executing instructions, analyzing data, performing calculations using the data, transforming the data, and storing the data. Moreover, in some embodiments a processor is configured to control the systems and/or devices. In some embodiments, the processor is used to initiate and/or terminate the measurement and data collection. In some embodiments, the device comprises a user interface (e.g., a keyboard, buttons, dials, switches, and the like) for receiving user input that is used by the processor to direct a measurement. In some embodiments, the device further comprises a data output for transmitting data to an external destination, e.g., a computer, a display, a network, and/or an external storage medium. Some embodiments provide that the device is a small, handheld, portable device incorporating these features and components.

Some embodiments comprise a plurality of calorimetric sub-systems, e.g., for recording calorimetric data and/or image data for a plurality of biological organisms in parallel. Some embodiments comprise a plurality of imaging sub-systems and/or temperature control sub-systems (or components thereof as appropriate). In some embodiments, one or more components of a sub-system are shared among one or more other sub-systems. For example, in some embodiments, a reference thermistor may be used as a reference for a plurality of sensing thermistors; an imaging device may record image data from a plurality of organisms; etc.

Uses

The technology finds use, e.g., in making metabolic measurements (e.g., metabolic heat) in biological organisms. In some embodiments, the technology finds use in measuring metabolic heat in an organism and correlating the metabolic heat to an activity level of the organism. In some embodiments, the organism is a model organism as known in the art (e.g., including, but not limited to, eukaryotes such as insects, nematodes, and other invertebrates). In some embodiments, the organism is a wild-type organism and in some embodiments the organism is a mutant. In some embodiments, the technology finds use in studying cancer, metabolism, circadian rhythm, fertility, biochemical pathways, diet, longevity, aging, and genetics.

EXAMPLES

During the development of embodiments of the technology described herein, experiments were conducted in which the technology was used to make parallelized, real-time, metabolic-rate measurements from individual *Drosophila*.

Materials and Methods for Examples 1-3

Calorimetric Thermometry. To measure small temperature changes, $\Delta T_{sense}$, in the sensing thermistor embedded into the calorimeter (FIG. 1a), embodiments of the technology provide an AC (alternating current)-driven Wheatstone bridge circuit for differential resistive thermometry (FIG. 5). Changes in the sensing thermistor resistance $R_T$ relative to the reference (matching) thermistor resistance $R_M$ were measured with high resolution. The Wheatstone bridge was excited with a 200-mV rms voltage at 19.9 Hz using a waveform generator (Agilent 33210A). High-stability (e.g., approximately ±2 ppm/K) 100-kΩ fixed resistors (Vishay Foil Resistors S Series) were used in the upper half of the bridge so that the bridge voltage $V_B = V_M - V_A$ (see FIG. 5) was insensitive to temperature changes of the circuit itself. Stable (e.g., approximately ±20 ppm/K) potentiometers (TT Electronics/BI Model 7280 Series) with a resistance of 5.1 kΩ were connected in series with the fixed resistors so that the amplitudes of $V_M$ and $V_A$ were balanced to within a few nanovolts at the operating temperature (296 K). Further, the phase difference between $V_M$ and $V_A$ was matched using shunt capacitors $C_M$ and $C_A$ (FIG. 5). In some embodiments, the phase difference was matched by inserting stable (C0G/NP0, ±30 ppm/K) fixed capacitors (TDK FK Series) into sockets connected in parallel with the thermistors. In some embodiments, the difference in instantaneous voltages was minimized and/or eliminated (e.g., <20 nV) by iteratively tuning the potentiometer resistance and shunt capacitance. The difference operation $V_M - V_A$ was performed using an instrumentation amplifier (Analog Devices AD524) that amplifies $V_B$ (e.g., using a gain of 100) before it was filtered using a custom-built 6-pole low pass Butterworth filter. Nine additional half-bridge legs were connected in parallel and referenced to the matching thermistor leg (FIG. 5) so that all ten signals were recorded independently using one circuit. The amplified and filtered signals were recorded using LabView and post-processed using a custom-developed, Fast Fourier Transform-based lock-in technique scripted in MATLAB. The temperature resolution of the circuit was quantified to be ±17 µK (FIG. 6c) and did not set the noise floor of the measurement, which was limited by temperature drift.

Feedback Control of Temperature. A feedback loop that measured and controlled the temperature of two thermal shields, called the "outer thermal shield" and the "inner thermal shield", provided temperature control of the calorimetric system (FIG. 1b). The outer thermal shield (FIG. 1b) was a hollow 24.8×16.5×7.6 cm³ box made of 1.3-cm thick copper. To maintain the outer shield temperature to within approximately 1 mK of the 296 K setpoint, the system comprised a commercial proportional-integral-derivative (PID) temperature controller (Laird Technologies TC—XX-PR-59), which received feedback from a thermistor (US Sensor Corp. USP12838) that was permanently bonded into the copper wall using epoxy (3M Scotch-Weld Epoxy Adhesive 2216 B/A). The controller heated and/or cooled the outer shield by driving current through four Peltier modules (Laird Technologies 56590-502) connected in series. The opposite sides of each of the Peltier modules were in good thermal contact with a large steel plate that served as a heat sink for the outer shield control loop.

Figure 6A:
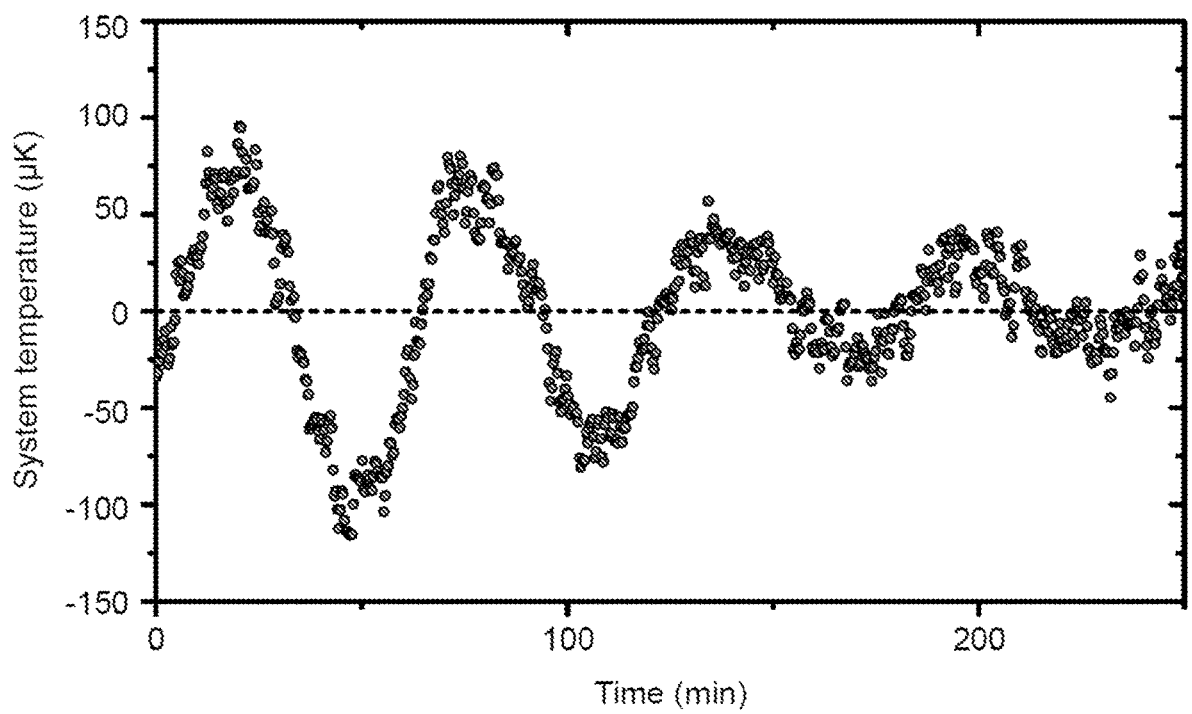
FIG. 6A is a plot showing the inner shield temperature as a function of time. The data indicated that the control (e.g., a MATLAB-scripted PID controller) system, which reads the bridge voltage from the lock-in and drives a current through four Peltier modules (Laird Technologies 56590-502), maintained a stable inner shield temperature to within ±100 μK.

The inner thermal shield (FIG. 1b) was a 17.1×12.7×2.5 cm³ two-piece copper clamshell structure that enclosed the calorimeter and air reservoir cavities when it was assembled. The temperature of the inner shield was controlled using high-resolution temperature measurement from the feedback thermistor and a custom control scheme. A commercial thermistor (US Sensor Corp. USP12838) was permanently bonded into the inner shield using epoxy (3M Scotch-Weld Epoxy Adhesive 2216 B/A). This thermistor was incorporated with three fixed resistors into a Wheatstone bridge circuit (FIG. 7). The circuit was supplied with a 1-V rms voltage at 37.5 Hz (Hewlett Packard 33120A) to avoid coupling to the calorimeter circuit. The amplitudes and phases of $V_L$ and $V_R$ were balanced when the thermistor was set at 296 K by tuning series potentiometers (TT Electronics/BI Model 7280 Series) and shunt capacitors $C_L$ and $C_R$ (TDK FK Series) in the same manner as described above for the calorimeter circuit. An instrumentation amplifier (Analog Devices AD524) performed the difference operation and amplified the AC signal (e.g., using a gain of 100), which was deconvolved using a lock-in amplifier (Stanford Research Systems Model SR830). A MATLAB-scripted PID controller, which read the bridge voltage from the lock-in and drove a current through four Peltier modules (Laird Technologies 56590-502), was connected in series using a commercial current source (Keithley Instruments 6221). This scheme maintained a stable inner shield temperature to within ±100 µK (FIG. 6a).

Humidity. Calorimetric measurements can be affected by evaporative cooling caused by water loss through the specimen's exoskeleton, respiration, and/or the excretion of feces and/or urine (8). In fact, data collected during the development of embodiments of the technology described herein indicated that, under certain conditions, the evaporative heat loss totally overwhelmed the calorimeter signal, leading to an apparent net cooling. Accordingly, embodiments of the technology minimized evaporative heat loss by humidifying the test chamber to nominally 100% relative humidity by including a layer of deionized water in the air reservoir (FIG. 1b). In addition to suppressing the evaporative heat loss, the elevated humidity extended the timespan over which flies survived in the calorimeter by reducing their water loss. In some embodiments (e.g., under some experimental conditions), humidification lengthened the time for the system to stabilize after flies were loaded for an experiment. Accordingly, in some embodiments, humidification was expedited by raising the temperature of the inner thermal shield to 299 K for 10 minutes after flies are loaded before returning the inner thermal shield to the 296 K set point. Steady state operation was reached within approximately 2 hours.

Optical System. Some embodiments comprise optical recording and/or observation (e.g., imaging) through the thermal shields to determine periods during which the flies are at rest, e.g., to determine the basal heat production. However, during the development of embodiments of the technology, experiments indicated that opening holes in the thermal shields permits undesirable thermal coupling between the ambient environment and the calorimeter via radiation exchange. Accordingly, in some embodiments, glass bandpass filters (Thorlabs, Inc. FGS900S) were used as optical windows to reduce thermal drift in the heat production signal. These filters transmit in the wavelength range of approximately 315 nm-710 nm, but absorb longer-wavelength infrared radiation (which primarily contributes to thermal exchange) before it reaches the sensitive thermometry in the calorimeter. The windows were diced and epoxied (3M Scotch-Weld Epoxy Adhesive 2216 B/A) into narrow viewports to limit the view factor from the calorimeter to the environment.

During the development of embodiments of the technology described herein, imaging was performed using low intensity 632-nm LED illumination. Two CCD cameras were positioned above the outer thermal shield to collect images of the illuminated flies during the experiment. Each camera was responsible for collecting light from five calorimeter tubes simultaneously, and the images were logged at two frames per second using LabView software. The resulting images were post-processed using a custom-developed algorithm that estimated the fly center of mass for each individual frame to quantify activity level.

Figure 1D:
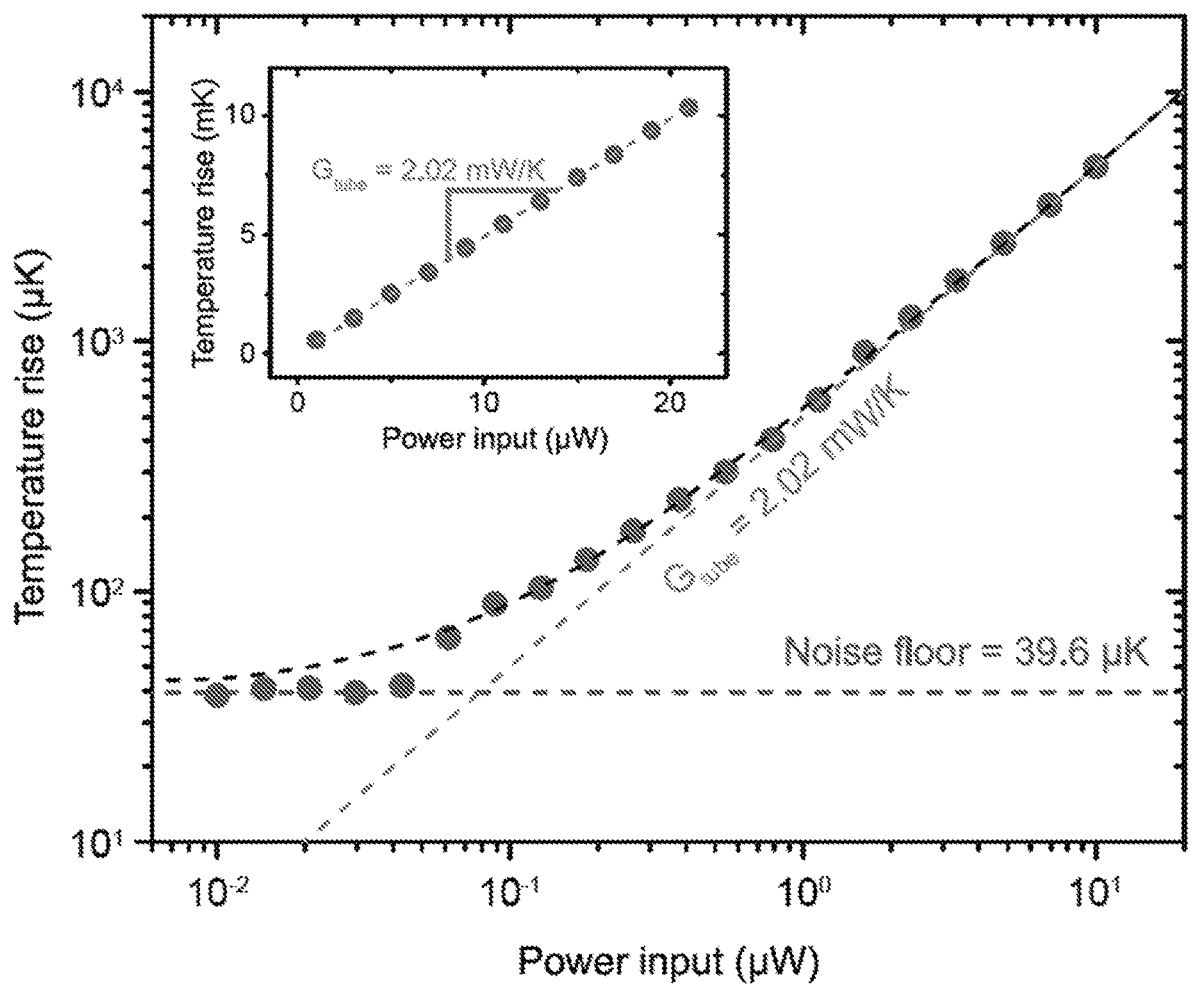
FIG. 1D is a plot of the temperature rise ($\Delta T_{sense}$) vs. controlled electrical heat input ($q_{Joule}$) for a representative calorimeter. The data indicate that heat flows as small as 100 nW are reliably detected. The inset graph plots the same data on linear axes. The inverse of the slope yields $G_{tube}$, which was determined to be 2.02 mW/K.

Thermal Conductance Measurement. In some embodiments, the thermal conductance of the calorimeter characterizes the degree to which the measurement chamber is thermally isolated from the surrounding environment. Therefore, the thermal conductance was measured to quantify the metabolic heat rate of the fly. In particular, the center suspended region of an empty calorimeter was first heated by Joule heating a 5-kΩ heating resistor (FIG. 1d) glued to the tube outer wall. A DC voltage was applied across this resistor using the output channel of a National Instruments DAQ connector block (BNC-2090A)—the heat dissipation is given by $q_{diss}=V^2/R$, where V is the supplied voltage and R is the thermistor resistance. The resulting temperature rise of the center suspended region was then measured using the sensing thermistor (FIG. 1a, c). The measured temperature rise of the calorimeter for various heat inputs was plotted (FIG. 1d). The plot shows that the temperature rise scales linearly with the heat input for $q_{diss}>100$ nW. The inverse slope of the best-fit line through the data points (FIG. 1d, inset) characterizes the thermal conductance of the calorimeter, which the data indicated to be 2.02 mW/K.

Figure 2A:
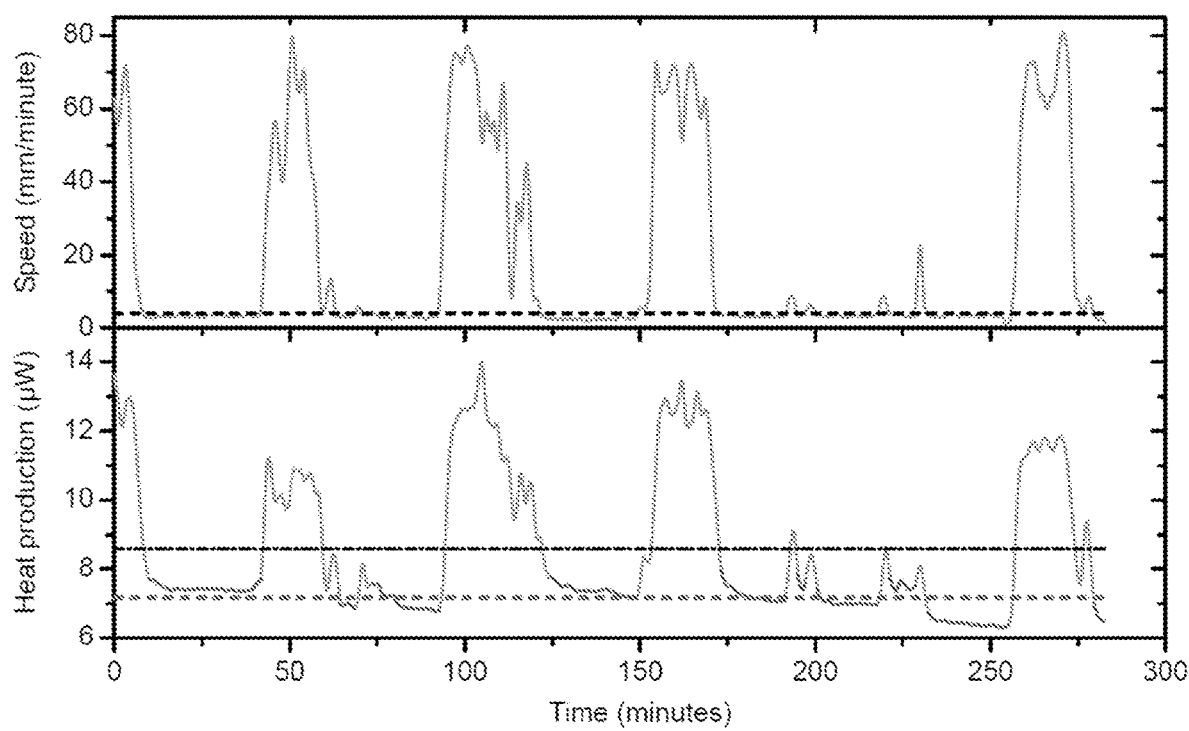
FIG. 2A to FIG. 2D are plots related to metabolic measurement data recorded using embodiments of the technology described herein.

Data Analysis. Basal metabolic heat production was calculated for an individual fly by averaging its heat production during periods of rest (FIG. 2a). One-way ANOVA was performed on the collected data to compare the effects of genotype, age, and diet on metabolic rate. If the ANOVA indicated a significant difference in samples at the p<0.01 level, then a Tukey's honest significant difference test was used to identify which means differed significantly (FIG. 3).

Fly Husbandry and Mass Measurement. Flies were raised on cornmeal-yeast-sucrose food as described previously (e.g., "recipe 4" from the Bloomington *Drosophila* Stock Center's website) under a 12:12 light:dark cycle at 25° C. and 60-70% humidity. To study the effect of different diets on metabolic rate, 3-day old, mated female flies (used for all studies) were transferred into vials containing restricted or high-calorie diet (recipes provided in Table 1). The mass of each fly was determined immediately prior to the start of the experiment by anesthetizing the fly by briefly exposing it to ice and placing it on a digital scale. The experiments were conducted at approximately the same time each day to control for time-of-day variations. The flies used in the study, Canton-S, $w^{1118}$, yw, were obtained from the Bloomington *Drosophila* Stock Center.

TABLE 1

Sugar yeast fly media ingredients

| Component | Restricted Amount | Normal Amount | High Calorie Amount |
| --- | --- | --- | --- |
| Water (1) | 750 ml | 750 ml | 750 ml |
| Water (2) | 250 ml | 250 ml | 250 ml |
| Agar | 21 g | 21 g | 21 g |
| Sucrose | 50 g | 100 g | 150 g |
| Yeast | 50 g | 100 g | 150 g |
| 20% Tegosept | 15 ml | 15 ml | 15 ml |
| Propionic Acid | 3 ml | 3 ml | 3 ml |

Table 1—*Drosophila* food media. To prepare the sugar yeast food media, water (1) and agar are combined in a large kettle. The solution is simmered under slow mixing for 40 minutes. Next, water (2), yeast, sucrose, dextrose (MP Biomedicals), and cornmeal (SYSCO Corp.) are combined in a separate container and mixed well. This mixture is added to the agar solution, and the mixing speed is increased while the food is boiled for 15 minutes. Heat is removed and the food is allowed to cool to 65° C., after which tegosept and propionic acid (Genesee Scientific) are added, and the food is dispensed into 150-ml bottles or 28.5×95 mm vials.

Example 1—Calorimeter Design and Characterization

Figure 6B:
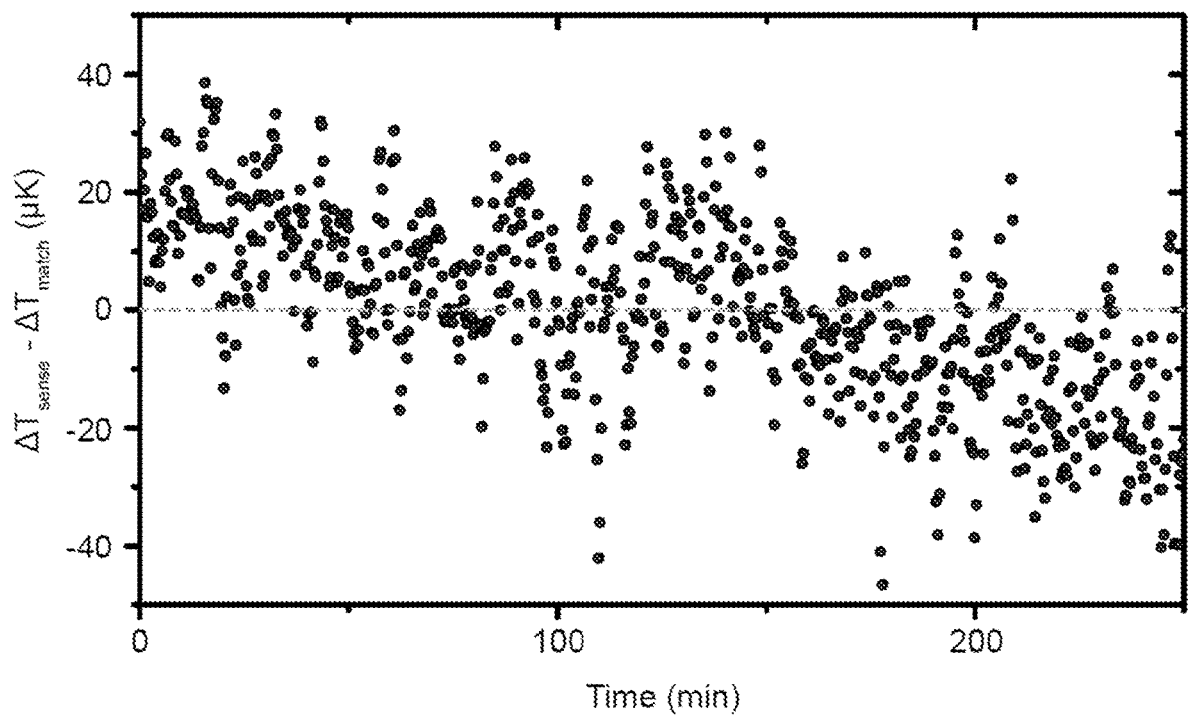
FIG. 6B is a plot showing the temperature resolution of an embodiment of the system described herein. As shown in the plat, the data indicated that the technology provides a temperature resolution of approximately ±30 μK.
Figure 6C:
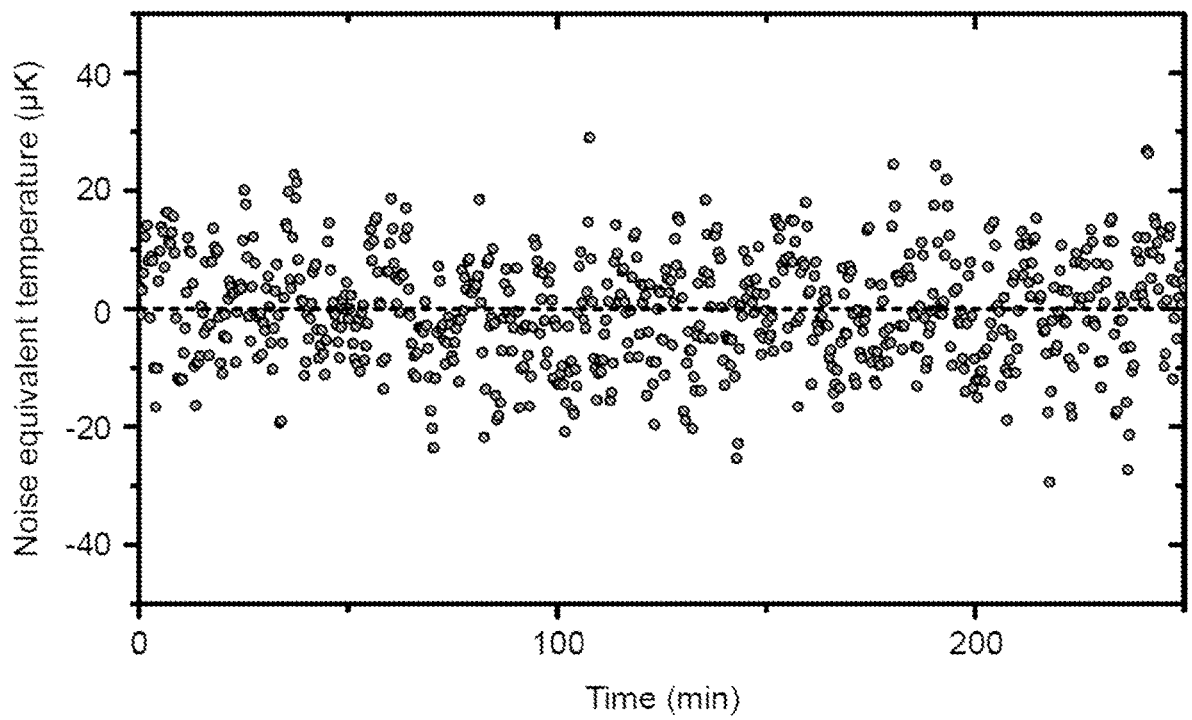
FIG. 6C is a plot showing data that resulted from a Fast Fourier Transform-based lock-in transformation of the amplified and filtered signals. As shown in the plot, the temperature resolution of the circuit was quantified to be ±17 μK and did not set the noise floor of the measurement, which was limited by temperature drift.

In some embodiments the technology relates to a high-resolution direct calorimeter for recording simultaneous metabolic heat output measurements and correlated optical observations from a biological organism. In some embodiments, the technology records simultaneous metabolic heat output measurements and correlated optical observations from a plurality of biological organisms. During the development of embodiments of the technology provided herein, the calorimeter was used to record simultaneous metabolic heat output measurements and correlated optical observations from 10 individual fruit flies (*Drosophila melanogaster*) in real-time. *Drosophila* is a model system for metabolic research (20-22) that shares metabolic pathways with mammals (21). In addition, the fly genome is easily manipulated. Briefly, embodiments of the systems comprise: 1) a calorimetric sub-system with ten suspended glass tubes (VitroCom S102), each of which is instrumented with a sensitive thermistor and serves as an experimental chamber for a single fly; and 2) an optical imaging system to track the movement of each fly in real-time (FIG. 1). Each tube calorimeter comprises a 30-mm long segment suspended in air and both ends of the tube are fixed to the inner portion of a two-layer thermal copper shield (FIG. 1*a*). In some embodiments, the calorimeters are designed to function as follows: For metabolic measurements, a single fly is loaded into and confined to the central segment of the tube (FIG. 1*a*). The heat output associated with the fly's metabolic processes causes the temperature of the calorimeter to increase by $\Delta T_{sense}$, which is detected by the high-resolution thermistor (FIG. 1*a, c*). The heat output $q_{metabolic}$ is directly obtained from $$q_{metabolic} = G_{tube} \times \Delta T_{sense}$$

where $G_{tube}$ is the calibrated thermal conductance of the glass tube (e.g., approximately 2 mW/K; see, FIG. 1*d* and the Methods above). Thus, small heat outputs are measured by detecting small temperature changes. In embodiments of the system described herein, detecting small temperature changes is limited by temperature drift of the thermal shields and 1/f electronic noise (23-25). Temperature drift in the inner shield was minimized and/or eliminated using active PID-feedback control of the shields and an AC-driven bridge circuit (see Methods), e.g., to minimize the effects of 1/f electronic noise. During the testing of embodiments of the technology, data indicated that the technology provides excellent temperature resolution (e.g., ±30 μK) (Methods, FIG. 6*b*) and, consequently, provides a calorimetric resolution of approximately 100 nW (FIG. 1*d*). In some embodiments, the temporal resolution of the calorimeter is set by the thermal time constant of the calorimeter device and is approximately 50 seconds.

During the development of embodiments of the technology provided herein, experiments were conducted to correlate measured metabolic output of flies to their activity level. Data were collected using the calorimeter's imaging system to record the movement of flies in real time (see Methods). Two CCD cameras (FIG. 1*b*) were positioned above the setup and continuously recorded the flies and tracked the flies' position and activity level (e.g., quantified as distance traversed per time) using a custom-developed algorithm (see Methods). Thermal perturbation of the calorimeter was minimized and/or eliminated by using low illumination levels (e.g., at a wavelength of approximately 632 nm and a power density of approximately 0.5 μW/cm$^2$) and optical windows (FIG. 1*b*) that block infrared radiation (most radiative heat transfer at room temperature occurs in the infrared range (26)). The activity and metabolic output were recorded simultaneously (see, e.g., FIG. 2*a*). In particular, the upper panel of FIG. 2*a* shows a representative activity trace from a single Canton-S fly while the lower panel presents the metabolic output obtained simultaneously with the activity trace. These data indicated that (1) the fly's activity level and metabolism are highly correlated; and (2) the fly is predominantly either resting or highly active, with almost no intermediate levels of activity. Thus, the simultaneous, time resolved calorimetric and optical measurements identified extended time periods of minimal physical activity for the flies that provides for estimating the basal metabolic rates of individual flies.

Figure 2B:
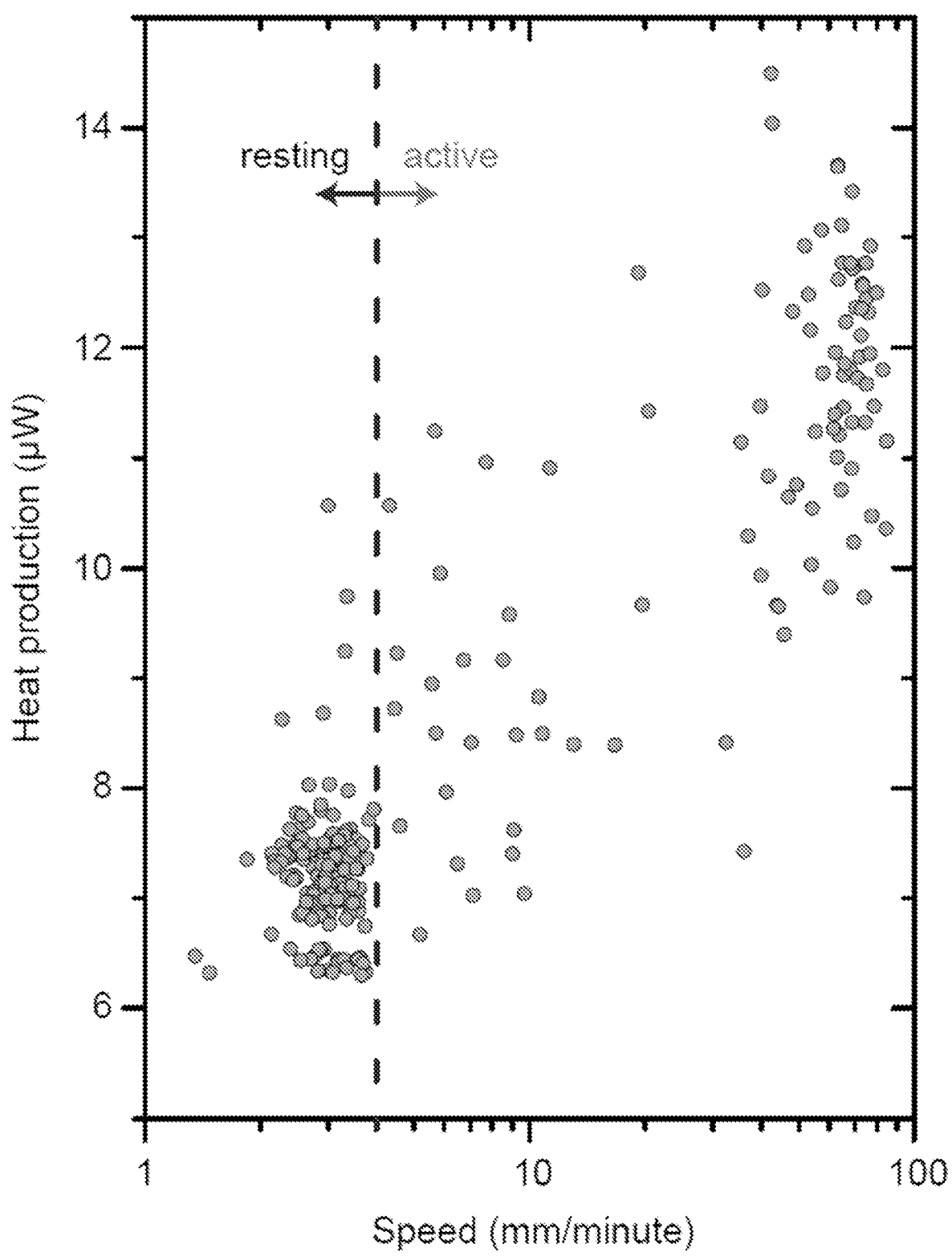
Figure 2C:
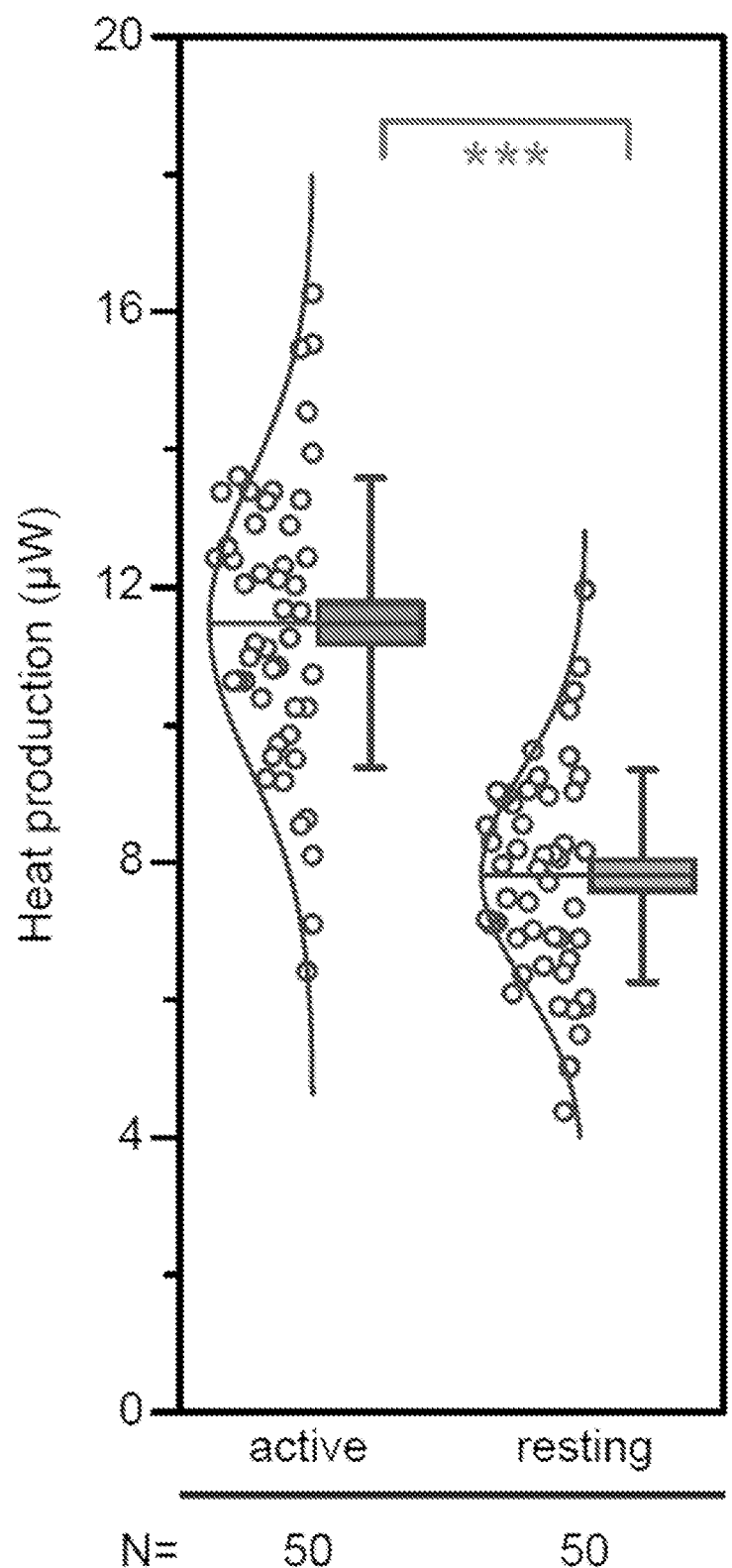
Figure 2D:
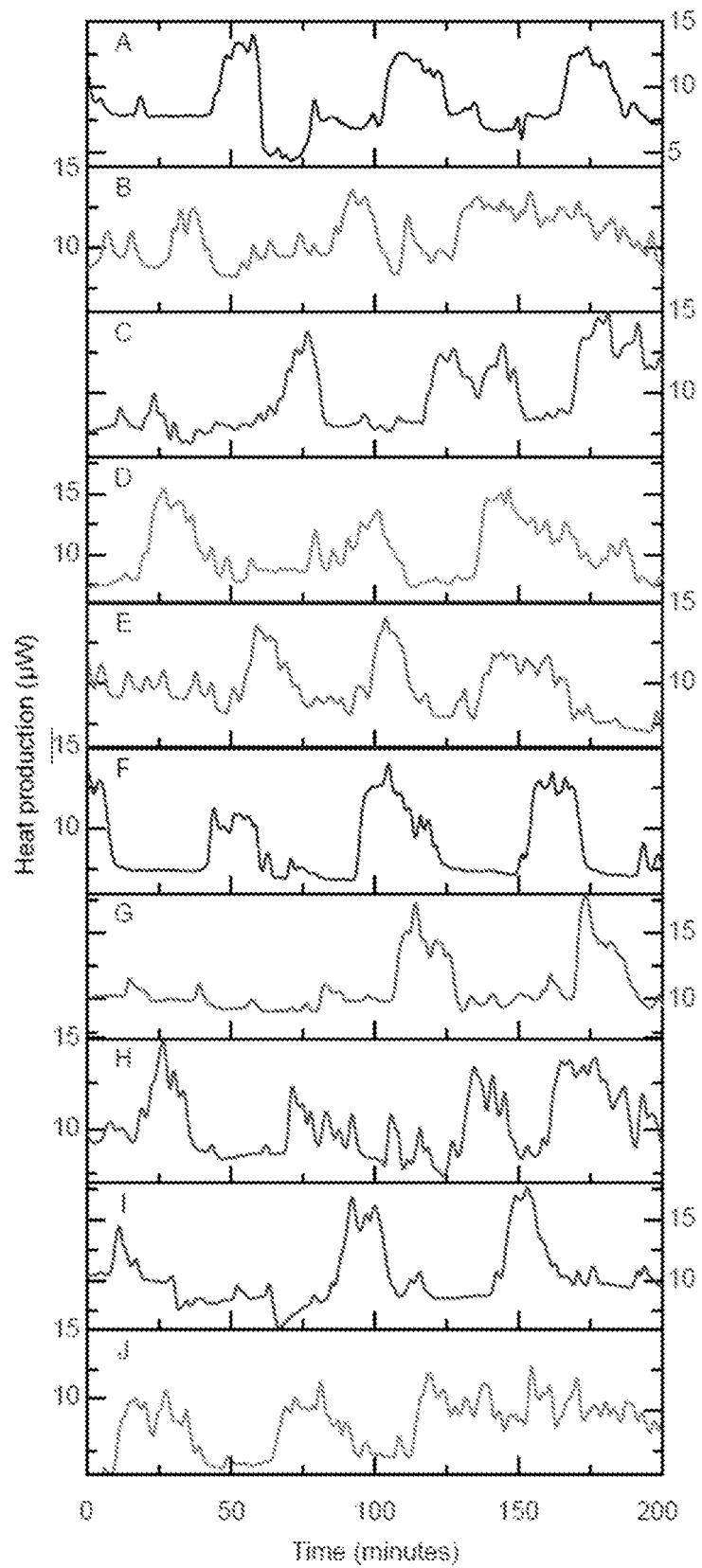

Next, during the development of embodiments of the technology provided herein, experiments were conducted to visualize the relationship between metabolism and activity level. In particular, data were collected from measurements of heat output and plotted as a function of fly activity for the same Canton-S fly discussed above (FIG. 2*b*). As expected, the data indicated that the heat output increased for higher levels of activity, and two clusters of points were identified: one tight cluster at low activity and metabolism ("resting") and a second cluster at high activity and metabolism ("active"). The data indicated that the data clustered similarly for other genotypes (FIG. 8*a*-8*d*). As used herein, a fly is "at rest" (e.g., during analysis of basal metabolic rate) if its center of mass moves <4 mm over a 1-minute time period. Data were collected comparing the metabolic data collected during rest and high activity (movement >50 mm/min) levels for a sample of 50 Canton-S flies (FIG. 2*c*). The data indicated that metabolic output increases by approximately 50% when a fly is active (FIG. 2*c*). The metabolic rates of 10 flies were recorded concurrently in a single experiment (FIG. 2*d*). The data from all 10 calorimeters do not track with each other, indicating that the calorimetric signal from each tube is independent and not influenced by an external stimulus. Further, these data also indicated that this behavior is innate to the fly and not governed by the fly's response to changes in the environment or an artifact of the measurement technique.

Example 2—Effects of Genotype, Age, and Diet on Metabolic Rate

Figure 3A:
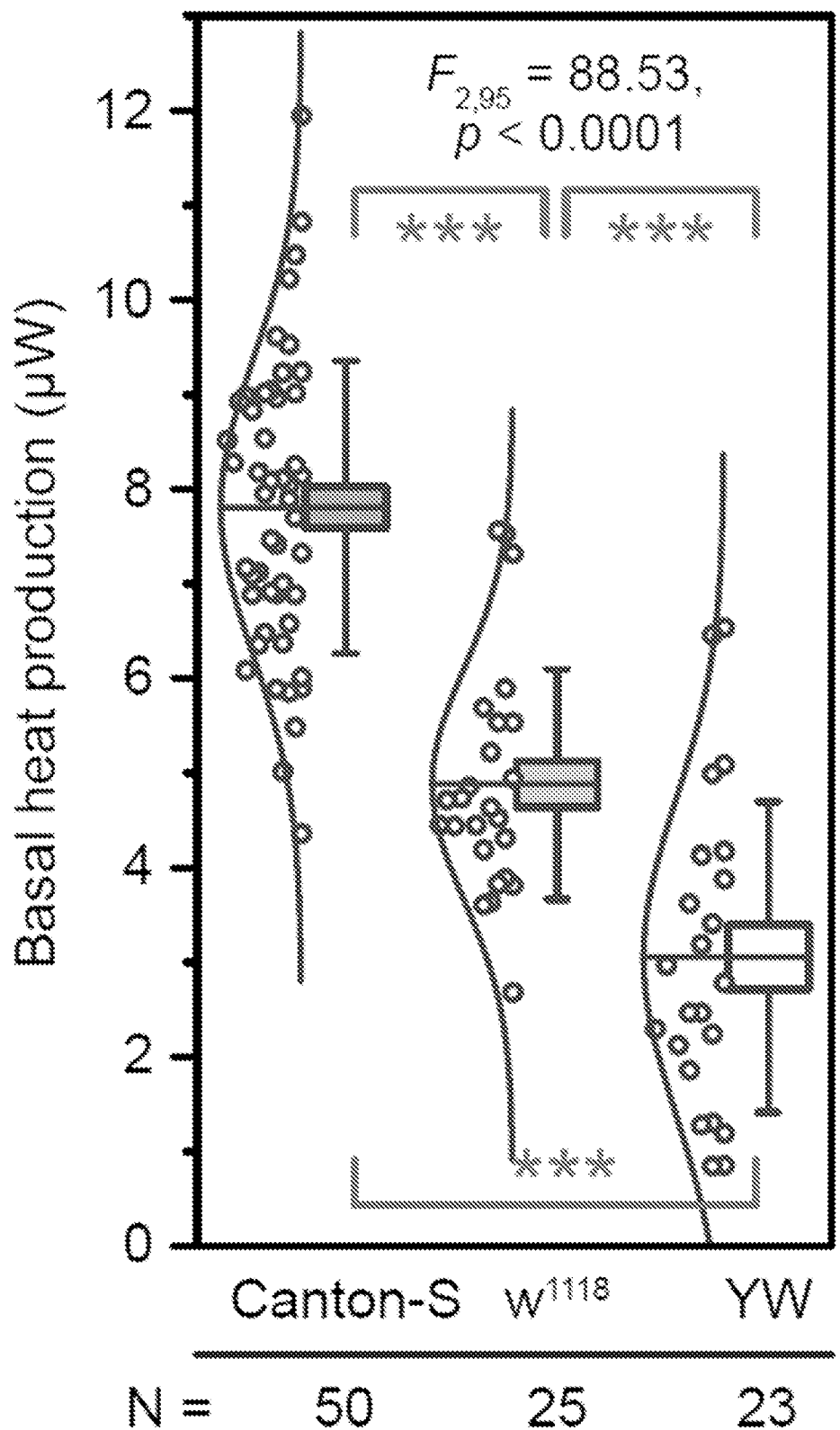
FIG. 3A to FIG. 3F are plots related to basal heat production rates.
Figure 3B:
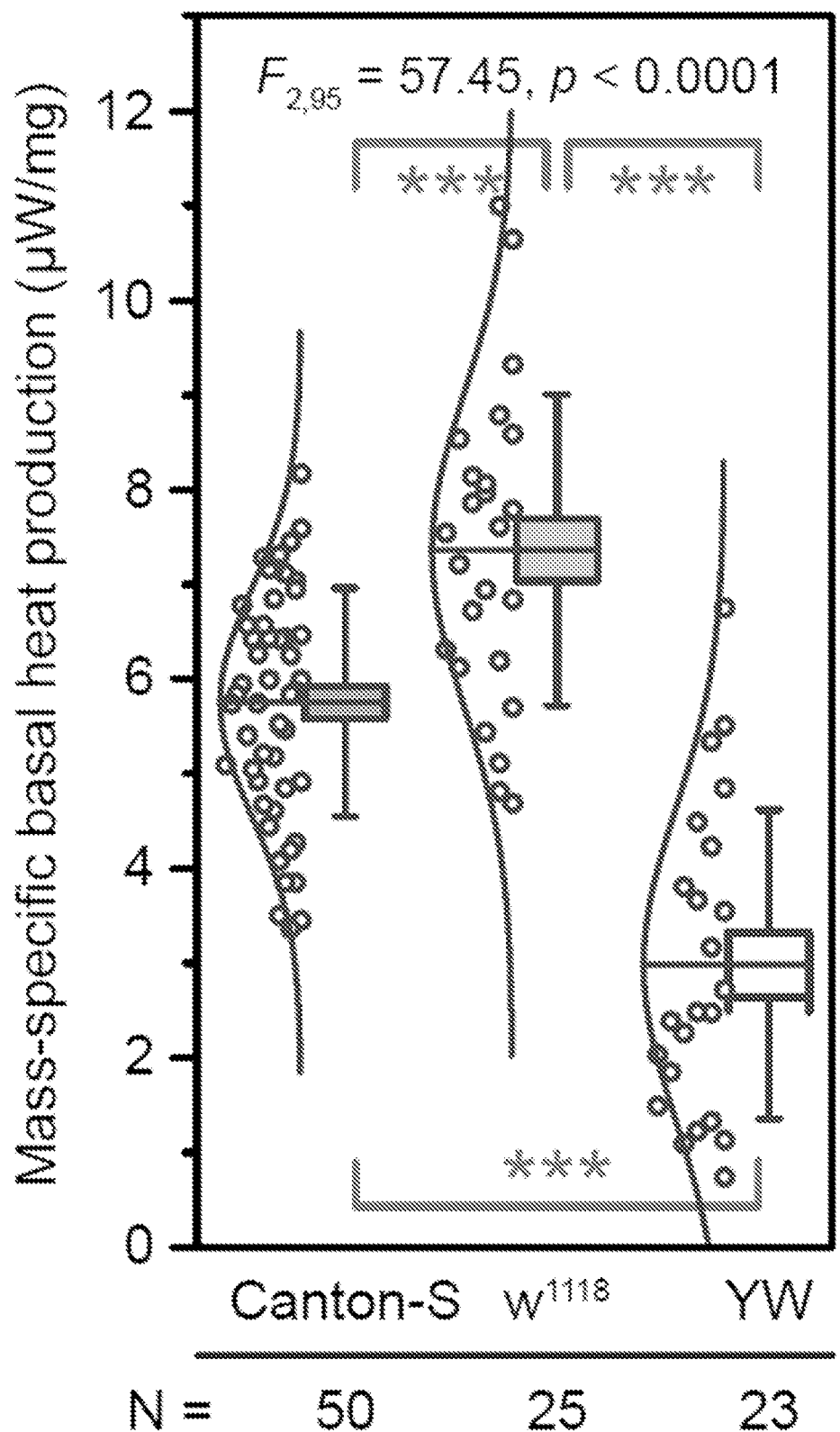
Figure 9A:
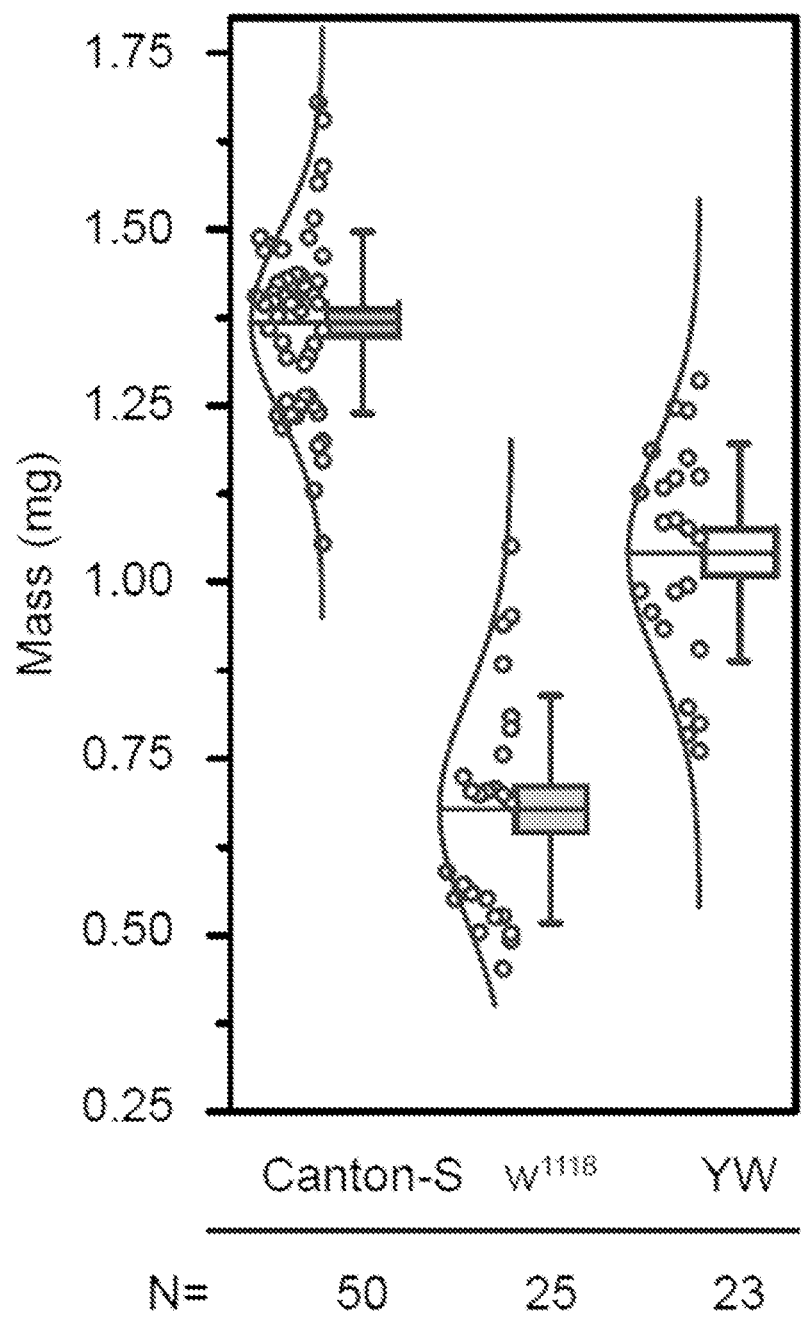
FIG. 9A to FIG. 9C are plots showing basal heat production normalized to body mass to determine mass-specific heat production.
Figure 9B:
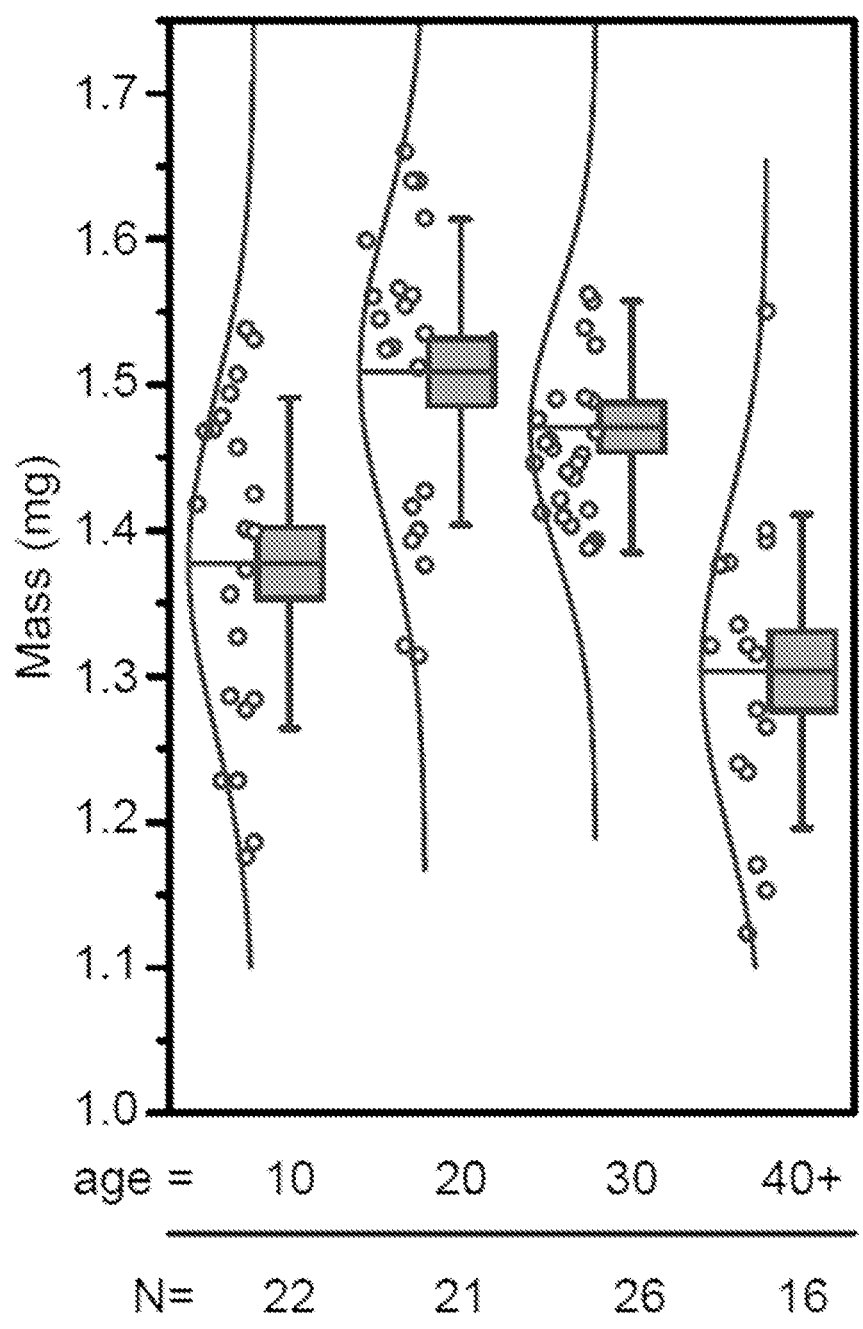
Figure 9C:
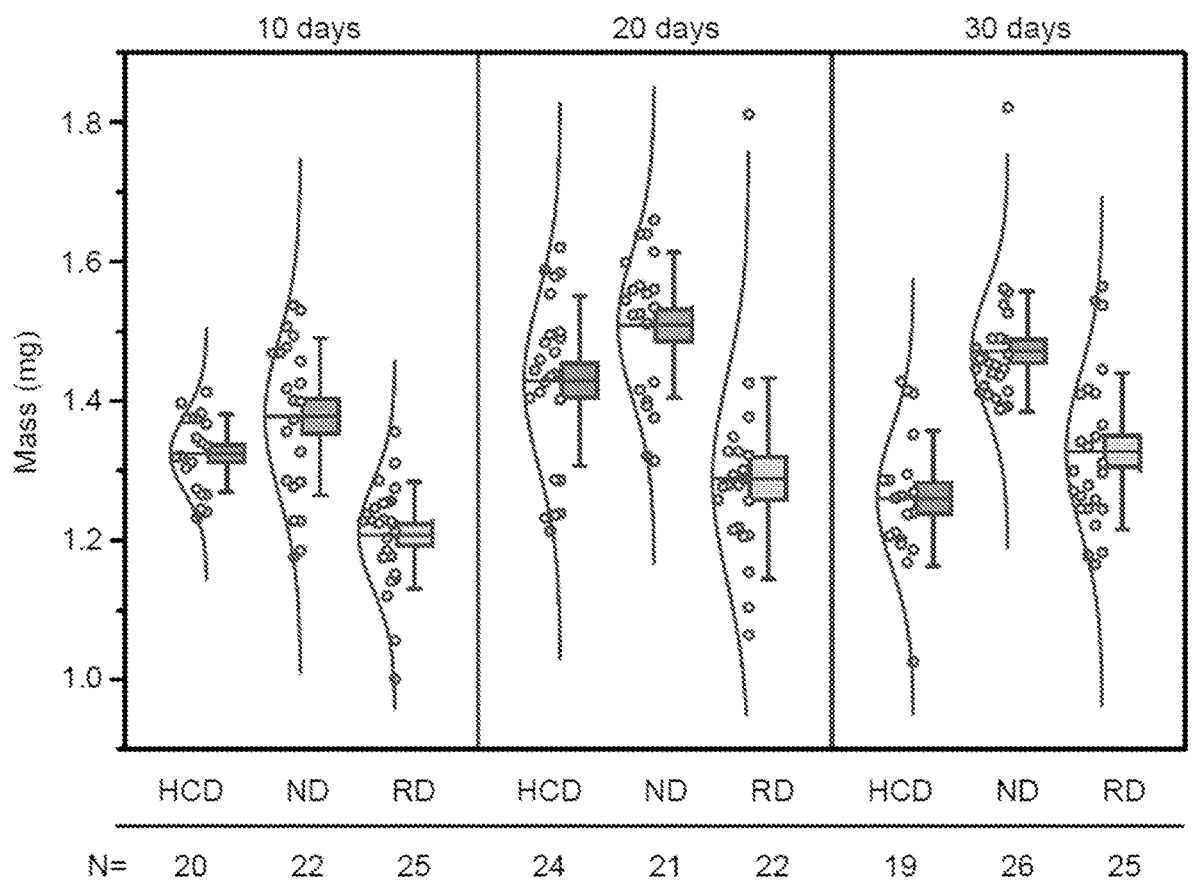
Figure 10A:
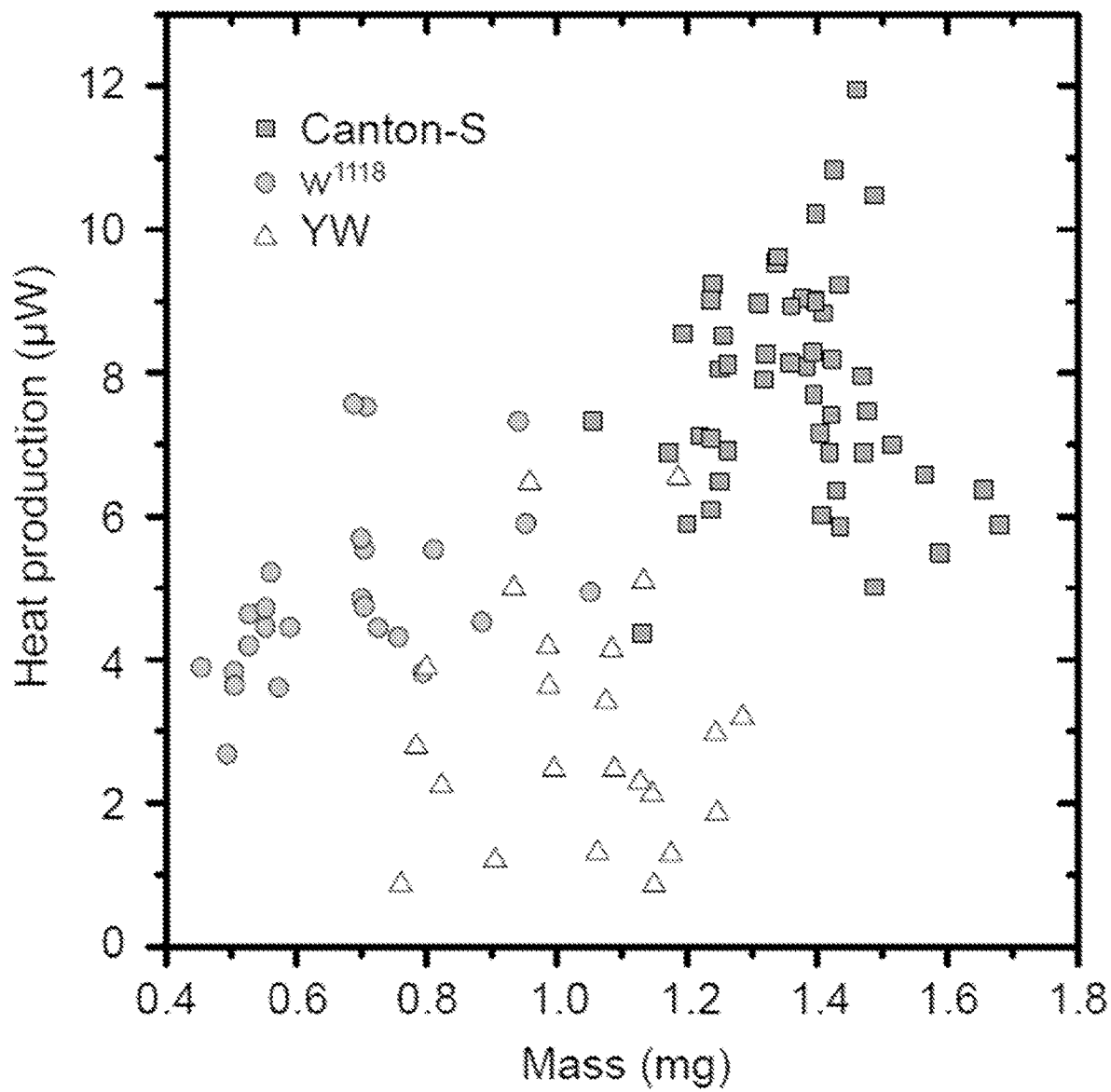
FIG. 10A to FIG. 10C are plots showing average basal heat production as a function of fly mass.
Figure 10B:
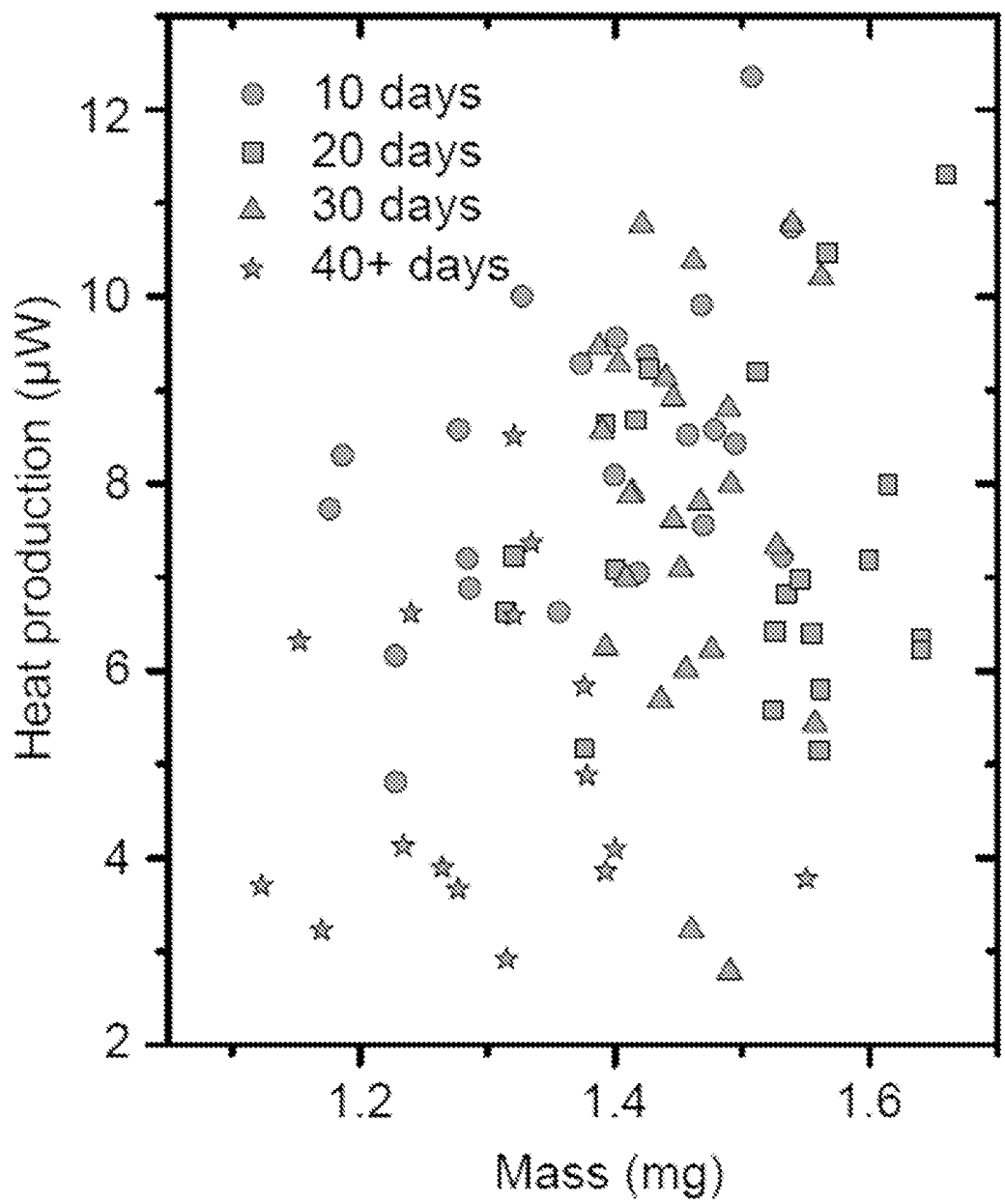
Figure 10C:
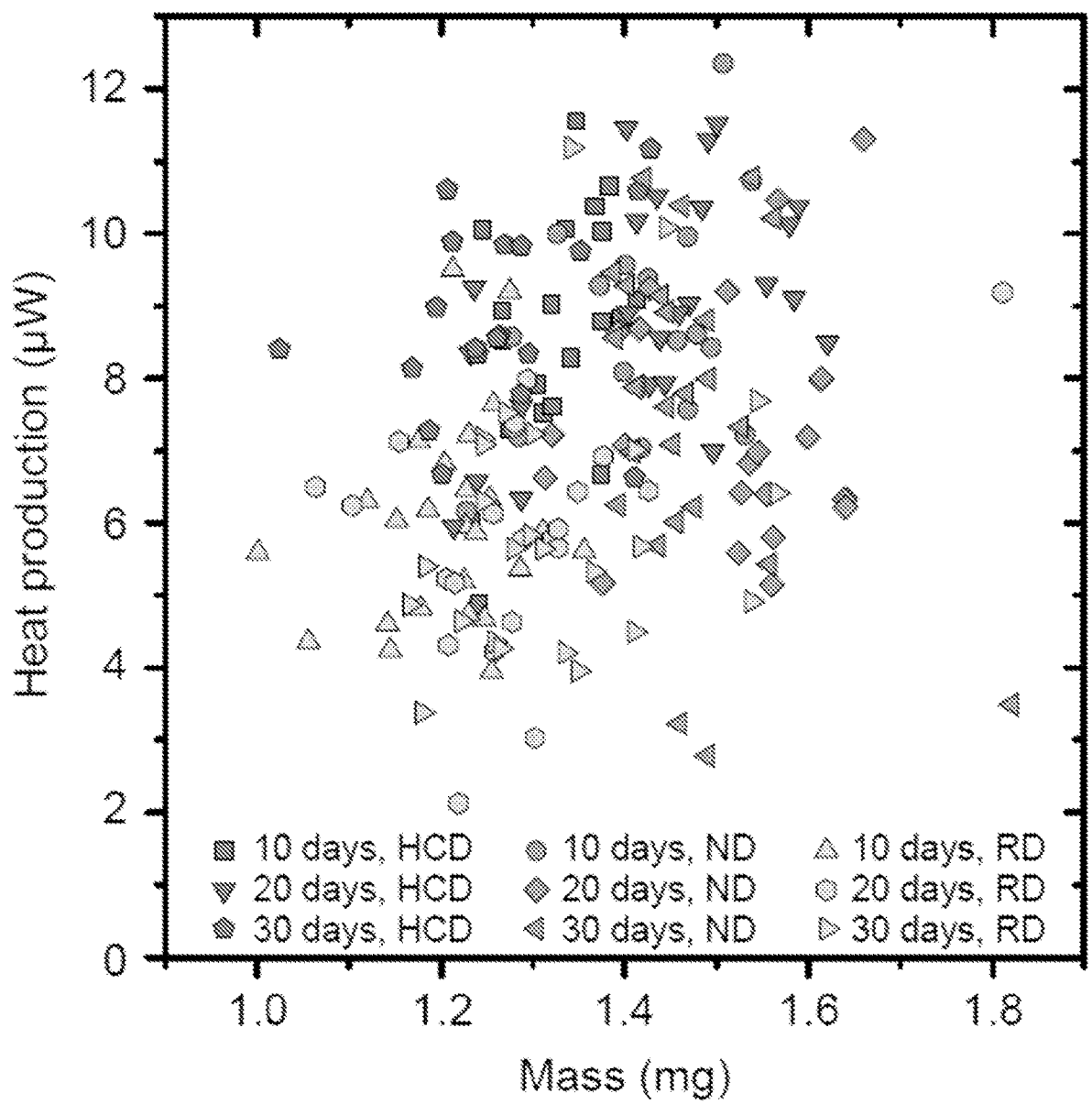

During the development of embodiments of the technology described herein, experiments were conducted to test embodiments of the systems to discern differences in metabolic output. In particular, data were collected from measurements of three standard laboratory wild-type strains of *Drosophila*: wild-type Canton-S flies, white (w$^{1118}$), and yellow white (yw) mutant strains. In these experiments, mated female flies were used three days after eclosion and raised on sugar yeast food (normal diet (ND), Table 1). Basal metabolic output was recorded (FIG. 3a) and each fly's basal heat production was normalized to its body mass (27) (FIG. 9a to 9c) to determine the mass-specific heat production (FIG. 3b). The data indicated a significant difference between flies of different genotypes for both absolute heat production (FIG. 3a) and mass-specific heat production (FIG. 3b). These data indicated that the technology described herein measures differences in metabolic rates in real-world physiological experiments. The mass-specific basal metabolic heat production of adult Canton-S flies (5.78 μW/mg), $w^{1118}$ flies (7.36 μW/mg), and yw flies (2.99 μW/mg) measured according to the technology provided herein were surprisingly different than previously reported mass-specific metabolic rates of 17.3±0.3 μW/mg that were measured from a collection of flies with no activity monitoring (28). Interestingly, data acquired during the experiments described herein also indicated that the genotype with the smallest average mass ($w^{1118}$, FIG. 9a) did not exhibit the smallest basal metabolism (FIG. 3a) as one would have expected from simple allometric scaling (29) (FIG. 10a, FIG. 10b, and FIG. 10c).

Figure 3C:
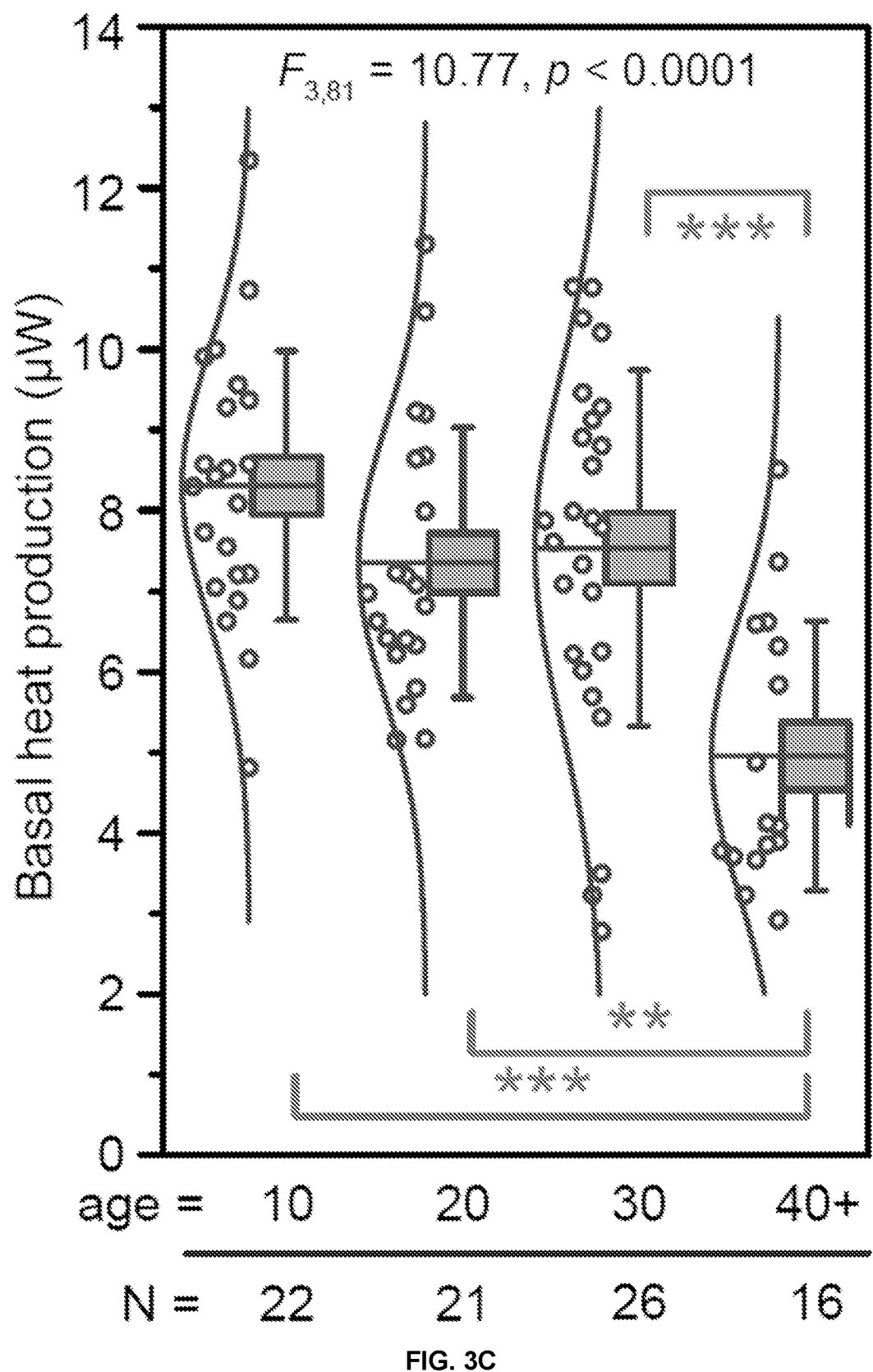
Figure 3D:
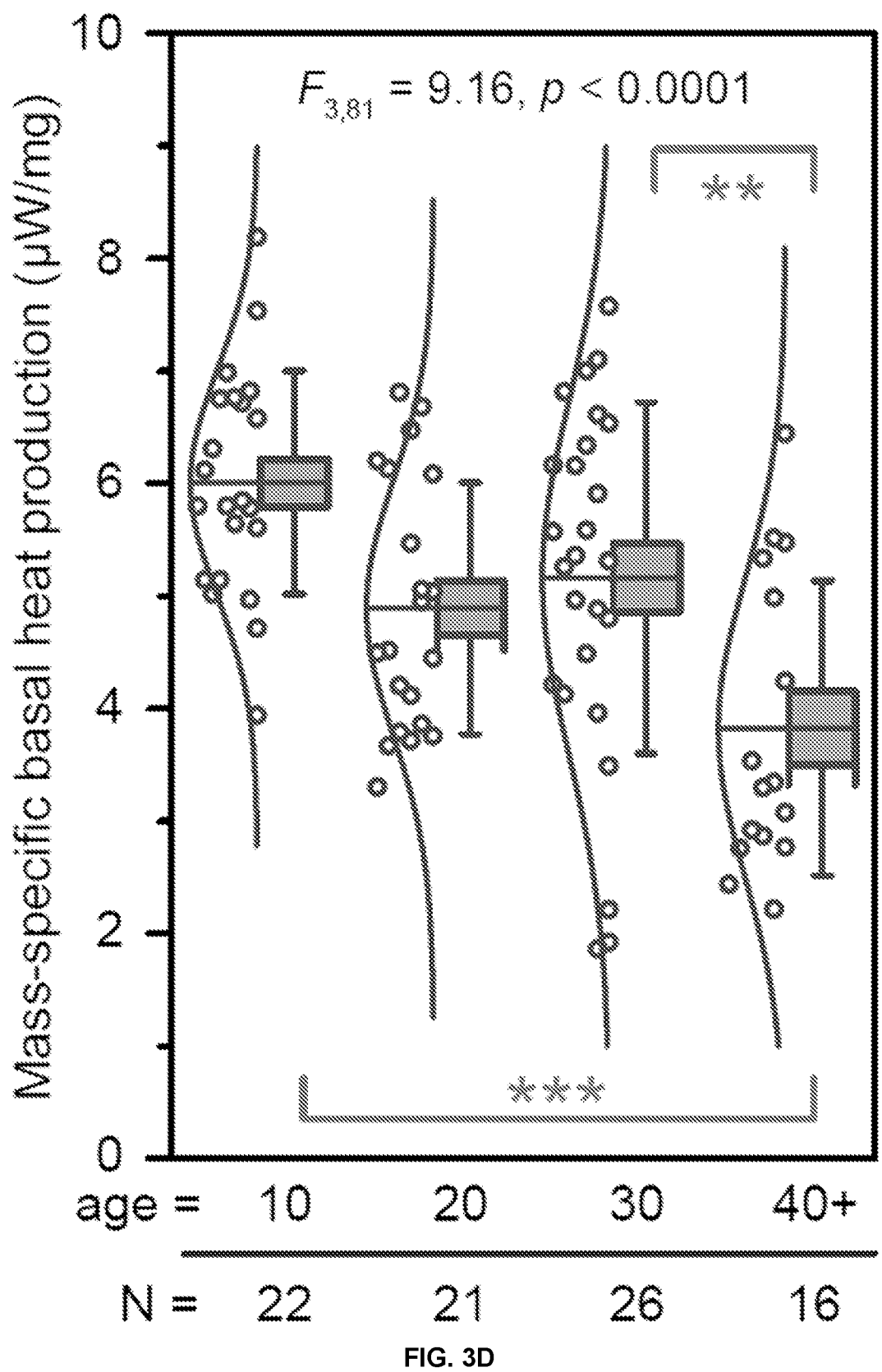

In addition, experiments were conducted during the development of embodiments of the technology described herein to test the effect of aging on metabolic activity, which would also demonstrate the utility of the technology for providing important biological insights. Specifically, the basal metabolic rates of Canton-S flies were recorded 10, 20, 30, and 40 days after eclosion. The data indicated that both absolute and mass-specific basal metabolic rates depended significantly on the ages of the flies (FIG. 3c, d). Specifically, the mean heat production for flies 40 days and older (e.g., approximately 3.83 μW/mg) was significantly lower than younger 10-day old flies (e.g., 6.01 μW/mg) or 30-day old flies (e.g., 5.16 μW/mg). The age-dependent difference in the basal metabolic rate of flies was surprising and had previously not been reported. These data suggest that the calorimeter technology described herein provides sufficient sensitivity to quantify the decline in metabolism of a fly near the end of the fly's lifespan.

Figure 3E:
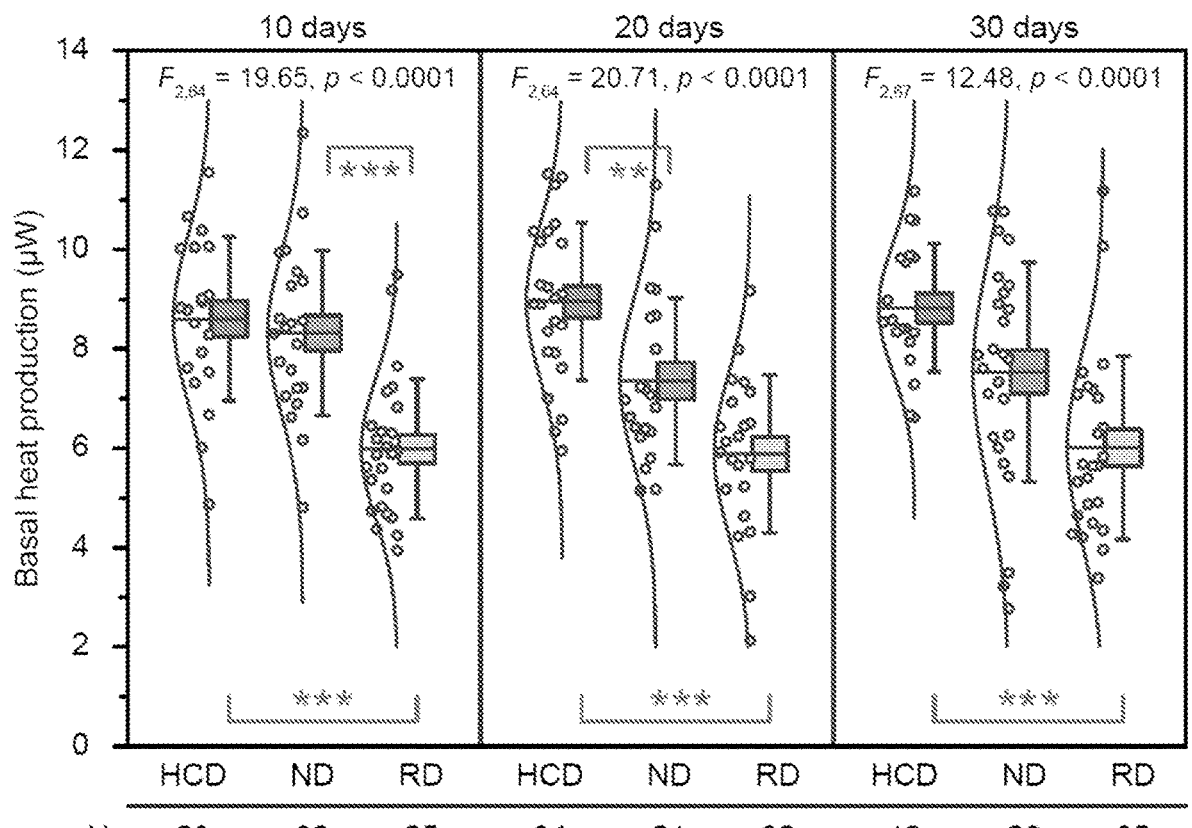
Figure 3F:
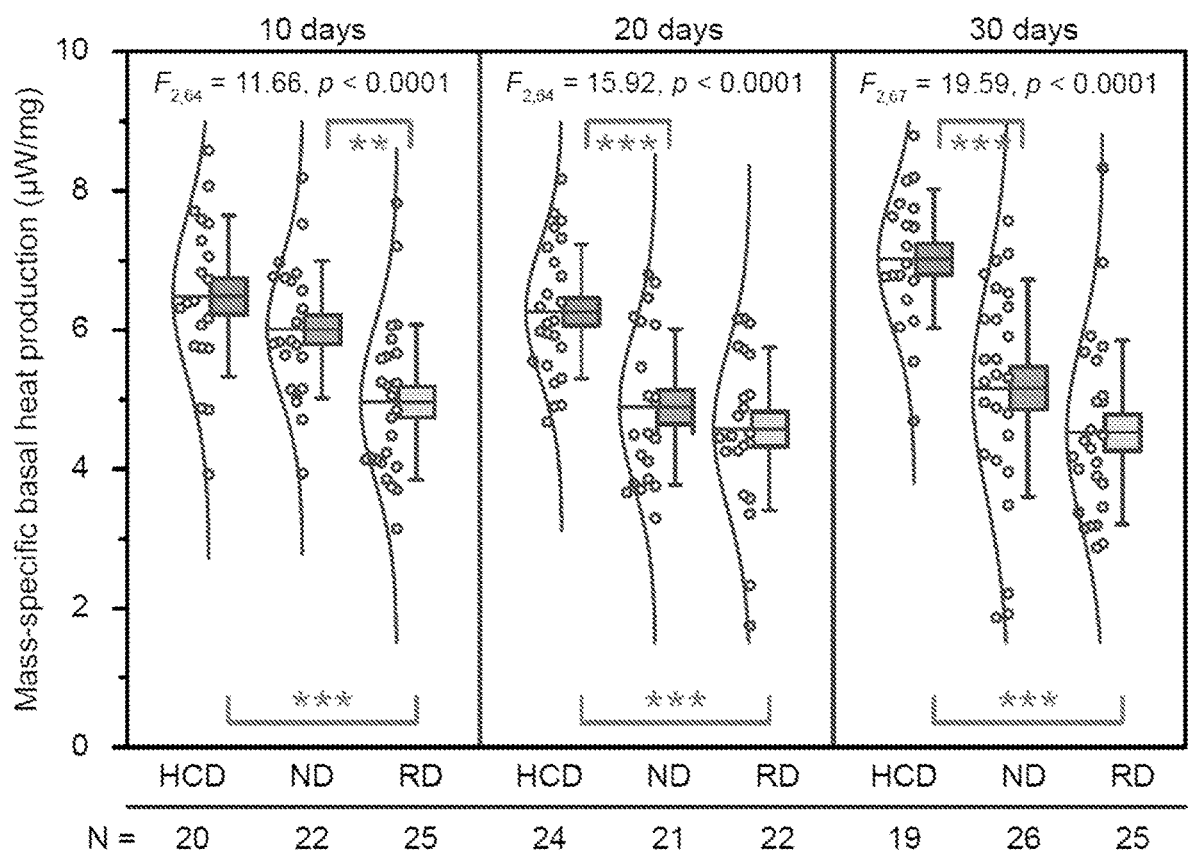

Lastly, experiments were conducted using embodiments of the calorimeter technology to examine the effects of dietary restriction on metabolism. Dietary restriction (DR), the limitation of food intake below the normal level without malnutrition, has been shown to extend life span in various model organisms, e.g., unicellular eukaryotes (e.g., yeast (30)) and multicellular eukaryotes (e.g., nematodes (16, 31); fruit flies (28); rodents (32); and primates (33, 34)). Data were collected to measure how DR affects organismal metabolic rate and help to determine if DR increases metabolic output (see, e.g., 30, 35) or does not change metabolic output (see, e.g., 28). Accordingly, basal metabolic rate measurements were performed on adult Canton-S flies of several different ages and raised on food of varying caloric quality. The data collected for 10 day-old flies indicated unambiguously that a fly's diet significantly affects both its absolute and mass-specific basal metabolic rate (FIG. 3e, f). Specifically, the data indicated that flies on high-calorie diets (HCD, Table 1) had higher basal metabolic rates (FIG. 3e) and mass-specific basal metabolic rates (FIG. 3f) than DR flies. Data collected in similar experiments performed with 20-day old flies and 30 day-old flies indicated higher basal metabolic rates (FIG. 3e) and mass-specific basal metabolic rates (FIG. 3f) than DR flies for the older flies (FIG. 3e, f). Previous data suggested that DR has no effect on mass-specific metabolic rate (28) or that DR increases mass-specific metabolic rate (30, 35). Without being constrained to any single theory, it is contemplated that previous reports may have reported these effects because the measurements had a coarser resolution or used indirect probes of metabolism.

Example 3—Picowatt Calorimetry in Living Systems

During the development of embodiments of the technology described herein, experiments were conducted to quantify unmodulated heat currents at high-resolution (e.g, approximately 250-pW), e.g., to characterize the metabolism of single cells or organisms. Embodiments of the technology provide a calorimeter having two important characteristics: 1) a capability of measuring power outputs with a picowatt resolution; and 2) providing an environment that is compatible with the physiology of the cell and/or organism under study. In particular, the technology provides embodiments of a glass capillary calorimeter that provides a measurement resolution of approximately 250 pW. This calorimeter provides an improved resolution over previous technologies (e.g., state-of-the-art unmodulated calorimeters, e.g., as described in Lee et al. (2009) "High-sensitivity microfluidic calorimeters for biological and chemical applications" PNAS 106: 15225) that provide approximately a 4-nW resolution.

Figure 4A:
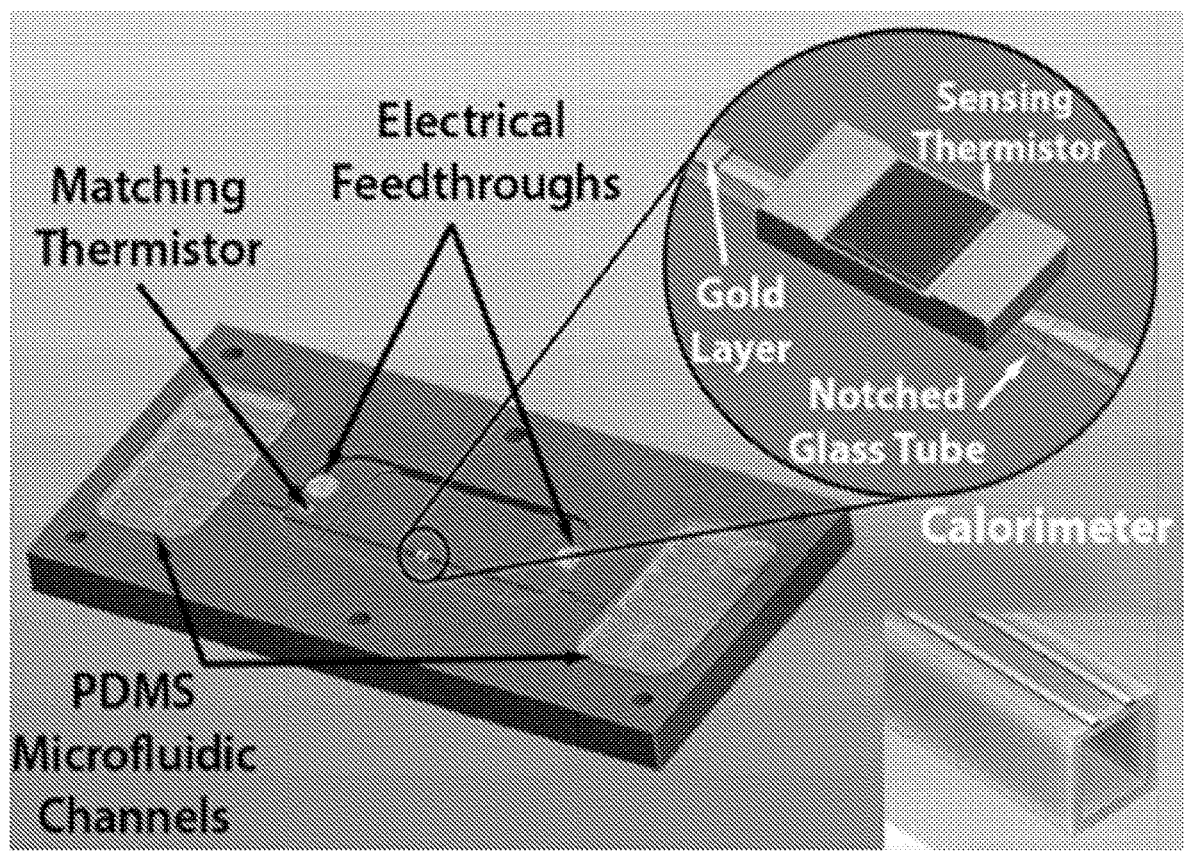
FIG. 4A to FIG. 4D are related to embodiments of the technology for quantifying unmodulated heat currents, e.g., from a living organism or single cell.
Figure 4B:
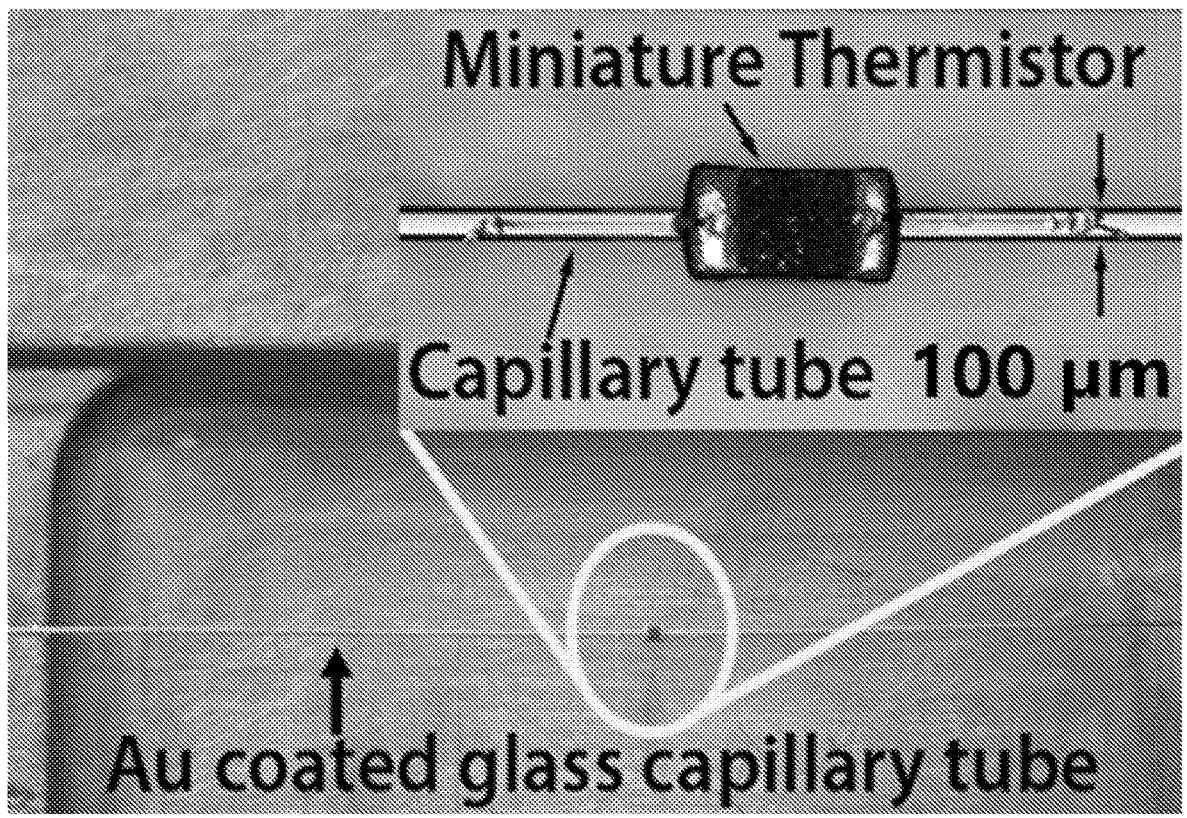
Figure 4C:
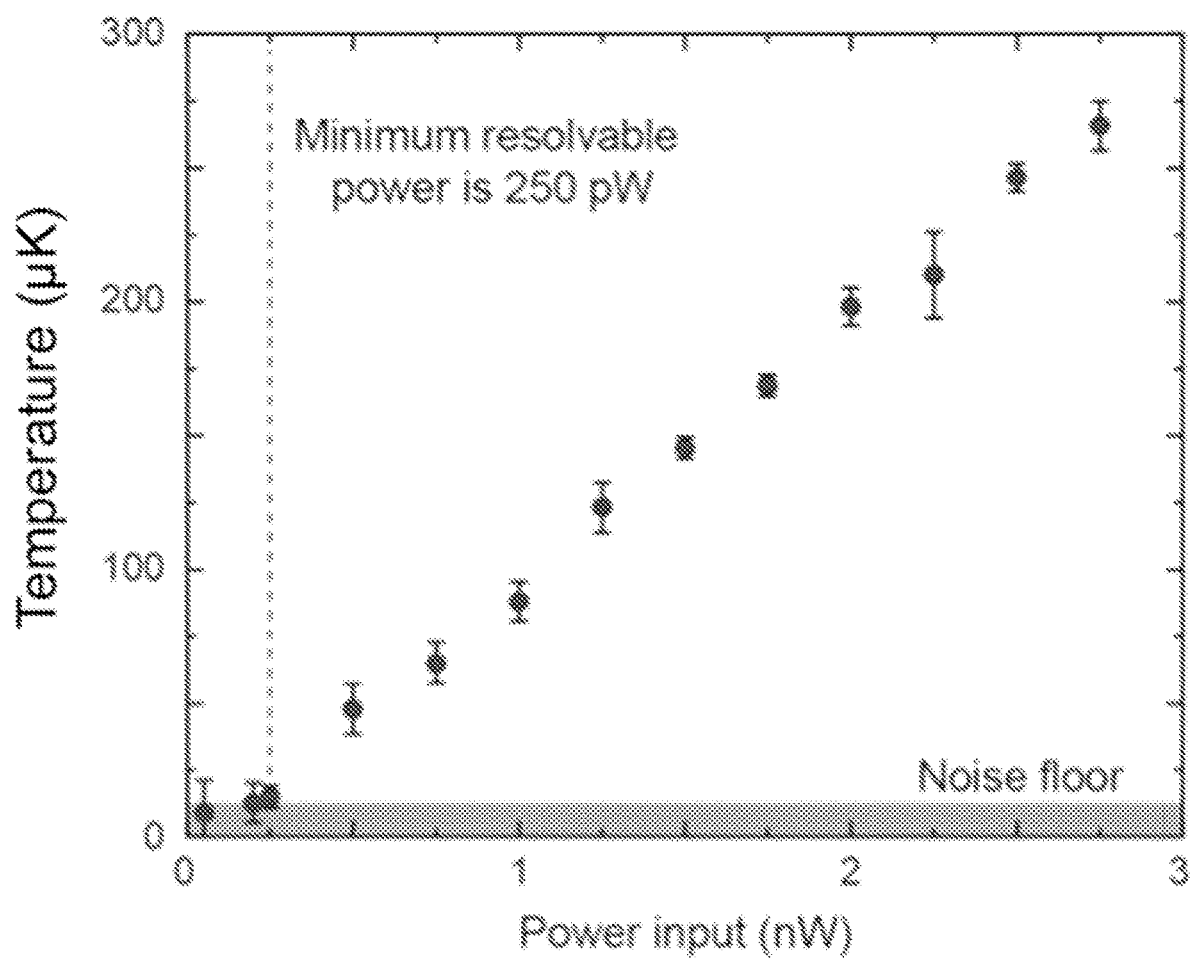

In some embodiments, the capillary-based calorimeter comprises a high-resolution glass-encapsulated miniature thermistor that is mounted on a glass capillary tube coated with gold on all sides (e.g., to reduce its emissivity) (FIGS. 4a and 4b). This instrumented capillary tube is placed on a copper plate that features a trench for thermally anchoring the ends of the capillary tube and thermally isolating the suspended region (FIGS. 4a and 4b). The air surrounding the suspended region of the capillary tube is removed (e.g., by creating a vacuum), which improves the thermal isolation of the suspended region.

Data were collected during use of embodiments of the calorimeter. For example, the thermal resistance to heat flow from the center of a glass capillary tube (VitroCom, Mountain Lakes) (e.g., having a length of 2 cm, a wall thickness of 25 μm, and an inner cross-section of 50 μm×50 μm) to the end clamped to the copper plate at ambient temperature (see FIG. 1a) was approximately 10 μW/K. Further, the glass-encapsulated measurement thermistor located on the capillary, when referenced to a second thermistor embedded into the feedback-stabilized copper plate (FIGS. 1a and b), measures temperature changes on the suspended region with a resolution of approximately 25 μK in a bandwidth of approximately 10 mHz. Both thermistors (approximately 5 kΩ) were used in an AC Wheatstone bridge (see, e.g., Horowitz & Hill. *The art of electronics*. 2nd edition, Cambridge University Press, 1989) supplying an excitation voltage of approximately 5 mV across the thermistors.

Data collected from measurements of estimated conductance and temperature resolution indicated that the technology provides sub-nanowatt resolution (e.g., 250 pW=25 μK×10 μW/K). For example, the data (see, e.g., FIG. 4c) indicate that the technology resolves heat outputs with 250 pW resolution. Specifically, the plot indicates that as the heat input into the calorimeter (via a second thermistor embedded onto the capillary tube) is increased in steps of 250 pW, the measurement thermistor readily detects the resulting temperature changes. Further, the relatively small thermal time constant (e.g., approximately 60 seconds) provides a technology to perform metabolic measurements with approximately 1-minute time resolution over many hours and/or days.

Figure 4D:
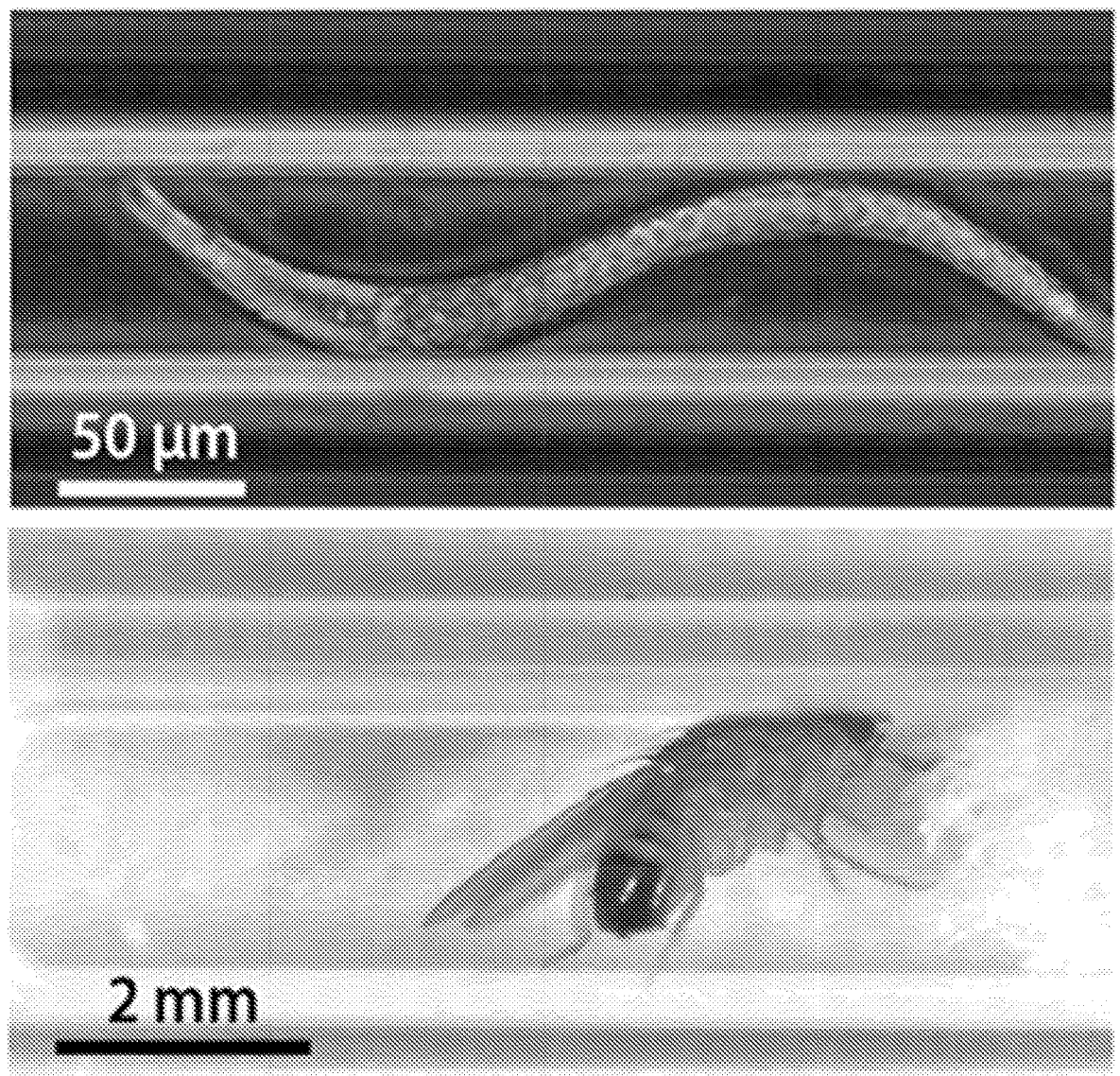

In some embodiments, the inner dimensions of the hollow capillary tube (e.g., to obtain the data in FIG. 4c) are relatively small (e.g., approximately 50 μm×50 μm) and are commensurate with the size of many biological organisms (e.g., Caenorhabditis elegans; see FIG. 4d, top panel). In some embodiments, the technology comprising continuously supplying and/or switching solutions in the capillary tube (e.g., M9 buffer for C. elegans; see, e.g., Chronis et al. (2007) "Microfluidics for in vivo imaging of neuronal and behavioral activity in Caenorhabditis elegans" Nature Methods 4: 727-731) via microfluidics to provide nutrients and otherwise create physiologically suitable conditions for the biological specimen. In some embodiments, microfluidic channels are fabricated from a PDMS stamp via standard soft-lithography techniques and are appropriately sized to mate with the ends of the glass capillary tube (FIG. 4a).

In some embodiments, the dimensions of the capillary tube used in the experiments are appropriately chosen for the cells and/or organism that is studied. For example, measurements of Drosophila melanogaster used tubes with an inner dimension (e.g., approximately 2 mm×2 mm) to accommodate a single fly inside the tube (see above). The larger tubes results in an increase in the thermal conductance of the tube but leaves the temperature resolution unchanged. For example, for the tube used in the Drosophila experiments, the conductance increased to 1 mW/K, resulting in a lower heat current resolution of approximately 100 nW. However, the decreased resolution did not pose a problem because the basal metabolic activity of larger organisms like Drosophila is significantly larger (approximately 1-10 μW per Drosophila).

In some embodiments, the technology provides for detecting a change in metabolic activity of approximately 1%. As described herein, the results from measurements of Drosophila are the first metabolic measurements made on an individual fly and establish the feasibility of performing metabolic measurements on organisms. These data also indicate that the technology, in some embodiments, finds use for system level-studies of modern biological problems.

Figure 11A:
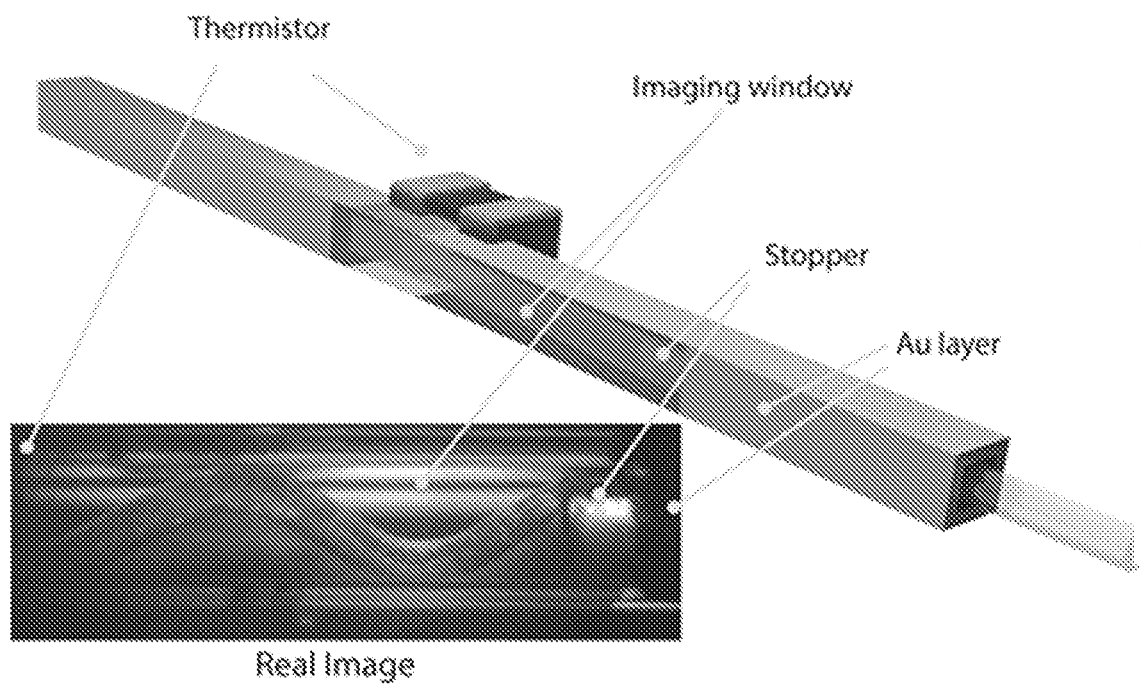
FIG. 11A to FIG. 11G show the experimental setup and calorimeter characterization for embodiments of the technology provided herein (see, e.g., Examples 4-8).
Figure 11B:
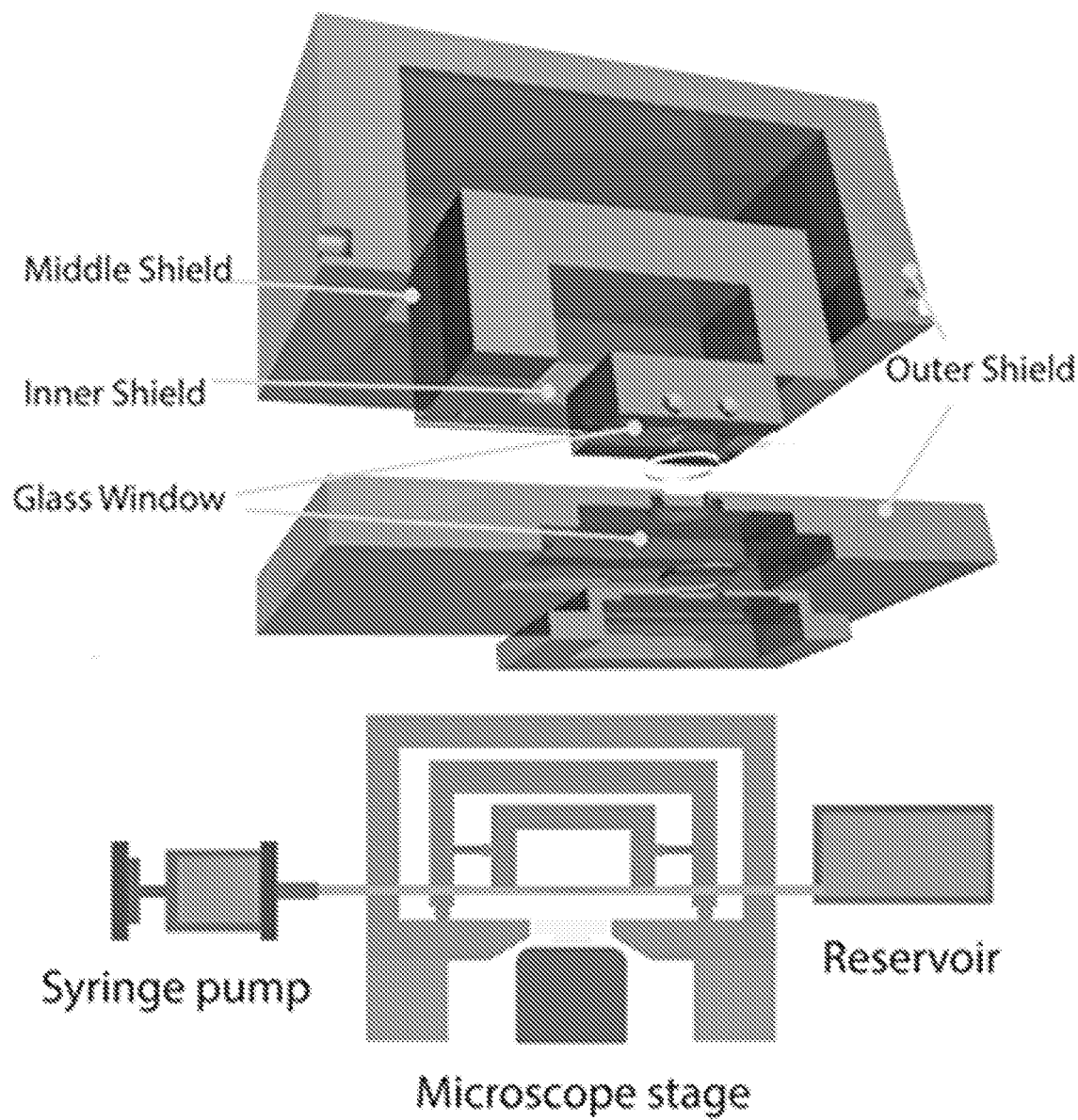

For example, during the development of embodiments of the technology described herein, experiments were conducted using the sub-nanowatt calorimeter described (e.g., having a calorimetric resolution of approximately 250 pW) to measure the metabolic activity of C. elegans in real time. C. elegans is a widely studied model organism that is easy to culture and propagate quickly because it has a short generation time. [7, 8] Previously, heat outputs measured for C. elegans have been reported as averaged values from groups of C. elegans because the calorimetric heat produced by a single C. elegans is too small to measure using previous technologies existing technique.[4-6, 12] Moreover, previous technologies did not provide for monitoring real-time heat output changes with respect to the organism size, activity (e.g., motion), and location. The best reported calorimetric data reported for biological and chemical studies has a resolution of 4.2 nW and the best reported calorimetric data reported for studies of C. elegans has a resolution of 170 nW. [13-15] Embodiments of the calorimeter described herein provided a heat resolution of approximately 250 pW for measurements of the metabolic heat output from a single C. elegans in a fluidic environment (FIG. 11A). As described herein, embodiments of the calorimeter were made by systematic engineering and integration of a three-shield calorimetric system that provides a stable temperature reference for the measurement chamber; a fluidic system for sample transfer and manipulation in the chamber; and, optionally, an inverted microscope-based imaging system to track the activity of a biological specimen (FIG. 11B).

Materials and Methods for Examples 4-8

Fabrication of the calorimeter tube. The calorimeter comprised a 20-mm long hollow borosilicate capillary tube (250×250 μm) coated with a 100-nm layer of gold on all sides except a small portion (approximately 2 mm) in the center to provide optical access for imaging. A 125-μm diameter borosilicate rod was placed near the center of the tube to trap the C. elegans in the chamber (FIG. 11A). Borosilicate has the advantages of transparency (e.g., for optical imaging), low thermal conductivity, and ease of fabrication; further, the tube comprised a square cross-section having a flat surface to aid imaging by avoiding aberrations due to curvature.

The capillary tubing system was produced by cleaning the capillary tubes (VITROTUBES) in an oxygen plasma cleaner to remove organic contaminants and improve surface adhesion for further processing. Next, the capillary tubes were masked with Kapton tape and then sputtered with a Ti/Au (10/100 nm) thin film in two steps using two masks. First, a first mask (approximately 400 μm across) was used in the center to provide isolated electrical leads. Second, a second mask (approximately 2 mm) was used on the opposite surface to provide optical access. The Au layer thickness was chosen to reduce radiative coupling of the tube to the environment, minimize and/or eliminate thermal conductance along the tube, and maintain a high quality surface for uninterrupted electronic flow. A 10-kOhm thermistor (Murata Electronics, −4% TCR, 0603 metric) was soldered between the two leads. The tubes were then flipped and mounted on the inner shield (IS). Electrical isolation between the IS and the tubes was provided by a 100-μm thin glass slide in. Silver epoxy was used to improve thermal contact. The 125-μm diameter borosilicate rod was then inserted into the capillary tube and epoxied at the exposed end. Finally, a PEEK tube (360 μm/150 μm OD/ID) was connected to the capillary tube through a PEEK tubing sleeve (800 μm/400 μm OD/ID) and all gaps were sealed with a vacuum epoxy. This tubing system was then anchored to the middle shield (MS) and passed through microfluidic connectors (MICROTIGHT Adapter PEEK 1/16" ID×360 μm w/Fittings) on the outer shield (OS) that provide vacuum feedthroughs to the outside.

Thermometry & Heater. Resistance-based thermometry in an AC-driven Wheatstone bridge configuration was used to measure temperature changes on the order of tens of μK. In its basic scheme, the Wheatstone bridge comprises a sensing resistor on a lower branch to the right with an associated resistance on the upper branch, while the left side is described as the matching side. Fixed resistors with an ultra-low temperature coefficient of resistance (Vishay Z201 Series Z-Foil Resistors, ±0.2 ppm/K) were used with the resistance values chosen to improve the stability and resolution based on previous studies [44]. To balance the Wheatstone bridge, a fixed matching resistance equal to that of the sensing thermistor resistance at its average temperature of operation was used and a potentiometer (Vishay Spectrol 534 series, ±20 ppm/K) was used on the top branch of the matching side of the Wheatstone bridge for fine tuning. The Wheatstone bridge was excited with a sinusoidal 1V peak-to-peak voltage using a waveform generator (Agilent 33210) at frequencies in the range of 10-100 Hz. The matching and the sensing signals were then fed into an instrumentation amplifier (Analog Devices AD524) where the common-mode signals were subtracted and differential mode AC signals were amplified (Gain=100, approximately 25 ppm/K). The amplitude of this amplified signal was then measured in a lock-in scheme (SRS 830) at a bandwidth of 100 mHz and recorded using Labview. The temperature resolution of the resulting circuit was quantified to be ±5 μK and did not set the noise floor of the measurement, which is limited by temperature drift.

A voltage-controlled current source was developed in which the emitter voltage of a transistor controlled through an op-amp provided the current to a polyimide heater on the collector side. The op-amp was configured to sum a manual voltage signal ($V_{man}$) providing heat to reach the desired temperature and a PID controlled voltage signal ($V_{PID}$) to stabilize the temperature at that point.

High Stability Temperature System. During the development of embodiments of the technology provided herein, experiments were conducted to minimize and/or eliminate thermal drifts in the system to improve the temperature resolution. In particular, a three-shield system with large thermal time constants was built and provided for the calorimeter device to decouple high frequency temperature fluctuations from the ambient environment and the temperature of each individual shield was controlled in a proportional-integral-derivative (PID) loop to minimize and/or eliminate low frequency temperature fluctuations. The OS was a three-piece structure that provided a vacuum enclosure (20×20×12 cm$^3$ volume and a 12-mm wall thickness) and that comprised electrical, optical, and fluidic feedthroughs that maintained a vacuum down to at least 10 μTorr. Thermistors (US Sensor Corp. USP12838) were bonded to each shield in a drilled hole at a representative location using epoxy (3M Scotch-Weld Epoxy Adhesive 2216 B/A) and provided temperature feedback for PID control. Polyimide flexible heaters (Omega KH series) were attached in series to each shield on different surfaces to provide uniform heat to the system. The MS was held on the bottom part of the OS supported by four spherical borosilicate balls. The IS was anchored to the MS through 3 polymer supports with a spherical end. These spherical contacts maximized the thermal resistance (OS/MS–50 mW/K and MS/IS–5 mW/K) while providing mechanical stability. Thermal time constants of the system were estimated to be approximately 3000 seconds, 12000 seconds, and 1600 seconds for the OS, MS, and IS, respectively, based on the thermal mass of copper shields and the calculated thermal conductance.

Optical Access for Real-Time Monitoring C. elegans Activity. During the development of embodiments of the technology provided herein, experiments were conducted to monitor C. elegans motion to analyze the C. elegans metabolic rate signal, location, and activity. The calorimeter was designed to provide optical access to the sample chamber to illuminate and image C. elegans in the chamber. However, designing the calorimeter to monitor C. elegans (e.g., through a transparent window) and maintain temperature stability was challenging because the measurement chamber was isolated from the MS and OS to minimize thermal fluctuation and illumination of the chamber provides heat to the chamber (e.g., in the form of infrared radiation). That is, providing illumination and imaging can disturb temperature stability.

Accordingly, the calorimeter was designed to minimize and/or eliminate temperature changes in the sample chamber caused by both unstable fluctuational ambient temperature and by infrared radiation. Specifically, the calorimeter comprised two layers of glass (e.g., infrared reflective and infrared absorbing) under the capillary tubes to minimize temperature fluctuations due to outside environmental temperature change. In addition, heat absorbing glass (KG5 Schott optical filter) was provided in the illumination and optical path to block infrared transmission by absorbing incoming infrared wavelengths and the observation window comprised infrared reflective glass to reflect infrared wavelengths away from the sample chamber. The temperature-controlled copper block was mounted on an inverted microscope (ZEISS) and a 10× objective (Nikon, Long working distance) was used to focus the measurement chamber through window. A power source (Agilent 6033A) provided power (3V, 0.75A) to the light source. A CCD camera (Qimaging, 2048×1024) was used to acquire real-time images (e.g., approximately 1 second per frame). A long exposure time (approximately 0.5 sec) was used so that images could be recorded with minimal illumination of the sample to minimize disturbing temperature stability. Recorded images were processed using Micro-Manager 1.4.22 in imageJ.

C. elegans Sizing and Activity Tracking. The mass/volume of an individual C. elegans for calculating mass-specific properties was estimated from images captured during the measurements described herein. Considering the axi-symmetric structure of the organism, the body was carefully divided into small sections of cylinders along the length of organism. The relevant dimensions (pixel lengths) for each section (diameter and width) were measured in ImageJ and converted to the true lengths using the known capillary dimensions as a reference. The volume of the organism was calculated as the sum of the volumes of all cylindrical sections. The mass of each organism was then derived from the total estimated volume with the density considered to be approximately 1.08 g/cm$^3$.

An activity factor providing a quantitative measure of organism activity was derived by performing image analysis (e.g., using ImageJ) on a plurality ("stack") of images collected at a frame rate of 1 frame per second. Initial brightness and contrast adjustments were performed on two image stacks where the second image stack was a duplicate of the first stack with a single frame offset. The two stacks were then subtracted to create a new stack that represented the organism activity. That is, subtracting a frame at the $(n+1)^{th}$ second from that at the $n^{th}$ second eliminated the motionless background and captured only the movement of the organism. To quantify this movement, the mean pixel intensity of each frame was then calculated and converted to a dimensionless activity factor ranging from 0 to 1, where 0 and 1 indicate the lowest and the highest activity levels of a given organism, respectively. Absolute quantities were used for activity comparison between N2 Wild-type and Daf-2 organisms instead of normalized quantities.

Time Constant Measurement of Calorimetry. The temperature signal monitored by a thermistor is delayed due to the calorimeter thermal time constant $\tau_{th}$. Accordingly, experiments were conducted during the development of embodiments of the technology provided herein in which the temperature signal read by a thermistor was monitored by applying joule heating using a calorimeter. A DC voltage was applied to a thermistor on the calorimeter from a voltage source to increase the temperature signal read by the thermistor by 1 mK. The signal response of the thermistor was monitored after the DC voltage was applied. The thermal time constant was determined to be 80 seconds.

Resolution Verification of Calorimetry. Further, the resolution of the calorimeter was assessed. A DC voltage was applied to increase the temperature of the calorimeter in increments and the temperature signal read by a thermistor was monitored. The calorimeter temperature signal clearly demonstrated response to changes of 10 µK, indicating a resolution of 270 pW for the calorimeter technology provided herein.

Sample Preparation and Control. During the development of embodiments of the technology provided herein, experiments were conducted to evaluate the precision of measuring the metabolic heat output of individual *C. elegans*. Measurements were conducted using the N2 wild-type strain of *C. elegans* and a DAF2 mutant. Worms were grown using Nematode growth medium (NGM) agar plates before they were selected to measure metabolic heat output. S Basal medium was prepared following standard protocols. The worm populations were cultured at room temperature on NGM agar plates together with *E. coli* OP50 as a food source. The *C. elegans* were transferred to S Basal medium using a pipette and the metabolic rate was monitored in S Basal Medium.

Restricting motion of active organisms could suppress *C. elegans* metabolic activity and thus could produce an incorrect result. Accordingly, *C. elegans* activity can be suppressed or, in some embodiments, a 150 µm×150 µm square cross sectional capillary tube was used to provide a free space for *C. elegans* to swim freely. S Basal medium was continuously flowing to provide oxygen to *C. elegans* for respiration.

One challenge was controlling *C. elegans* location during metabolic rate measurements. Unlike single cells or motionless organisms, *C. elegans* swims very actively and it is thus challenging to fix the location of a single organism in a designated spot for monitoring while not restricting its behavior. Thus, in some embodiments, a stopper was provided inside the calorimeter borosilicate capillary tube. In particular, the stopper comprised a 125-µm glass optical fiber with the coating peeled off to expose the glass fiber. This fiber was inserted inside of capillary tubes down to the window access.

Fluidics and Sample Loading. A liquid environment is preferred for most small size biological samples, such as *C. elegans* and single cells. Thus, a syringe pump (Harvard Apparatus Pico Plus 11, Hamilton 250 µL syringe) was used to load and unload biological samples during metabolic rate measurements. The syringe pump was connected on one end to the sample chamber and the other end was submerged in a reservoir. The experimental protocol comprised locating a *C. elegans* close to the PEEK tubing entrance using a pipette and increasing the pulling flow rate up to 3 µL/min to move the *C. elegans* into the tube by suction. After the *C. elegans* entered the tube, a time of up to 10 minutes was allowed to pass to allow the *C. elegans* to reach the measurement chamber. When the *C. elegans* reached the measurement chamber, the flow rate was reduced to approximately 100-200 nL/minute and measurements (e.g., calorimetric and imaging) were initiated. After measurements were recorded, the liquid flow was reversed and the liquid was flowed in the opposite direction at a rate of up to 5 uL/minute to move the *C. elegans* through the PEEK tubing and to the tubing entrance for removal. Using this protocol, a user can load and unload *C. elegans* into the calorimeter and successfully measure its metabolic heat generation with high resolution in real time.

Example 4—250 pW Calorimeter

Figure 11C:
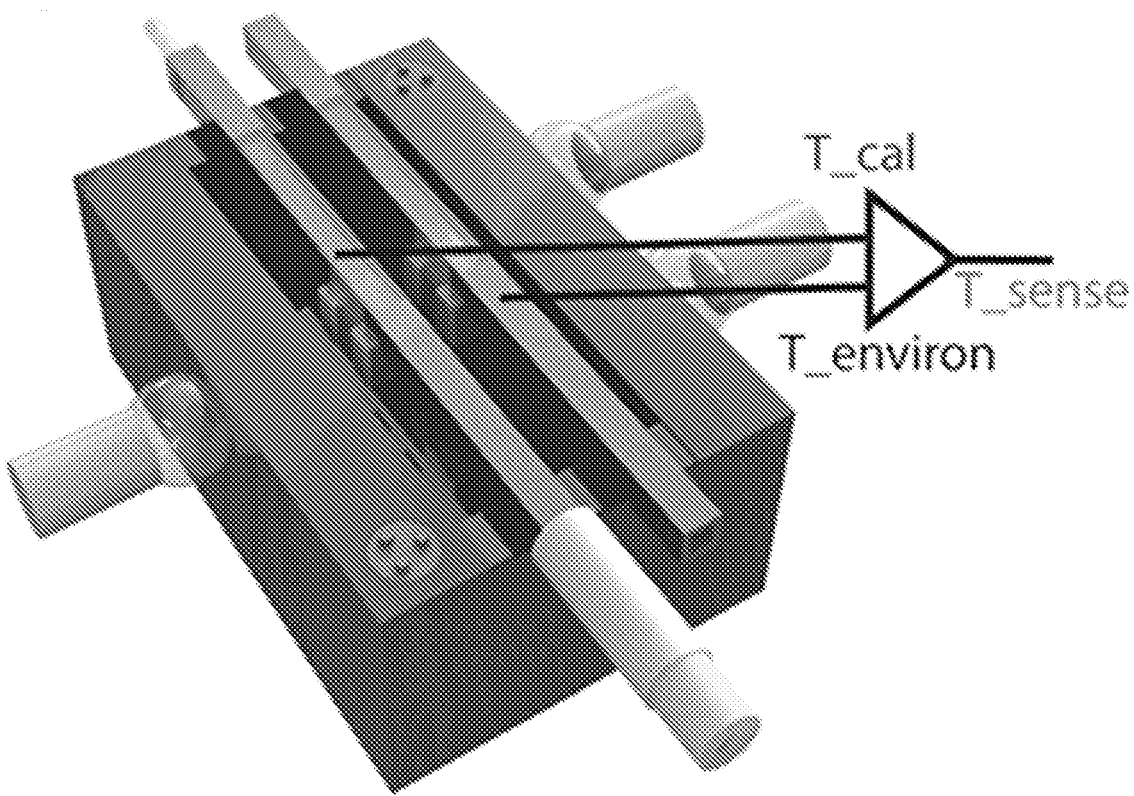

The resolution of a typical calorimeter ($\dot{Q}=G_{th}\times\Delta T$) can be improved in two ways, either by improving temperature resolution ($\Delta T$) or by reducing thermal conductance ($G_{th}$) [43]. The size of a calorimeter for studying biological organisms cannot be reduced to nanoscale dimensions due to the size of the liquid sample channel and the size of the biological organisms to be assayed. This limit imposed on calorimeter size imposes a limit on reducing thermal conductance. Accordingly, embodiments of the technology improve temperature resolution to provide a device having a resolution to measure sub-nanowatt heat generation. To provide a stable temperature reference to the chamber, embodiments of the calorimetric system comprise three copper shields: an outer shield (OS), a middle shield (MS), and an inner shield (IS), which are sequentially assembled by weak thermal links to each other and the ambient (FIG. 11B). The OS holds a vacuum level down to 10 µTorr with custom-made instrumentation, fluidic, and optical feedthroughs; and is controlled to a temperature stability of ±1 mK. Further, the MS and the IS provide temperature stabilities down to −20 µK through an active PID feedback control [44]. The MS rests on the OS using spherical supports and three ball arms anchor the IS to the MS. These ball contacts increase thermal contact resistance significantly by minimizing contact area. Both ends of the sensing and matching capillary tubes are anchored to the IS—with electrical access to the thermistors mounted in the center—for measuring temperature in a differential scheme (FIG. 11C). Differential scheme thermometry is employed to measure sensing thermistor resistance changes relative to the matching (reference) thermistor resistance. To realize differential scheme thermometry to measure small temperature change, an ac-driven Wheatstone bridge circuit was provided for the device.

Figure 11D:
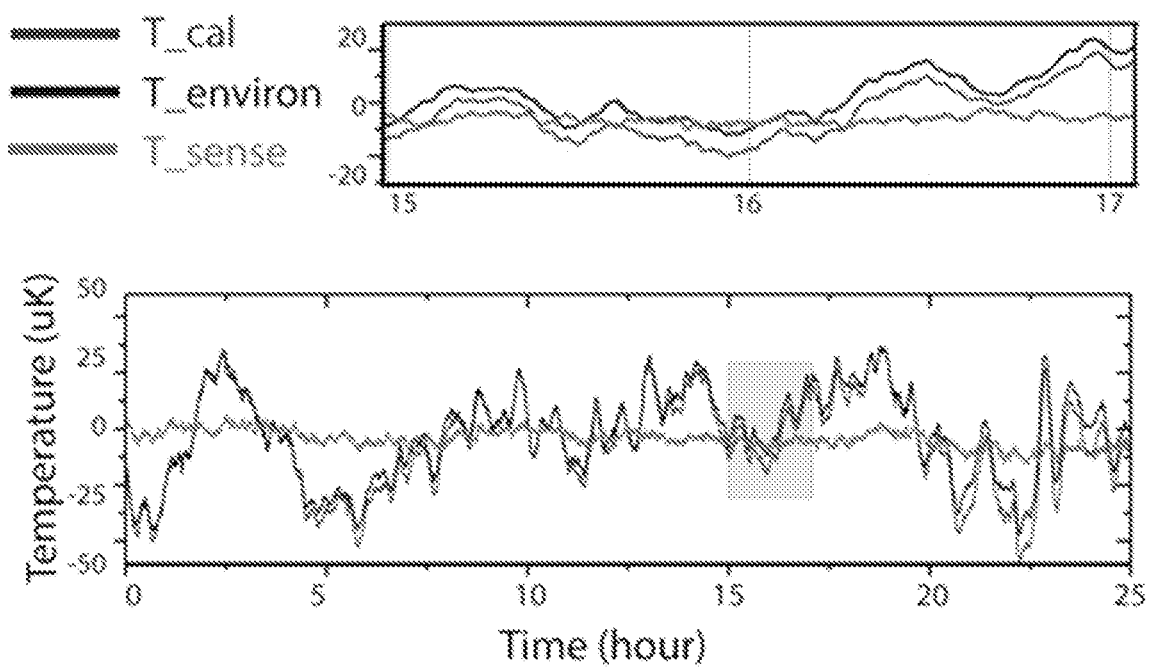

Embodiments of the technology comprise an imaging system to record the swimming motion of a worm in real time. The imaging system provides, e.g., recorded video that is used to analyze the measured metabolic heat output of worms and their positions and activities (e.g., by a correlative and/or functional relationship). The differential thermometry technology resulted in a noise equivalent temperature (NET) of ±20 µK within 2 hours and ±40 µK within 24 hours. This common mode noise is systematically reduced by monitoring the sensing and matching thermistor signals in a differential scheme leading to a NET of 4 µK for 2 hours with a drift of 10 µK for 24 hours (FIG. 11D).

Figure 11E:
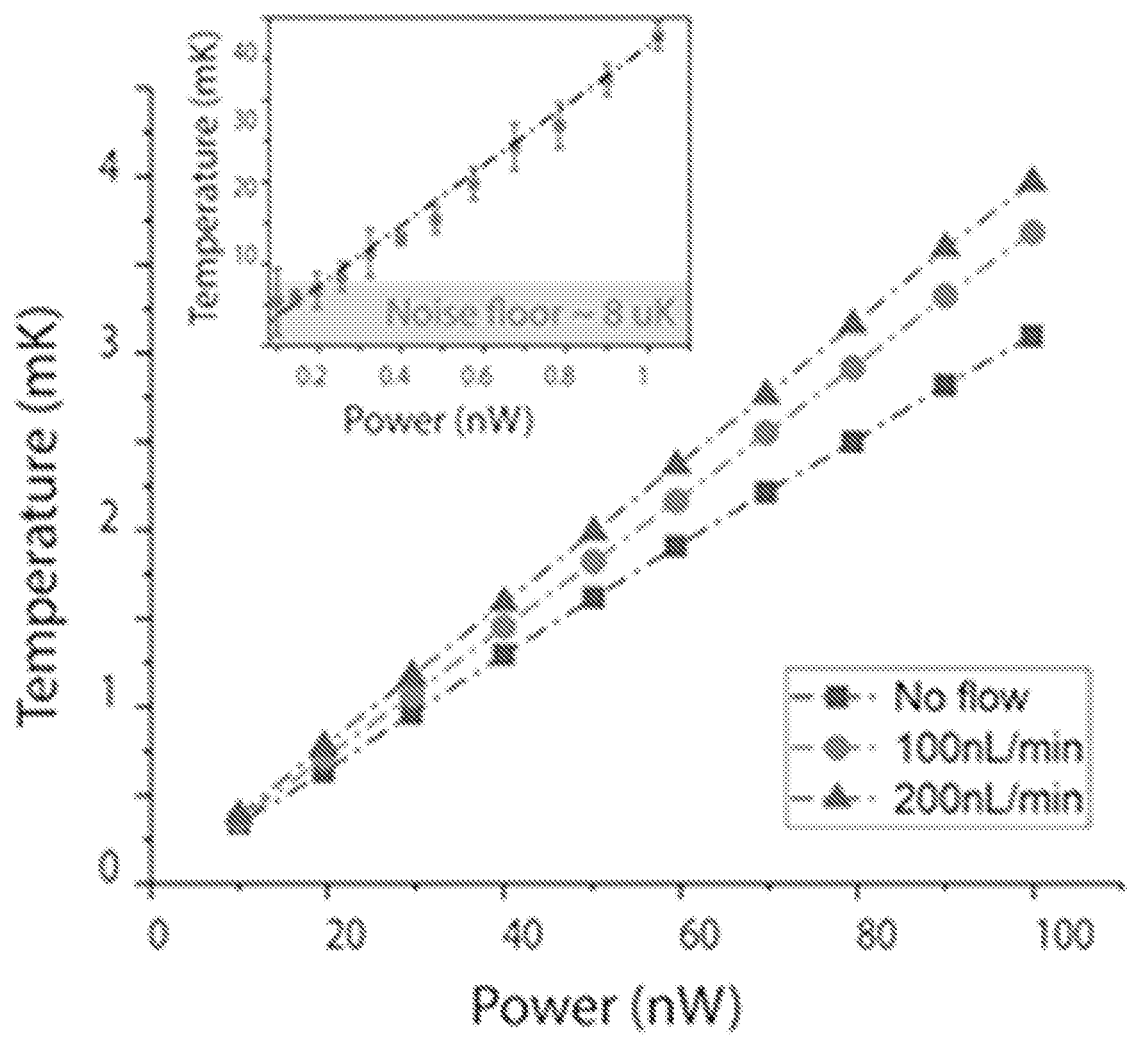
Figure 11F:
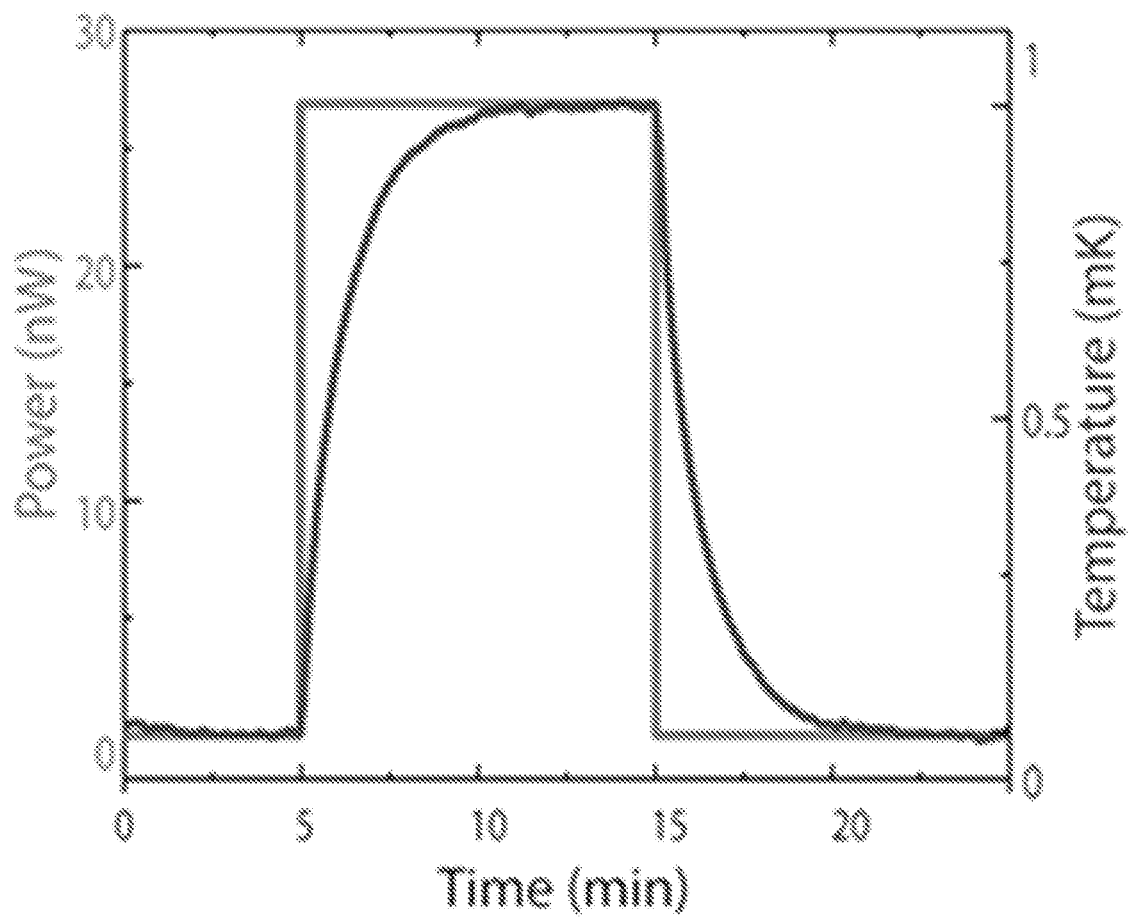
Figure 11G:
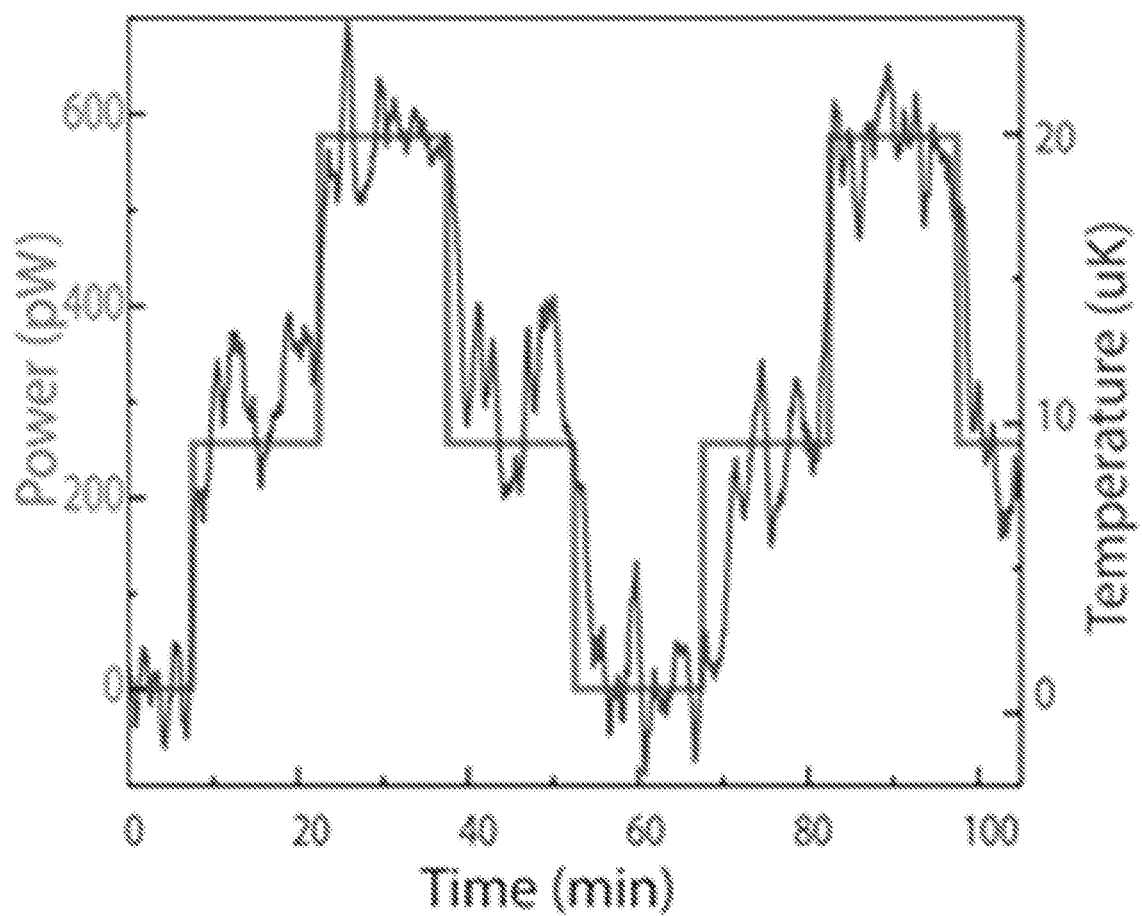

In a basic calorimetric system, the measurement chamber is thermally connected to a uniform temperature sink by a known thermal conductance of a $G_{th}$ and the heat output associated with the specimen causes temperature increase $\Delta T_{sense}$, which is detected by the thermistor. The heat output can then be directly acquired from $Q_{metabolic}=G_{th}\times\Delta T_{sense}$. Thus, heat resolution is limited by the thermal conductance of $G_{th}$ and the temperature resolution of $\Delta T_{sense}$. Accordingly, in some embodiments of the technology provided herein, the thermal conductance was attenuated by minimizing the contribution of several heat pathways and is determined to vary from approximately 25 to 31 µW/K based on flow rates of approximately 0 to 200 nL/minute (FIG. 11E) with a noise floor of approximately 8 µK (FIG. 11E, inset). The contribution to $G_{th}$ through borosilicate conduction is minimized by providing an approximately 1-minute thermal time constant for the calorimeter (FIG. 11F). Further, the thin gold layer coating and operating the calorimeter in a vacuum system reduced the radiative contribution and attenuated the convective contribution, respectively. As a result, embodiments of the calorimeter provided herein clearly resolves 250 pW, which is appropriate for metabolic measurements on biological specimens from a single cell to multi-cellular organisms (FIG. 11G).

Example 5—Measurement of C. elegans Metabolic Output

During the development of embodiments of the technology provided herein, the calorimeter technology was used to measure metabolic output from a single *Caenorhabditis elegans* organism. For *C. elegans* measurements, Nematode growth medium (NGM) agar plates, *Escherichia coli* OP50, and S Basal medium were prepared following standard protocols [40]. One challenging problem related to measuring live *C. elegans* is controlling *C. elegans* location during metabolic rate measurements. In particular, *C. elegans* swims actively, which presents challenges in localizing the worms at a designated spot for monitoring while not restricting their behavior. Restriction of *C. elegans* motion can suppress *C. elegans* metabolic activities [45, 46]. Thus, to avoid suppressing *C. elegans* activity, embodiments of the technology comprise a stopper inside of the measurement chamber tube.

Figure 12A:
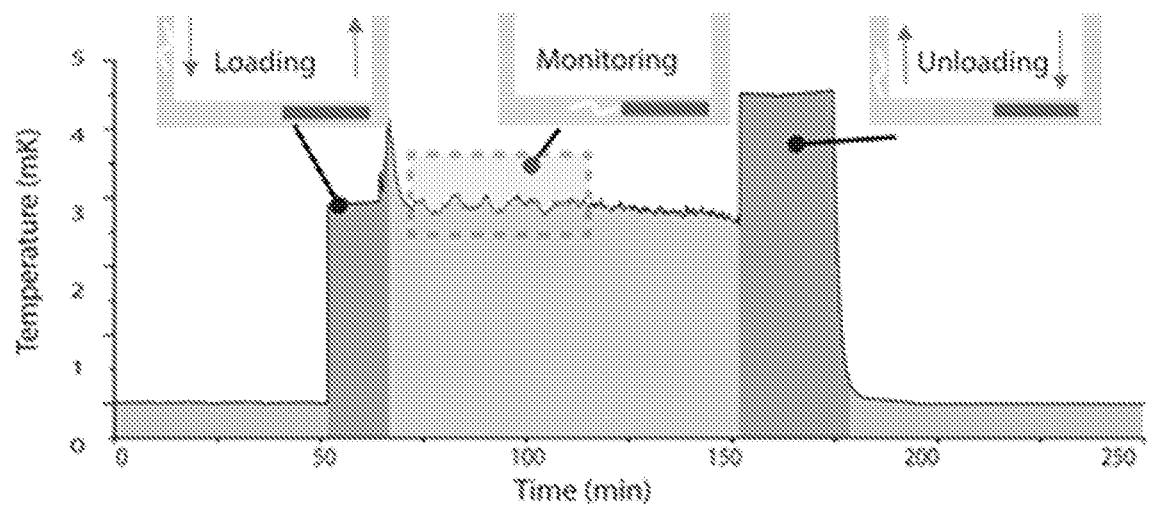
FIG. 12A to FIG. 12E show C. elegans metabolic heat output measurement and analysis.

In some embodiments, a liquid environment is provided for study of live organisms (e.g., *C. elegans* and single cells) to maintain organisms under normal physiological conditions. Accordingly, in some embodiments, a syringe pump was used to load and unload biological samples during metabolic rate measurements. The syringe pump was connected on one end to the calorimeter sample chamber and the other end was submerged in a reservoir. The experimental procedure comprised (FIG. 12A) locating a *C. elegans* close to the PEEK tubing entrance using a pipette and increasing the pulling flow rate to move a single *C. elegans* into the tube by suction. Once the *C. elegans* enters the tube, the procedure comprises waiting until the *C. elegans* reaches the measurement chamber. When the *C. elegans* reaches the measurement chamber, the procedure comprises reducing the flow rate to approximately 100 to 200 nL/minute and monitoring (blue box region) the *C. elegans* (e.g., monitoring heat output and imaging the *C. elegans*). When measurement is completed, the procedure comprises reversing the liquid flow to move the *C. elegans* to the PEEK tubing opening, thus flushing the *C. elegans* from the system.

Figure 12B:
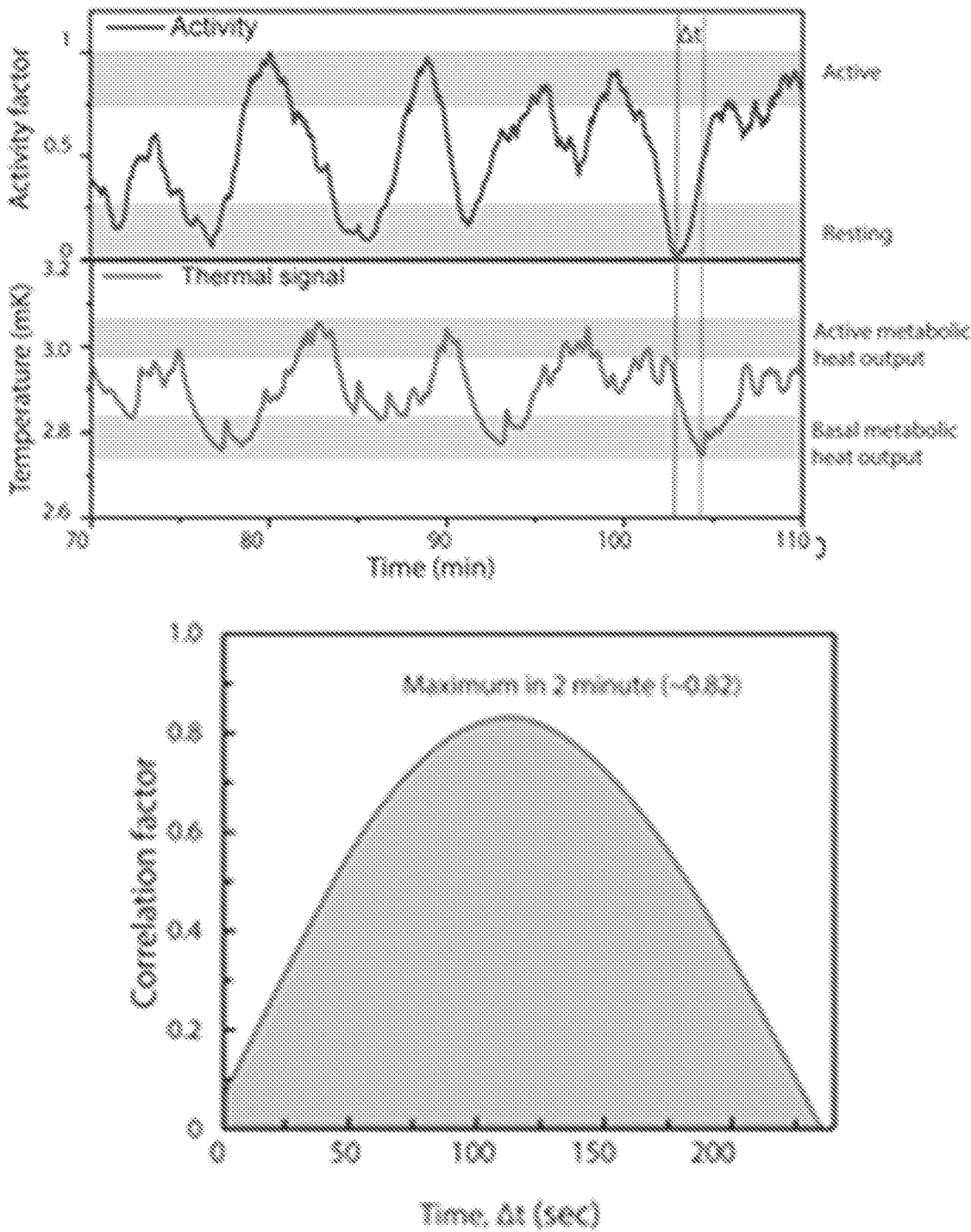

Data collected during these experiments indicated that the technology described herein measures metabolic heat generation with high resolution in real time (FIG. 12B). The blue line in FIG. 12B shows a representative activity trace from a single *C. elegans* and the red line provides the simultaneously obtained metabolic heat generation data. Two metabolic heat output values were defined in measurements: the average metabolic heat output and the standard metabolic heat output. Average metabolic heat output is defined by averaging all data during 30 minutes. Standard metabolic heat output is defined to average obtained when the *C. elegans* was clearly resting (FIG. 12B, green region). The red colored region indicates time when the *C. elegans* was mostly active as indicated by detected locomotive motion. The resting state (green colored region) was defined to analyze standard metabolic heat output. As a result, *C. elegans* activity and metabolic level are highly correlated up to 0.82 with a 2-minute time delay due to the calorimeter thermal time constant (FIG. 12B). These data and analyses confirmed that individual *C. elegans* metabolic heat output varies and the amount of change is approximately 10 percent of its total metabolic outputs.

Example 6—Metabolic Heat Measurements During C. elegans Development

Figure 12C:
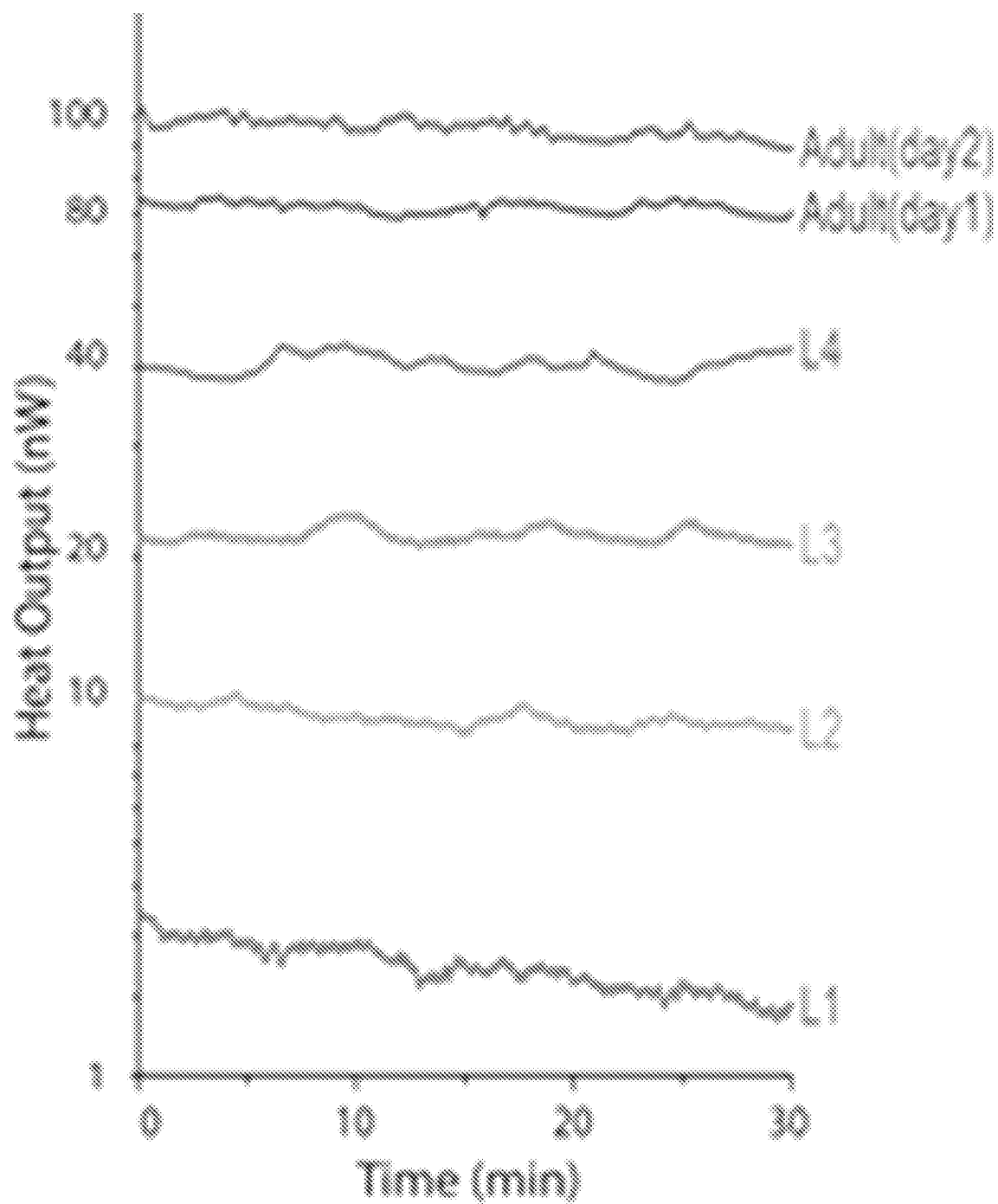

During the development of embodiments of the technology provided herein, experiments were conducted to measure the change of metabolic heat output during *C. elegans* development. In particular, experiments were conducted to monitor metabolic heat output from L1 to the adult stage of *C. elegans*. Most previous approaches were focused on measuring heat output of adult *C. elegans* because heat output of *C. elegans* in the larval developmental stages was too small to resolve with previous technologies [38, 39, 41]. *C. elegans* size increases more than an order an order of magnitude during development; accordingly, early stage *C. elegans* metabolic heat output is smaller in a similar manner. Metabolic heat output data collected using embodiments of the technology described herein indicated that the early stage L1 metabolic heat output was approximately 4 nW and it increased to approximately 100 nW in the adult worm (FIG. 12C), which is an increase of more than 20-fold during the development process. Previous experiments measuring developmental stage metabolic heat output reported that heat output was constant from the L3 to the L4 larval stages [41]. In contrast, measurements using the present technology indicated that metabolic heat output increases as throughout *C. elegans* development. The previous results may have resulted from recording data from an aggregate of hundreds of *C. elegans* in a sample, which would provide uncomfortable conditions for the worms during measurements. In contrast, the data collected during experiments conducted with the present technology to measure the heat output of a single worm indicated that the *C. elegans* metabolic rate varies more than an order as it grows.

Figure 12D:
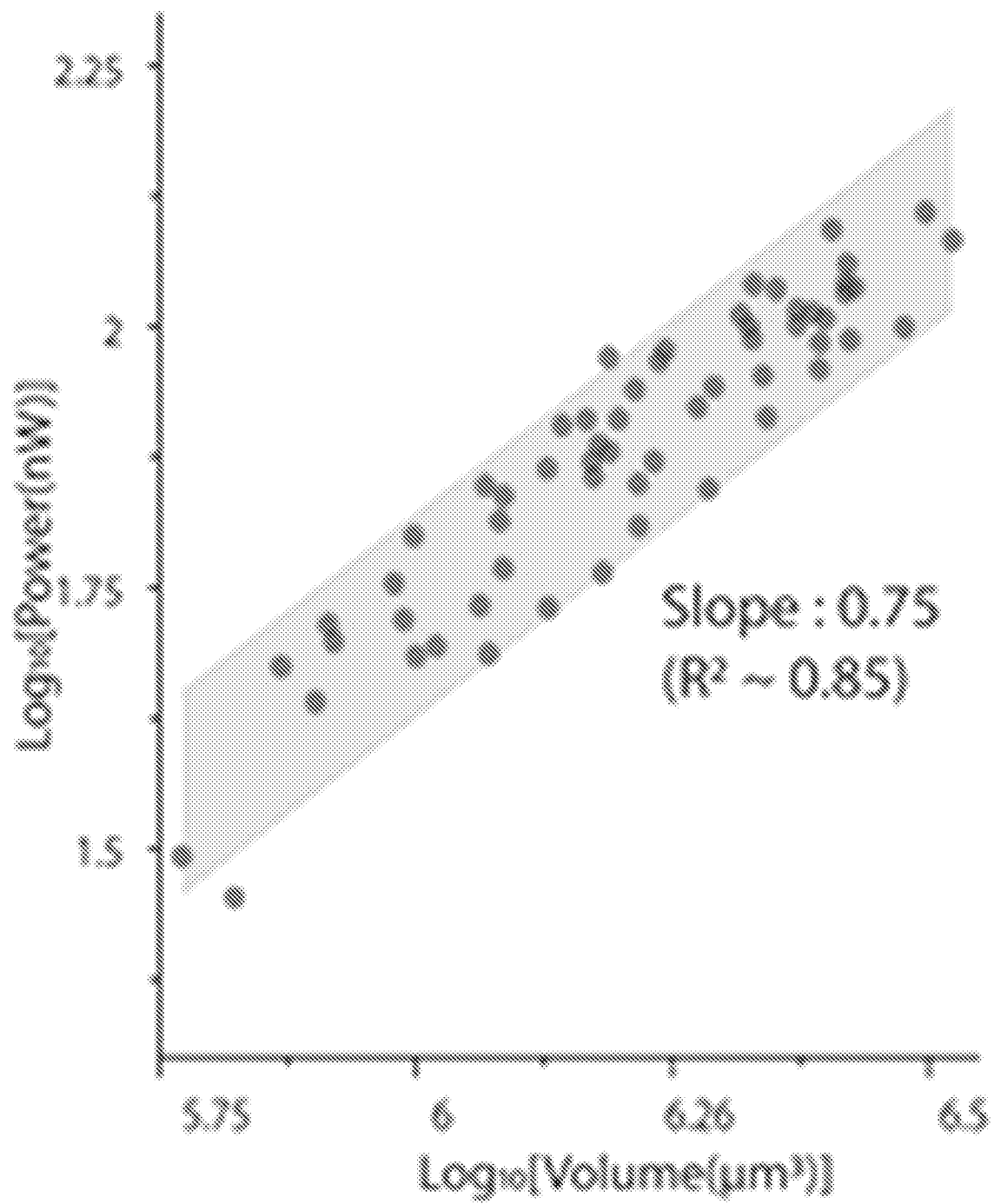
Figure 12E:
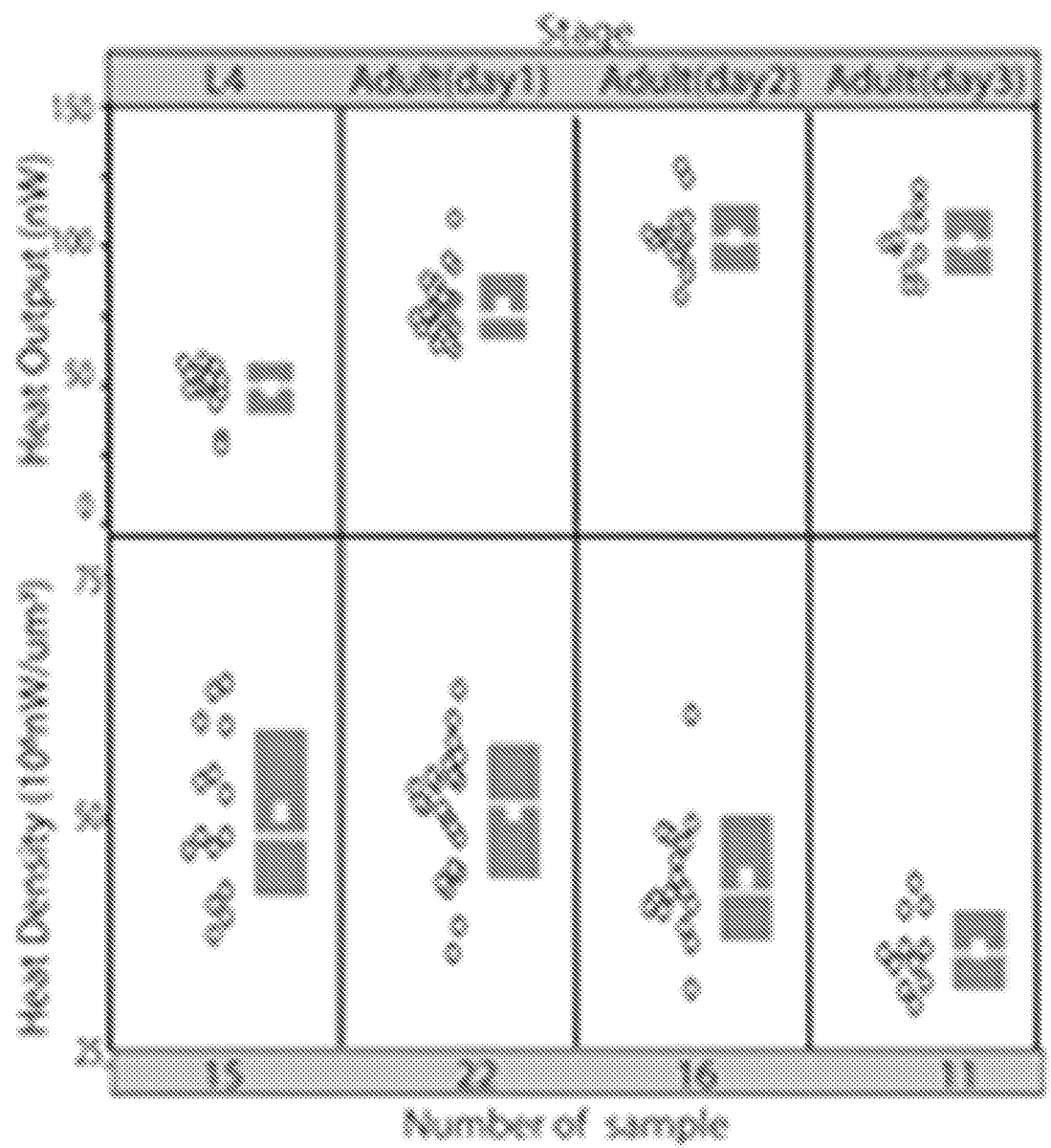

Moreover, the data collected were plotted to extract a scaling factor (FIG. 12D), e.g., to determine the relationship between metabolism and body size, which is important for metabolic studies. The Brody-Kleiber equation ($Q=aM^b$) is a representative equation where Q, M, a, and b represent the basal-metabolic heat output, body size, scalar constant, and exponential constant, respectively [47]. The body size (e.g., volume) of *C. elegans* was measured using imaging as described in the Methods above. Although most previous studies were conducted to determine interspecific relationships between metabolism and body side, the same principles apply for intraspecific analysis of metabolism and body size as a function of developmental stage. However, previous technologies did not have the sensitivity and/or resolution to measure the *C. elegans* metabolic rate at the larval stages and, accordingly, a *C. elegans* intraspecific exponent constant (b) could not be determined previously. Although Brody and Kleiber claimed that the exponent (b) is ¾, previous theories and experimental studies have proposed it to be in the range of between ⅔ and ¾. In the interspecific analysis performed using embodiments of the technology provided herein, data collected indicated that a value of ¾ for the exponent (b) appropriately describes the relationship of body size and metabolic rate. In addition, previous data that analyzed nematode species size and metabolic rate reported a value of 0.72, which accords with the data collected herein.

Example 7—C. elegans Metabolic Rate and Metabolic Rate Density

During the development of embodiments of the technology provided herein, experiments were conducted to measure and compare the metabolic rate and metabolic rate density (heat output divided by the volume) of *C. elegans* as a function of developmental stage and/or age. Metabolic rate increases until *C. elegans* reaches adult stage and heat output becomes stable or starts decreasing although the size of *C. elegans* increases. As a result, the metabolic heat density decreases from stage IA and this phenomena seems to be related to the aging [39].

The technology described herein provides embodiments of a calorimeter having a resolution of approximately 250 pW. In some embodiments, the calorimeter technology integrates a fluidic channel with real-time imaging and finds use in probing metabolic rates of small size model organisms (e.g., *C. elegans, D. melanogaster*, etc). Embodiments of the technology combine low thermal conductance capillary tubes ($G_{Th}$ is approximately 25 µW/K) and high-resolution thermometry ($\Delta T$ is approximately 10 µK). This technology provides an improvement in resolution of approximately two orders of magnitude over previous calorimeters used for *C. elegans* studies and an improvement in resolution of approximately one order of magnitude over the most sensitive calorimeters used previously for biological studies [41, 42]. Embodiments of the technology find use in measuring the metabolic rate of a single *C. elegans* in a real time from L1 to the adult stage. In addition, data collected indicated that the variation of metabolic heat generation is correlated to *C. elegans* locomotive activity, which contributes to 10% change of total metabolic heat output. Further, the data collected indicated that body size and metabolic heat output are related with an exponential factor of ¾, which supports Kleiber's law.

Example 8—Calorimeter with resolution of 25 pW or less

In some embodiments, the technology provides a calorimeter as described herein that has a resolution of 25 pW or less. As described herein, embodiments of the technology provide a calorimeter having a calorimetric resolution of approximately 250 pW by combining improved temperature stability via shielding; 2) reduced conductance (G) of the capillary tube (e.g., approximately 25 µW/K); and 3) improved temperature resolution ($\Delta T$) (e.g., approximately 10 µK). It should be noted the calorimetric resolution is provided by the equation ($\dot{Q}=G_{th}\times\Delta T$). Accordingly, embodiments of the calorimeter technology provide a resolution of approximately 25 pW or less by further lowering the conductance G to approximately 3 µW/K. In some embodiments, a calorimeter comprising an improved conductance G comprises a capillary tube comprising thinner walls, e.g., by producing the capillary by pulling a capillary tube in a glass electrode puller. For example, in some embodiments, decreasing the capillary wall thickness from approximately 100 µm to 10 µm provides a 10-fold reduction in the thermal conductance.

REFERENCES

1. Alberts, B., Wilson, J. H. & Hunt, T. Molecular biology of the cell, 5th edition. (Garland Science, New York; 2008).
2. Voet, D. & Voet, J. G. Biochemistry, 4th edition. (John Wiley & Sons, Hoboken, N.J.; 2011).
3. Kerr, E. M., Gaude, E., Turrell, F. K., Frezza, C. & Martins, C. P. Mutant Kras copy number defines metabolic reprogramming and therapeutic susceptibilities. Nature 531, 110-113 (2016).
4. Pavlova, N. N. & Thompson, C. B. The Emerging Hallmarks of Cancer Metabolism. Cell Metab 23, 27-47 (2016).
5. Spiegelman, B. M. & Flier, J. S. Obesity and the regulation of energy balance. Cell 104, 531-543 (2001).
6. DeBerardinis, R. J. & Thompson, C. B. Cellular Metabolism and Disease: What Do Metabolic Outliers Teach Us? Cell 148, 1132-1144 (2012).
7. Riera, C. E. & Dillin, A. Tipping the metabolic scales towards increased longevity in mammals. Nat Cell Biol 17, 196-203 (2015).
8. Lopez-Otin, C., Galluzzi, L., Freije, J. M. P., Madeo, F. & Kroemer, G. Metabolic Control of Longevity. Cell 166, 802-821 (2016).
9. Kaelin, W. G. & McKnight, S. L. Influence of Metabolism on Epigenetics and Disease. Cell 153, 56-69 (2013).
10. Zenobi, R. Single-Cell Metabolomics: Analytical and Biological Perspectives. Science 342, 1243259 (2013).
11. Fessenden, M. Metabolomics: Small Molecules, Single Cells. Nature 540, 153-155 (2016).
12. Lighton, J. R. B. Measuring metabolic rates: A manual for scientists. (Oxford University Press, Inc., New York; 2008).
13. Ferrannini, E. The Theoretical Bases of Indirect Calorimetry—a Review. Metabolism 37, 287-301 (1988).
14. Dickinson, M. H. & Lighton, J. R. B. Muscle Efficiency and Elastic Storage in the Flight Motor of *Drosophila*. Science 268, 87-90 (1995).
15. Walsberg, G. E. & Hoffman, T. C. M. Direct calorimetry reveals large errors in respirometric estimates of energy expenditure. Journal of Experimental Biology 208, 1035-1043 (2005).
16. Chancellor, E. B., Wikswo, J. P., Baudenbacher, F., Radparvar, M. & Osterman, D. Heat conduction calorimeter for massively parallel high throughput measurements with picoliter sample volumes. Applied Physics Letters 85, 2408-2410 (2004).
17. Johannessen, E. A., Weaver, J. M. R., Cobbold, P. H. & Cooper, J. M. Heat conduction nanocalorimeter for pl-scale single cell measurements. Applied Physics Letters 80, 2029-2031 (2002).
18. Xu, J., Reiserer, R., Tellinghuisen, J., Wikswo, J. P. & Baudenbacher, F. J. A microfabricated nanocalorimeter: Design, characterization, and chemical calibration. Analytical Chemistry 80, 2728-2733 (2008).
19. Lee, W., Fon, W., Axelrod, B. W. & Roukes, M. L. High-sensitivity microfluidic calorimeters for biological and chemical applications (vol 106, pg 15225, 2009). Proceeding of the National Academy of Sciences 106, 18040-18040 (2009).
20. Baker, K. D. & Thummel, C. S. Diabetic larvae and obese flies—Emerging studies of metabolism in *Drosophila*. Cell Metabolism 6, 257-266 (2007).
21. Padmanabha, D. & Baker, K. D. *Drosophila* gains traction as a repurposed tool to investigate metabolism. Trends in Endocrinology & Metabolism 25, 518-527 (2014).
22. Xu, K. Y., Zheng, X. Z. & Sehgal, A. Regulation of Feeding and Metabolism by Neuronal and Peripheral Clocks in *Drosophila*. Cell Metabolism 8, 289-300 (2008).
23. Sadat, S., Meyhofer, E. & Reddy, P. High resolution resistive thermometry for micro/nanoscale measurements. Review of Scientific Instruments 83 (2012).
24. Sadat, S., Meyhofer, E. & Reddy, P. Resistance thermometry-based picowatt-resolution heat-flow calorimeter. Applied Physics Letters 102 (2013).

25. Sadat, S. et al. Room temperature picowatt-resolution calorimetry. Applied Physics Letters 99 (2011).
26. Modest, M. F. Radiative Heat Transfer, 3rd edition. (Academic Press, London, England; 2013).
27. White, C. R. & Seymour, R. S. Mammalian basal metabolic rate is proportional to body mass$^{2/3}$. Proceedings of the National Academy of Sciences 100, 4046-4049 (2003).
28. Hulbert, A. J. et al. Metabolic rate is not reduced by dietary-restriction or by lowered insulin/IGF-1 signalling and is not correlated with individual lifespan in *Drosophila melanogaster*. Experimental Gerontology 39, 1137-1143 (2004).
29. West, G. B., Woodruff, W. H. & Brown, J. H. Allometric scaling of metabolic rate from molecules and mitochondria to cells and mammals. Proceedings of the National Academy of Sciences 99, 2473-2478 (2002).
30. Lin, S. J. et al. Calorie restriction extends Saccharomyces cerevisiae lifespan by increasing respiration. Nature 418, 344-348 (2002).
31. Houthoofd, K. et al. No reduction of metabolic rate in food restricted *Caenorhabditis elegans*. Experimental Gerontology 37, 1359-1369 (2002).
32. Weindruch, R., Walford, R. L., Fligiel, S. & Guthrie, D. The Retardation of Aging in Mice by Dietary Restriction—Longevity, Cancer, Immunity and Lifetime Energy-Intake. Journal of Nutrition 116, 641-654 (1986).
33. Mattison, J. A. et al. Impact of caloric restriction on health and survival in rhesus monkeys from the NIA study. Nature 489, 318-321 (2012).
34. Colman, R. J. et al. Caloric restriction reduces age-related and all-cause mortality in rhesus monkeys. Nature Communication 5, 3557 (2014).
35. Bishop, N. A. & Guarente, L. Two neurons mediate diet-restriction-induced longevity in Celegans. Nature 447, 545-549 (2007).
36. Eckel-Mahan, K. & Sassone-Corsi, P. Metabolism and the Circadian Clock Converge. Physiology Reviews 93, 107-135 (2013).
37. Rutter, J., Reick, M. & McKnight, S. L. Metabolism and the control of circadian rhythms. Annual Reviews of Biochemistry 71, 307-331 (2002).
38. Braeckman, B. P., K. Houthoofd, and J. R. Vanfleteren, Assessing metabolic activity in aging *Caenorhabditis elegans*: concepts and controversies. Aging Cell, 2002. 1(2): p. 82-88.
39. Van Voorhies, W. A., Metabolism and aging in the nematode *Caenorhabditis elegans*. Free Radical Biology and Medicine, 2002. 33(5): p. 587-596.
40. Corsi, A. K., B. Wightman, and M. Chalfie, A Transparent Window into Biology: A Primer on *Caenorhabditis elegans* (vol 200, pg 387, 2015). Genetics, 2015. 201(1): p. 339-339.
41. Krenger, R., T. Lehnert, and M. A. M. Gijs, Dynamic microfluidic nanocalorimetry system for measuring *Caenorhabditis elegans* metabolic heat. Lab on a Chip, 2018. 18(11): p. 1641-1651.
42. Lee, W., et al., High-sensitivity microfluidic calorimeters for biological and chemical applications. Proceedings of the National Academy of Sciences of the United States of America, 2009. 106(36): p. 15225-15230.
43. Incropera, F. P. and F. P. Incropera, Fundamentals of heat and mass transfer. 6th ed. 2007, Hoboken, N.J.: John Wiley. xxv, 997 p.
44. Fiorino, A., et al., Parallelized, real-time, metabolic-rate measurements from individual *Drosophila*. Scientific Reports, 2018. 8.
45. Berger, S., et al., Long-term *C. elegans* immobilization enables high resolution developmental studies in vivo. Lab on a Chip, 2018. 18(9): p. 1359-1368.
46. Chokshi, T. V., A. Ben-Yakar, and N. Chronis, CO2 and compressive immobilization of *C. elegans* on-chip. Lab on a Chip, 2009. 9(1): p. 151-157.
47. Kleiber, M., Body Size and Metabolic Rate. Physiological Reviews, 1947. 27(4): p. 511-541.

All publications and patents mentioned in the above specification are herein incorporated by reference in their entirety for all purposes. Various modifications and variations of the described compositions, methods, and uses of the technology will be apparent to those skilled in the art without departing from the scope and spirit of the technology as described. Although the technology has been described in connection with specific exemplary embodiments, it should be understood that the invention as claimed should not be unduly limited to such specific embodiments. Indeed, various modifications of the described modes for carrying out the invention that are obvious to those skilled in the art are intended to be within the scope of the following claims.

We claim:
1. A calorimetry apparatus comprising:
    a) a single sample chamber comprising a tube having a thermal conductivity of approximately 1 W m$^{-1}$ K$^{-1}$;
    b) a sensing thermistor thermally coupled to said tube; and
    c) an imaging system configured to record movement of a biological organism placed in said single sample chamber.
2. The calorimetry apparatus of claim 1, further comprising a high thermal conductivity material attached to an outside surface of said tube, wherein said high thermal conductivity material has a thermal conductivity greater than 300 W m$^{-1}$ K$^{-1}$.
3. The calorimetry apparatus of claim 1, wherein said tube is suspended on its ends.
4. The calorimetry apparatus of claim 1, wherein said tube comprises glass.
5. The calorimetry apparatus of claim 1, further comprising a circuit comprising said sensing thermistor, a reference thermistor, and high thermal stability resistors having a rated temperature coefficient of approximately 0.2 ppm/K.
6. The calorimetry apparatus of claim 1, wherein said apparatus has a thermal conductance of approximately 1 to 5 μW/K and/or is capable of detecting heat at a resolution of 50-150 pW or 10-50 μK.
7. A calorimetry apparatus comprising:
    a) a single sample chamber comprising a tube having a thermal conductivity of approximately 1 W m$^{-1}$ K$^{-1}$, wherein said tube comprises an optical window that transmits electromagnetic wavelengths of 315 nm-710 nm and absorbs infrared radiation; and
    b) a sensing thermistor thermally coupled to said tube.
8. The calorimetry apparatus of claim 7, further comprising a high thermal conductivity material attached to an outside surface of said tube, wherein said high thermal conductivity material has a thermal conductivity greater than 300 W m$^{-1}$ K$^{-1}$.
9. The calorimetry apparatus of claim 7, wherein said tube is suspended on its ends.
10. The calorimetry apparatus of claim 7, wherein said tube comprises glass.
11. The calorimetry apparatus of claim 7, further comprising a circuit comprising said sensing thermistor, a ref- erence thermistor, and high thermal stability resistors having a rated temperature coefficient of approximately 0.2 ppm/K.

12. The calorimetry apparatus of claim 7, wherein said apparatus has a thermal conductance of approximately 1 to 5 µW/K and/or is capable of detecting heat at a resolution of 50-150 pW or 10-50 µK.

\* \* \* \* \*